(12) United States Patent
Shaw et al.

(10) Patent No.: US 8,647,818 B2
(45) Date of Patent: Feb. 11, 2014

(54) MOLECULAR SCAFFOLDS FOR HIV-1 IMMUNOGENS

(75) Inventors: George M. Shaw, Birmingham, AL (US); Beatrice H. Hahn, Birmingham, AL (US); Frederic Bibollet-Ruche, Birmingham, AL (US); Peter D. Kwong, Washington, DC (US)

(73) Assignees: UAB Research Foundation, University of Alabama—Birmingham, Birmingham, AL (US); The United States of America, as represented by the Secretary, Department of Health and Human Services (Hereinafter the Government) Office of Technology Transfer, National Institutes of Health, Washington, DC (US)

( * ) Notice: Subject to any disclaimer, the term of this patent is extended or adjusted under 35 U.S.C. 154(b) by 1008 days.

(21) Appl. No.: 11/816,624

(22) PCT Filed: Feb. 16, 2006

(86) PCT No.: PCT/US2006/005363
§ 371 (c)(1),
(2), (4) Date: Nov. 12, 2008

(87) PCT Pub. No.: WO2006/091455
PCT Pub. Date: Aug. 31, 2006

(65) Prior Publication Data
US 2009/0162390 A1   Jun. 25, 2009

Related U.S. Application Data

(60) Provisional application No. 60/669,612, filed on Apr. 8, 2005, provisional application No. 60/654,340, filed on Feb. 18, 2005.

(51) Int. Cl.
*C12Q 1/70* (2006.01)
*A61K 39/00* (2006.01)
*A61K 39/12* (2006.01)
*A61K 39/21* (2006.01)
*A61K 39/38* (2006.01)
*C07K 16/00* (2006.01)

(52) U.S. Cl.
USPC ......... 435/5; 435/339; 435/339.1; 530/388.3; 530/388.35; 424/184.1; 424/185.1; 424/186.1; 424/187.1; 424/188.1

(58) Field of Classification Search
None
See application file for complete search history.

(56) References Cited

U.S. PATENT DOCUMENTS

| 5,866,137 | A | 2/1999 | Rovinski et al. |
| 5,912,176 | A | 6/1999 | Wang et al. |
| 6,328,973 | B1 | 12/2001 | Devico et al. |
| 2008/0096187 | A1* | 4/2008 | Shaw et al. ............... 435/5 |

FOREIGN PATENT DOCUMENTS

| WO | WO 03/033666 A2 | 4/2003 |
| WO | WO 2004/052933 A2 | 6/2004 |
| WO | WO 2005/111621 A2 | 11/2005 |
| WO | WO2005111621 | * 11/2005 ........... G01N 33/569 |

OTHER PUBLICATIONS

Robert-Guroff, et al. Cross-Neutralization of Human Immunodeficiency Virus Type 1 and 2 and Simian Immunodeficiency Virus Isolates. J. Virol. 1992; 66(6):3602-3608.*

Nyambi, et al. Study of the Dynamics of Neutralization Escape Mutants in a Chimpanzee Naturally Infected with the Simian Immunodeficiency Virus SIVcpz-ant. J. Virol. 1997; 71(3):2320-2330.*

Han, et al. The use of a chimera HIV-1/HIV-2 envelope protein for immunodiagnosis of HIV infection: its expression and purification in *E. coli* by use of a translation initiation site within HIV-1 env gene. Biochemistry and molecular biology international. 1998; 46(3): p. 607-17.*

Wagner, et al. Construction, Expression, and Immunogenicity of Chimeric HIV-1 Virus-like Particles. Virology. 1996; 220: 128-140.*

Hansen, et al. An O-linked carbohydrate neutralization epitope of HIV-1 gp120 is expressed by HIV-1 env gene recombinant vaccinia virus. Arch Virol. 1992; 126: 11-20.*
Schweighardt, et al. R5 Human Immunodeficiency Virus Type 1 (HIV-1) Replicates More Efficiently in Primary CD4+ T-Cell Cultures Than X4 HIV-1. J. Virol. 2004; 78(17): 9164-9173.*
Schanzer, et al. Development of Tetravalent, Bispecific CCR5 Antibodies with Antiviral Activity against CCR5 Monoclonal Antibody-Resistant HIV-1 Strains. Antimicrob Agents Chemother. 2011; 55(5): 2369-2378.*
Chen, et al. AFM force measurements of the gp120-sCD4 and gp120 or CD4 antigen-antibody interactions. Biochemical and Biophysical Research Communications. 2011; 407(2): 301-306.*
Scott, et al., Evaluation of a candidate human immunodeficiency virus type 1 (HIV-1) vaccine in macaques: effect of vaccination with HIV-1 gp120 on subsequent challenge with heterologous simian immunodeficiency virus—HIV-1 chimeric virus. Journal of General Virology. 1998; 79: 423-432.*
Mamounas, et al. An Infectious Chimeric Human Immunodeficiency Virus Type 2 (HIV-2) Expressing the HIV-1 Principal Neutralizing Determinant. J. Virol. 1995; 69(10): 6424-6429.*
Zwick, et al. Broadly Neutralizing Antibodies Targeted to the Membrane-Proximal External Region of Human Immunodeficiency Virus Type 1 Glycoprotein gp41. J. Virol. 2001; 75(22): 10892-10905.*
Wagner, et al. Construction, Expression, and Immunogenicity of Chimeric HIV-1 Virus-like Particles. Virology. 1996; 220:128-140.*
Zwick, et al. Broadly Neutralizing Antibodies Targeted to the Membrane-Proximal External Region of Human Immunodeficiency Virus Type 1 Glycoprotein gp41. J. Virol. 2001;75(22): 10892-10905.*
Burton, et al. HIV vaccine design and the neutralizing antibody problem. Nature Immunol. 2004; 5(3): 233-236.*
Zwick, M.B. The membrane-proximal external region of HIV-1 gp41: a vaccine target worth exploring. AIDS, 2005; 19: 1725-1737.*
Zwick, et al. Anti-Human Immunodeficiency Virus Type 1 (HIV-1) Antibodies 2F5 and 4E10 Require Surprisingly Few Crucial Residues in the Membrane-Proximal External Region of Glycoprotein gp41 to Neutralize HIV-1. J. Virol. 2005; 79(2): 1252-1261.*
Breuer, J., et al., "Human Immunodeficiency Virus Type 2 (HIV-2) env Gene Analysis: Prediction of Glycoprotein Epitopes Important for Heterotypic Neutralization and Evidence for Three Genotype Clusters within the HIV-2a Subtype" (1995) Journal of General Virology, pp. 333-345, vol. 76.
Ofek, G., et al., "Structure and Mechanistic Analysis of the Anti-Human Immunodeficiency Virus Type 1 Antibody 2F5 in Complex with Its gp41 Epitope" (Oct. 2004) Journal of General Virology, pp. 10724-10737, vol. 78.
Barnett, S.W. et al., "Distinguishing Features of an Infectious Molecular Clone of the Highly Divergent and Noncytopathic Human Immunodeficiency Virus Type 2 UCI Strain," Journal of Virology, Feb. 1993, pp. 1006-1014, vol. 67, No. 2.
Burton, D. R., et al., "HIV Vaccine Design and the Neutralizing Antibody Problem," Nature Immunology, Mar. 2004, pp. 233-236, vol. 5, No. 3.
Kong, L.I., et al., "West African HIV-2-Related Human Retrovirus with Attenuated Cytopathicity," Science, Jun. 10, 1988, pp. 1525-1529, vol. 240.
Mamounas, M., et al., "An Infectious Chimeric Human Immunodeficiency Virus Type 2 (HIV-2) Expressing the HIV-1 Principal Neutralizing Determinant," Journal of Virology, Oct. 1995, pp. 6424-6429, vol. 69, No. 10.

Nabel., G.J., "Close to the Edge: Neutralizing the HIV-1 Envelope," Science, Jun. 24, 2005, pp. 1878-1879, vol. 308.
Shi, Y., et al., "Evolution of Human Immunodeficiency Virus Type 2 Coreceptor Usage, Autologous Neutralization, Envelope Sequence and Glycosylation," Journal of General Virology, 2005, pp. 3385-3396, vol. 86.
Thomas, E.R., et al., "CD4-dependent and CD4-independent HIV-2: Consequences for Neutralization," AIDS, 2003, pp. 291-300, vol. 27.
Weiss, R.A., et al., :"HIV-2 Antisera Cross-neutralize HIV-1," AIDS, 1988, pp. 95-100, vol. 2.
Zwick, M.B., et al., "Broadly Neutralizing Antibodies Targeted to the Membrane-Proximal External Region of Human Immunodeficiency Virus Type 1 Glycoprotein gp41," Journal of Virology, Nov. 2001, pp. 10892-10905, vol. 75, No. 22.
Zwick, M.B., et al., "Anti-Human Immunodeficiency Virus Type 1 (HIV-1) Antibodies 2F5 and 4E10 Require Surprisingly Few Crucial Residues in the Membrane-Proximal External Region of Glycoprotein gp41 to Neutralize HIV-1," Journal of Virology, Jan. 2006, pp. 1252-1261, vol. 79, No. 2.

* cited by examiner

*Primary Examiner* — Jeffrey Stucker
*Assistant Examiner* — Stuart W Snyder
(74) *Attorney, Agent, or Firm* — Alston & Bird LLP

(57) ABSTRACT

Methods and compositions are provided which employ chimeric polypeptides having at least one heterologous epitope for a human immunodeficiency virus type 1 (HIV-1) neutralizing antibody. These chimeric polypeptides behave as molecular scaffolds which are capable of presenting the various heterologous HIV-1 epitopes. The invention demonstrates that a heterologous epitope recognized by the HIV-1 neutralizing antibody can be more fully exposed to neutralizing antibodies when presented within the backbone of the chimeric polypeptide than when the epitope is presented within the context of an HIV-1 backbone. Polynucleotides encoding these chimeric polypeptides are also provided. Immunogenic compositions are provided which comprise a chimeric polypeptide having at least one heterologous epitope that interacts with an HIV-1 neutralizing antibody. Immuno genie compositions comprising chimeric polynucleotides encoding the chimeric polypeptides of the invention are also provided. Vaccines comprising such immunogenic compositions are also provided. Further provided are methods which employ the immunogenic compositions of the invention. Such methods include, for example, methods for eliciting an immune response in a subject, methods for generating antibodies specific for the chimeric polypeptide or the chimeric polypeptide, and methods for inhibiting or preventing infection by HIV-1 in a subject.

26 Claims, 14 Drawing Sheets

FIG. 1A

FROM FIG. 1A

```
          ΔΔΔ Δ
7312A     FNGTRAENRTYMYWHS---KDNRTIISLNKYYNLTIHCKRPGNKTVVPITLMSGLVFHSQP
UC1       FNGTRTENRTYMYWHS---KDNRTIISLNKYYNLTMHCRRPGNKTVIPITIMSGLNFHSQP
MAC239    FNGTRTENRTYIYWHG---RDNRTIISLNKYYNLTMKCRRPGNKTVLPVTIMSGLVFHSQP
VER-TY01   LNGSYHENRTQIWQKHRVNNNTVLILFNKHYNLSVT-CRRPGNKTVLPVTIMAGLVFHSQK
YU2       LNGSLAEEEIVIRSEN--FTNNAKTIIVQLNESVVINCTRPNNNTRKSINI--GPGRALYT
HXB2      LNGSLAEEEVVIRSVN--FTDNAKTIIVQLNTSVEINCTRPNNNTRKRRIRIQRGPGRAFVT
                *              *  **** ***    ***  **      *

V3
                                                  ΔΔΔΔΔ  Δ
7312A     IN----KRPRQAWCWFKG-EWREAMQEVKQTLIKHP---RYKGTNDTRNITFTKPGTGSDPE
UC1       LN----TRPRQAWCWFKG-NWIEAIREVKETIIKHP---RYKGTNNTERIRLVGPSAGSDPE
MAC239    IN----DRPKQAWCWFGG-KWKDAIKEVKQTIVKHP---RYTGTNNTDKINLTAPGG--DPE
VER-TY01   YN----MKLRQAWCHFEG-NWRGAWREVKQKIVELPKDRYKGTNNTEHIYLQRQW-G-DPE
YU2       TGEIIGDIRQAHCNLSKTQWENTLEQIAIKLKEQF------GNNKTIIFN----PSSGGDPE
HXB2      IG-KIGNMRQAHCNISRAKWNNTLKQIASKLREQF------GNNKTIIFK----QSSGGDPE
           *    * *  ** *  **        *            *****               419

ΔΔΔΔ
7312A     VAYMWTNCRGEFLYCNMTWFLNWVENRTG----------QTQHNYAPCHIKQ
UC1       VRHMWTNCRGEFFYCNMTWFLNWVENRTG----------TTQKNYVTCHIKQ
MAC239    VTFMWTNCRGEFLYCKMNWFLNWVEDRNTANQKPKE----QHKRNYVPCHIRQ
VER-TY01   ASNLWFNCQGEFFYCKMDWFLNYLNNKTWDADHNFCSSKKKGHAPGPCVQRTYVACHIRS
YU2       IVTHSFNCGGEFFYCNSTQLFTWNDTIRKLNN-------TGRNITLPCRIKQ
HXB2      IVTHSFNCGGEFFYCNSTQLFNSTWFNSTWSTEGSNNTE----GSDTITLPCRIKQ
              * **** ** **                                  *

V4
          ΔΔΔΔΔΔ
7312A     LGDYKLIEVTPIGFAPTSEKRYSS-TPGRHKR
UC1       LGDYKLVEITPIGFAPTEIKRYSS-TTPRNKR
MAC239    LGDYKLVEITPIGLAPTDVKRYTTGGTSRNKR
VER-TY01   LGRYKLVEITPIGFAPTEVRRYRYTG-GHERQKR
YU2       LYKYKVVKIEPLGVAPTKAKRRVV----QREKR
HXB2      LYKYKVVKIEPLGVAPTKAKRRVV----QREKR
          *    *       * *           *
                            510
                434

SEQUENCE IDENTITY
▨ BRIDGING SHEET    17/31  (55%)
○ CHEMOKING RECEPTOR  8/16  (50%)
△ CD4 BINDING SITE   7/26  (27%)
* OVERALL gp120    111/451 (25%)
```

FIG. 1B

HIV-2 Alignments with Bridging Sheet, Variable Loops, and AA434 Indicated

```
7312A     ----------MCGKNLLFVASLLASAY--LIYCTKYVTVFYGVPVWRNASIPLFCATKN--
UC1       ----------MAHTSNHLFILLLLISVYGFLGHKKNYVTVFYGIPAWRNATVPLFCATTN--
UC2       ----------MEPGRNQLLAVILLTSAC--LIYCKQYVTVFYGVPVWRNASIPLFCATKN--
ROD-B.14  ----------MMNQLLIAILLASAC--LVYCTQYVTVFYGVPTWKNATIPLFCATRN--
HXB2      MRVKEKYQHLWRWGWRWGTMLLGMLMICSATEKLWVTVYYGVPVWKEATTTLFCASDAKA
                    .    **       .:***:**:*.*:;*:  .****:

7312A     -----RDTWGTIQCLPDNDDYQEIALN-VTEAFDAWNNTVTEQAVEDVWSLFETSIKPCV
UC1       -----RDTWGTVQCLPDNGDYTEISVN-ITEAFDAWNNTVTEQAVDDVWSLFETSIKPCV
UC2       -----RDTWGTIQCLPDNDDYQEIPLN-VTEAFDAWDNTVTEQAIEDVWRLFETSIKPCV
ROD-B.14  -----RDTWGTIQCLPDNDDYQEITLN-VTEAFDAWNNTVTEQAIEDVWHLFETSIKPCV
HXB2      YDTEVHNVWATHACVPTDPNPQEVVLVNVTENFNMWKNDMVEQMHEDIISLWDQSLKPCV
          ::.*.*  *:*  : :  *: :  :**.*: *.*  :** :*: *:: *:****
                                                      V1/V2

7312A     KLTPLCVAMSCNSTTATTTPPSTTNNTTTTEPTTGG--PEINETFPCMRTDNCTGLGEEE
UC1       KLTPLCVAMRCN----NTGTNTTTKPITTPITTTKPSENLLNDTSPCIKNDTCPGIGLEN
UC2       KLTPLCVAMNCNPVTGNN-TNATAKPTAARPTTNPSYLTIINESSTCVGADNCTGLGDEG
ROD-B.14  KLTPLCVAMKCSSTESSIGNNTTSKSTSTTTTTPTDQEQEISEDTPCARADNCSGLGKEE
HXB2      KLTPLCVSLKCTDLKNDTNTNSSSGRMIMEK-----------------------------GE
          *******:: *.                                        :::
                    V1/V2 (cont'd)

7312A     MVDCQFNMTGLERDKTKQYSETWYSKDVVCESNNASDGRDRCYMNHCNTSVITESCDKHY
UC1       TVDCYFNMTGLRRDEKKQYKDTWYEKDLECNGNSTS---TICYMRTCNTSVIQESCDKHY
UC2       MVNCKFNMTGLEQDKIKGYTDTWYSDDVVCDSTNKTGINTTCYMRHCNTSVIKESCDKHY
ROD-B.14  TINCQFNMTGLERDKKKQYNETWYSKDVVCKTNNST-NQTQCYMNHCNTSVITESCDKHY
HXB2      IKNCSFNISTSIRGKVQKEYAFFYKLDIIPIDNDTT----SYKLTSCNTSVITQACPKVS
          :* **:: :..  :    :*. *:    ..  :      : ****** ::* *

7312A     WDAIRFRYCAPPGFALLRCNDTNYSGFMPNCSKVVVSSCTRMMETQTSTWFGFNGTRAEN
UC1       WDSLRFRYCAPPGYALLRCNDTNYSGFMPKCSKVVVSSCTRMMETQTSTWFGFNGTRTEN
UC2       WDSMKFRYCTPPGYALLRCNDTNYSGFAPNCSKVVAASCTRMMETQTSTWFGFNGTRAEN
ROD-B.14  WDAIRFRYCAPPGYALLRCNDTNYSGFAPNCSKVVASTCTRMMETQTSTWFGFNGTRAEN
HXB2      FEPIPIHYCAPAGFAILKCNNKTFNGTGP-CTNVSTVQCTHGIRPVVSTQLLLNGSLAEE
          ::..: ::**:*.*:*:*:**:...:.*  *  *.:*  **: :.. ** : :**: :*:
                                                   V3

7312A     RTYMYWHSK-DNRTIISLNKYYNLTIHCKRPGNKTVVPITLMSGLVFHSQ--PINKRPRQ
UC1       RTYMYWHSK-DNRTIISLNKYYNLTMHCRRPGNKTVIPITIMSGLNFHSQ--PLNTRPRQ
UC2       RTYIYWHGR-DNRTIISLNKHYNLTMHCKRPGNKTVVPITLMSGHRFHSQ-AVINKKPRQ
ROD-B.14  RTYIYWHGR-DNRTIISLNKYYNLSLHCKRPGNKTVKQIMLMSGHVFHSHYKPINKRPRQ
HXB2      EVVIRSVNFTDNAKTIIVQLNTSVEINCTRPNNNTRKRIRIQRGPGRAFVTIGKIGNMRQ
          ..  :  . ** .  * ::  .: ::* **.*:*   *  *       .  **

7312A     AWCWFK-GEWREAMQEVKQTLIKHPRYKGTNDTRNITFTKPGTGSDPEVAYMWTNCRGEF
UC1       AWCWFK-GNWIEAIREVKETIIKHPRYKGTNNTERIRLVGPSAGSDPEVRHMWTNCRGEF
UC2       AWCWFK-GNWKGAMQEVKQTLAGHPRYKGTNDTSKINFVKPGVGSDPEVTYMWTNCRGEF
ROD-B.14  AWCWFK-GKWKDAMQEVKETLAKHPRYRGTNDTRNISFAAPGKGSDPEVAYMWTNCRGEF
HXB2      AHCNISRAKWNNTLKQIASKLREQFGNN------KTIIFKQSSGGDPEIVTHSFNCGGEF
          * * :..:*  ::::: ..: :  .     . :  . *.***: ** ***
```

FROM FIG. 3A

|         | V4 | 434 |

```
7312A    LYCNMTWFLN----------WVENRTGQTQHNYAPCHIKQIINTWHKVGKNVITPPREGQ
UC1      FYCNMTWFLN----------WVENRTGTTQKNYVTCHIKQIYNTWHKVGKYYVIPPREGT
UC2      FYCNMTWFLN----------WVENRTSQKQRNYAPCHIRQIINTWHRVGQIVYIPPREGE
ROD-B.14 FYCNMTWFLN----------WIENKT---HRNYAPCHIRQIINTWHRVGINVYIPPREGE
HXB2     FYCNSTQLFNSTWFNSTWSTEGSNNTEGSDTITLPCRIKQIINMWQKVGKAMYAPPISGQ
         :*** *::*                   .*.*  .  .*:*;**:* *:***.:* **.*

7312A    LTCNSTVTSLIANIDVD--VGNNRTNITFSAEVAELYRLELGDYKLIEVTPIGFAPTSEK
UC1      LSCNSSVTSLIANIDVYYDGNDTKTNITMSAEVGELYRLELGDYKLVEITPIGFAPTEIK
UC2      LTCNSTVTSIIANIDT----DGN-QTNITFSAEVAELYRLELGDYKLIEITPIGFAPTSEK
ROD-B.14 LSCNSTVTSIIANIDW---QNNNQTNITFSAEVAELYRLELGDYKLVEITPIGFAPTKEK
HXB2     IRCSSNITGLLLTRDGGNSNNESEIFRPGGGDMRDNWRSELYKYKVVKIEPLGVAPTKAK
         : *.*.:*.:: . *     .: .  . ..:: : :* ** .**:::: *:*.***. *

7312A    RYSSTPGRHKRGVFVLGFLGFLTTAGAAMGAASLTLSAQSRTLLAGIVQQQQQLLDVVKR
UC1      RYSSTTPRNKRGVMVLGFLGLLAMAGSAMGATSLTLSAQSRTLLAGIVQQQQQLLDVVKR
UC2      RYSSAPARNKRGVFVLGLLGFLATAGSAMGAASLTLSAQSRTLLAGIVQQQQQLLDIVKR
ROD-B.14 RYSSAHGRHTRGVFVLGFLGFLATAGSAMGAASLTLSAQSRTLLTGIVQQQQQLLDVVKR
HXB2     RRVVQREKRAVGIGAL-FLGFLGAAGSTMGAASMTLTVQARQLLSGIVQQQNNLLRAIEA
         *    :.  *: .* :*:** **:***:*:**:.*:* *****:*::**  ::

7312A    QQEMLRLTVWGTKNLQARVTAIEKYLKDQAQLNSWGCAFRQVCHTTVPW----VNDSLTP
UC1      QQELLRLTVWGTKNLQTRVTAIEKYLKDQALLNSWGCAFRQVCHTTVPW----PNETLTP
UC2      QQELLRLTVWGTKNLQARVTAIEKYLKDQAQLNSWGCTFRQVCHTTVPW----VNDSLTP
ROD-B.14 QQELLRLTVWGTKNLQARVTAIEKYLQDQARLNSWGCAFRQVCHTTVPW----VNDSLAP
HXB2     QQHLLQLTVWGIKQLQARILAVERYLKDQQLLGIWGCSGKLICTTAVPWNASWSNKSLEQ
         **.:*;***** *:**:*;  **:;**;** *,  ***  :  :* *;***   *.:*

7312A    DWDNMTWQQWEKQIRDLEANISESLEQAQIQQEKNMYELQKLNSWDVFGNWFDLASWVKY
UC1      DWENMTWQQWEKRVNFLDANITALLEEAQIQQERNMYELQKLNSWDVFGNWFDFTSWMAY
UC2      RWNNMTWQEWEKQVRYLEANISQSLEEAQIQQEKNMYELQKLNSWDVFGNWFDLTSWIKY
ROD-B.14 DWDNMTWQEWEKQVRYLEANISKSLEQAQIQQEKNMYELQKLNSWDIFGNWFDLTSWVKY
HXB2     IWNHTTWMEWDREINNYTSLIHSLIEESQNQQEKNEQELLELDKWASLWNWFNITNWLWY
         *:: ** :*::.,.   : *  :*:;* ***:* ** :*:.*   : *****:;:.*; *

7312A    IQYGVYIVVGIVALRVIIYVVQMIGRLRRGYRPVFSSPPGYFQQIRIHKDQEQPANEETE
UC1      IRLGLYVVAGLIVLRIVIYIMQMLARLRKGYRPVFSSPPSYTQQIPIRKHRGQPANEETE
UC2      IQYGVYIVVGIIALRIAIYVVQLLSRFRKGYRPVFSSPPGYLQQIHIHTDRGQPANEETE
ROD-B.14 IQYGVLIIVAVIALRIVIYVVQMLSRLRKGYRPVFSSPPGYIQQIHIHKDRGQPANEETE
HXB2     IKLFIMIVGGLVGLRIVFAVLSIVNRVRQGYSPLS--------FQTHLPTPRGDRPEGIE
         *:  :  ::..:: ** :**  :  :::..::  *,*:** *:      *  ;.:  * *

7312A    EGGGNDGGYRSWPWQIEYIHFLIRQLRNLLIWLYDGCRTLLLKT--------FQTLQPALQ
UC1      DEGGNEGAYRSWPWQIEYAHFLIRQLRNLLIWLYNGCRNLLLKT--------SQILQPALQ
UC2      GDAGDASGYDFWPWPINYIQLLIHLLTRLLTGLYSICRDLLSANSPTRRLISQNLTAIRD
ROD-B.14 EDGGSNGGDRYWP-----------------------------------------------
HXB2     EEGGERDRDRSIRLVNGSLALIWDDLRSLCLFSYHRLRDLLLIVTR---IVELLGRRGWE
         .*, .

7312A    PLRLLFAYLQYGIGWFQEAVQAAAGATGETLASTGRTLWEALRRTARGIIAVPRRIRQGL
UC1      PLRLSLAYLQYGISWFQEAIQAATRAARETLANTGRALWKALRRTAEAIIAIPRRIRQGL
UC2      WLRLKAAYLQYGCEWIQEAFQAIARTARETLAGAWRGLCKAVQRIGRGILAVPRRIRQGA
ROD-B.14 ------------------------------------------------------------
HXB2     ALKYWWNLLQYWSQELKNSAVSLLNATAIAVAEGTDRVIEVVQGACRAIRHIPRRIRQGL

7312A    ELALL
UC1      ELALL
UC2      EIALL
ROD-B.14 -----
HXB2     ERILL
```

FIG. 3B gp41

| | |
|---|---|
| ST | KRGVFVLG-FLGFLTTAGAAMGAASLTLSAQSRTLLAGIVQQQQQLLDVVKRQQEMLRLT |
| 7312A | KRGVFVLG-FLGFLTTAGAAMGAASLTLSAQSRTLLAGIVQQQQQLLDVVKRQQEMLRLT |
| UC1 | KRGVMVLG-FLGLLAMAGSAMGATSLTLSAQSRTLLAGIVQQQQQLLDVVKRQQELLRLT |
| YU-2 | KRAVGLGALFLGFLGAAGSTMGAASITLTVQARQLLSGIVQQQNNLLRAIEAQQHLLQLT |
| HXB-2c | KRAVGIGALFLGFLGAAGSTMGAASMTLTVQARQLLSGIVQQQNNLLRAIEAQQHLLQLT |
| | **.*  :  .   ****:*    :**:*.:.*   *:*****.:::  .*::.*:.:.**  |

| | |
|---|---|
| ST | VWGTKNLQARVTAIEKYLKDQAQLNSWGCAFRQVCHTTVPW-----VNDTLTPDWNNMTWQ |
| 7312A | VWGTKNLQARVTAIEKYLKDQAQLNSWGCAFRQVCHTTVPW-----VNDSLTPDWDNMTWQ |
| UC1 | VWGTKNLQTRVTAIEKYLKDQALLNSWGCAFRQVCHTTVPW-----PNETLTPDWENMTWQ |
| YU-2 | VWGIKQLQARVLAVERYLRDQQLLGIWGCSGKLICTTTVPWNTSWSNKSLNEIWDNMTWM |
| HXB-2c | VWGIKQLQARILAVERYLKDQQLLGIWGCSGKLICTTAVPWNASWSNKSLEQIWNHTTWM |
| | *** :*:** . * .**: : .:.   : *.:  *   *    :    * * |

| | |
|---|---|
| ST | EWEQRIRNLEANISESLEQAQIQQEKNMYELQKLNSWDVFGNWFDLTSWIKYIQYGVYIV |
| 7312A | QWEKQIRDLEANISESLEQAQIQQEKNMYELQKLNSWDVFGNWFDLASWVKYIQYGVYIV |
| UC1 | QWEKRVNFLDANITALLEEAQIQQERNMYELQKLNSWDVFGNWFDFTSWMAYIRLGLYVV |
| YU-2 | KWEREIDNYTHIIYSLIEQSNQQEKNEQELLALDKWASLWNWFDITKWLWYIKIFIMIV |
| HXB-2c | EWDREINNYTSLIHSLIEESQNQQEKNEQELLELDKWASLWNWFNITNWLWYIKLFIMIV |
| | :*:: .::   *  **: .: **:* :*  * ****  **: : *:  *:*  :.:: |

FROM FIG. 4A

```
ST      VGIIVLRIVIYVVQMLSRLRKGYRPVFSSPPAYFQQIHIHKDREQPAREETEEDVGNSVG
7312A   VGIVALRVIIYVVQMIGRLRRGYRPVFSSPPGYFQQIRIHKDQEQPANEETEEGGNDGG
UC1     AGLIVLRIVIYIMQMLARLRKGYRPVFSSPPSYTQQIPIRKHRGQPANEETEDEGGNEGA
YU-2    GGLIGLRIVFVVLSIVNRVRQGY-----SPLSFQTHLPAQRGPDRP---DGIEEEGGERDR
HXB-2c  GGLVGLRIVFAVLSIVNRVRQGY-----SPLSFQTHLPTPRGPDRP---EGIEEEGGERDR
        *:: **::: ::..:: *:*:*** ..         :   .:          *: .

ST      DNWWPWPIRYIHFLIRQLIRLLNRLYNICRDLLLSRSFQTLQLISQSLRRALTAVRDWLRF
7312A   YRSWPWQIEYIHFLIRQLRNLLIWLYDGCRTLLLIKTFQTLQPALQPLR-------LLF
UC1     YRSWPWQIEYAHFLIRQLRNLLIWLYNGCRNLLLLKTSQILQPALQPLR----------L
YU-2    DRSGPLVDGFLAIIWDLRSLCLFSYHRLRDLLLIVTRIVELLGRRGWG------VLKY
HXB-2c  DRSIRLVNGSIALIWDDLRSLCLFSYHRLRDLLLIVTRIVELLGRRGWE------ALKY
         ..    :*  *  :: *  * *    .   * :   :  :::  :

ST      NTAYLQYGGEWIQEAFRAFARATGETLTNAWRGFWGTLGQIGRGILAVPRRIRQGAEIAL
7312A   ---AYLQYGIGWFQEAVQAAAAGATGETLASTGRTLWEALRRTARGILAVPRRIRQGLELAL
UC1     SLAYLQYGISWFQEAIQYGISWFQEAIQAATRAARETLANTGRALWKALRRTAEAIIAIPRRIRQGLELAL
YU-2    WWNLLQYWIQELKNSAVSLLNATAIAVAEGTDRVIEILQRAFRAVLHIPVRIRQGLERAL
HXB-2c  WWNLLQYWSQELKNSAVSLLNATAIAVAEGTDRVIEVVQGACRAIRHIPRRIRQGLERIL
           .  *  *.  ..       .  ::      .:*  ***** *

ST      L
7312A   L
UC1     L
YU-2    L
HXB-2c  *
```

FIG. 4B

```
7312A     ...QIQQEKNMYELQKLNSWDVFGNWFDLASWVKYIQYGVYIV...
7312A-C1  ...QIQQEKNMYELEALDKWASEWNMFDLASWVKYIQYGVYIV...
7312A-C2  ...QIQQEKNMYELEALDKWASEWNMFDLKYMLWVKYKYGVYIV...
7312A-C3  ...QIQQEKNMYELEALDKWASEWNWFDLASWVKYIQYGVYIV...
7312A-C4  ...QIQQEKNMYELQKLNSWDVFGNWFDLEAMLWVKEYGVYIV...
7312A-C5  ...QIQQEKNMYELQKLNSWDVFGNWFDEELSWVKYIQYGVYIV...
7312A-C6  ...QIQQEKNMYELQALDKWAVFGNWFDLASWVKYIQYGVYIV...
```

FIG. 7

```
ST      KRGVFVLG-FLGFLTTAGAAMGAASLTLSAQSRTLLAGIVQQQQQLLDVVKRQQEMLRLT
7312A   KRGVFVLG-FLGFLTTAGAAMGAASLTLSAQSRTLLAGIVQQQQQLLDVVKRQQEMLRLT
UC1     KRGVMVLG-FLGLLAMAGSAMGATSLTLSAQSRTLLAGIVQQQQQLLDVVKRQQELLRLT
YU-2    KRAVGLGALFLGFLGAAGSTMGAASITLTVQARQLLSGIVQQQNNLLRAIEAQQHLLQLT
        **.*  :  . ***:* **::***:*:**:.*:* **:******::**  .:: **.:*:**

ST      VWGTKNLQARVTAIEKYLKDQAQLNSWGCAFRQVCHTTVPW----VNDTLTPDWNNMTWQ
7312A   VWGTKNLQARVTAIEKYLKDQAQLNSWGCAFRQVCHTTVPW----VNDSLTPDWDNMTWQ
UC1     VWGTKNLQTRVTAIEKYLKDQALLNSWGCAFRQVCHTTVPW----PNETLTPDWENMTWQ
YU-2    VWGIKQLQARVLAVERYLRDQQLLGIWGCSGKLICTTTVPWNTSWSNKSLNEIWDNMTWM
        *** *:**:** *:*:**:** *. ***:  : :* ***** *..*. *:****

ST      EWEQRIRNLEANISESLEQAQIQQEKNMYELQKLNSWDVFG<u>NWFDLT</u>SWIKYIQYGVYIV
7312A   QWEKQIRDLEANISESLEQAQIQQEKNMYELQKLNSWDVFG<u>NWFDLA</u>SWVKYIQYGVYIV
UC1     QWEKRVNFLDANITALLEEAQIQQERNMYELQKLNSWDVFG<u>NWFDFT</u>SWMAYIRLGLYVV
YU-2    KWEREIDNYTHIIYSLIEQSQNQQEKNEQ<u>ELLALDKWAS</u>L<u>WNWFDIT</u>KWLWYIKIFIMIV
        :**:.: * :*:*: ***:* **  *:.* : ****:::.*: **:  :  :*

ST      VGIIVLRIVIYVVQMLSRLRKGYRPVFSSPPAYFQQIHIHKDREQPAREETEEDVGNSVG
7312A   VGIVALRVIIYVVQMIGRLRRGYRPVFSSPPGYFQQIRIHKDQEQPANEETEEGGGNDGG
UC1     AGLIVLRIVIYIMQMLARLRKGYRPVFSSPPSYTQQIPIRKHRGQPANEETEDEGGNEGA
YU-2    GGLIGLRIVFVVLSIVNRVRQGY-----SPLSFQTHLPAQRGPDRPD--GIEEEGGERDR
        *::  **::: ::.:: *:*:** **    .:  ::  ::   :* *:  *:

ST      DNWWPWPIRYIHFLIRQLIRLLNRLYNICRDLLSRSFQTLQLISQSLRRALTAVRDWLRF
7312A   YRSWPWQIEYIHFLIRQLRNLLIWLYDGCRTLLLKTFQTLQPALQPLR--------LLF
UC1     YRSWPWQIEYAHFLIRQLRNLLIWLYNGCRNLLLKTSQILQPALQPLR-----------L
YU-2    DRSGPLVDGFLAIIWVDLRSLCLFSYHRLRDLLLIVTRIVELLGRRGWG-------VLKY
          . *    :  ::  :* * * *.  *  **    :  ::  :

ST      NTAYLQYGGEWIQEAFRAFARATGETLTNAWRGFWGTLGQIGRGILAVPRRIRQGAEIAL
7312A   --AYLQYGIGWFQEAVQAAAAGATGETLASTGRTLWEALRRTARGIIAVPRRIRQGLELAL
UC1     SLAYLQYGISWFQEAIQAATRAARETLANTGRALWKALRRTAEAIIAIPRRIRQGLELAL
YU-2    WWNLLQYWIQELKNSAVSLLNATAIAVAEGTDRVIEILQRAFRAVLHIPVRIRQGLERAL
        ***  ::::  :  *:  :::.  .  *   : .  ..::  :* ***** * **
```

FIG. 8

SEQUENCE LISTING

<160> NUMBER OF SEQ ID NOS: 39

<210> SEQ ID NO 1
<211> LENGTH: 365
<212> TYPE: PRT
<213> ORGANISM: Homo sapiens

<400> SEQUENCE: 1

Lys Lys Val Val Leu Gly Lys Lys Gly Asp Thr Val Glu Leu Thr Cys
 1               5                   10                  15

```
Thr Ala Ser Gln Lys Lys Ser Ile Gln Phe His Trp Lys Asn Ser Asn
             20                  25                  30

Gln Ile Lys Ile Leu Gly Asn Gln Gly Ser Phe Leu Thr Lys Gly Pro
             35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Glu Asp Gln Lys Glu Glu Val Gln Leu Leu
                 85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
            195                 200                 205

Gly Ser Gly Glu Leu Trp Trp Gln Ala Glu Arg Ala Ser Ser Ser Lys
210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
            275                 280                 285

Leu Val Val Met Arg Ala Thr Gln Leu Gln Lys Asn Leu Thr Cys Glu
290                 295                 300

Val Trp Gly Pro Thr Ser Pro Lys Leu Met Leu Ser Leu Lys Leu Glu
305                 310                 315                 320

Asn Lys Glu Ala Lys Val Ser Lys Arg Glu Lys Ala Val Trp Val Leu
                325                 330                 335

Asn Pro Glu Ala Gly Met Trp Gln Cys Leu Leu Ser Asp Ser Gly Gln
            340                 345                 350

Val Leu Leu Glu Ser Asn Ile Lys Val Leu Pro Thr Trp
            355                 360                 365

<210> SEQ ID NO 2
<211> LENGTH: 857
<212> TYPE: PRT
<213> ORGANISM: Human immunodeficiency virus

<400> SEQUENCE: 2

Met Cys Gly Lys Asn Leu Leu Phe Val Ala Ser Leu Leu Ala Ser Ala
 1               5                  10                  15

Tyr Leu Ile Tyr Cys Thr Lys Tyr Val Thr Val Phe Tyr Gly Val Pro
             20                  25                  30
```

-continued

Val Trp Arg Asn Ala Ser Ile Pro Leu Phe Cys Ala Thr Lys Asn Arg
         35                  40                  45

Asp Thr Trp Gly Thr Ile Gln Cys Leu Pro Asp Asn Asp Tyr Gln
 50                  55                  60

Glu Ile Ala Leu Asn Val Thr Glu Ala Phe Asp Ala Trp Asn Asn Thr
 65                  70                  75                  80

Val Thr Glu Gln Ala Val Glu Asp Val Trp Ser Leu Phe Glu Thr Ser
                 85                  90                  95

Ile Lys Pro Cys Val Lys Leu Thr Pro Leu Cys Val Ala Met Ser Cys
             100                 105                 110

Asn Ser Thr Thr Ala Thr Thr Thr Pro Pro Ser Thr Thr Asn Asn Thr
         115                 120                 125

Thr Thr Thr Glu Pro Thr Thr Gly Gly Pro Glu Ile Asn Glu Thr Phe
     130                 135                 140

Pro Cys Met Arg Thr Asp Asn Cys Thr Gly Leu Gly Glu Glu Met
145                 150                 155                 160

Val Asp Cys Gln Phe Asn Met Thr Gly Leu Glu Arg Asp Lys Thr Lys
                 165                 170                 175

Gln Tyr Ser Glu Thr Trp Tyr Ser Lys Asp Val Val Cys Glu Ser Asn
             180                 185                 190

Asn Ala Ser Asp Gly Arg Asp Arg Cys Tyr Met Asn His Cys Asn Thr
         195                 200                 205

Ser Val Ile Thr Glu Ser Cys Asp Lys His Tyr Trp Asp Ala Ile Arg
     210                 215                 220

Phe Arg Tyr Cys Ala Pro Pro Gly Phe Ala Leu Leu Arg Cys Asn Asp
225                 230                 235                 240

Thr Asn Tyr Ser Gly Phe Met Pro Asn Cys Ser Lys Val Val Ser
                 245                 250                 255

Ser Cys Thr Arg Met Met Glu Thr Gln Thr Ser Thr Trp Phe Gly Phe
             260                 265                 270

Asn Gly Thr Arg Ala Glu Asn Arg Thr Tyr Met Tyr Trp His Ser Lys
         275                 280                 285

Asp Asn Arg Thr Ile Ile Ser Leu Asn Lys Tyr Tyr Asn Leu Thr Ile
     290                 295                 300

His Cys Lys Arg Pro Gly Asn Lys Thr Val Val Pro Ile Thr Leu Met
305                 310                 315                 320

Ser Gly Leu Val Phe His Ser Gln Pro Ile Asn Lys Arg Pro Arg Gln
                 325                 330                 335

Ala Trp Cys Trp Phe Lys Gly Glu Trp Arg Glu Ala Met Gln Glu Val
             340                 345                 350

Lys Gln Thr Leu Ile Lys His Pro Arg Tyr Lys Gly Thr Asn Asp Thr
         355                 360                 365

Arg Asn Ile Thr Phe Thr Lys Pro Gly Thr Gly Ser Asp Pro Glu Val
     370                 375                 380

Ala Tyr Met Trp Thr Asn Cys Arg Gly Glu Phe Leu Tyr Cys Asn Met
385                 390                 395                 400

Thr Trp Phe Leu Asn Trp Val Glu Asn Arg Thr Gly Gln Thr Gln His
                 405                 410                 415

Asn Tyr Ala Pro Cys His Ile Lys Gln Ile Ile Asn Thr Trp His Lys
             420                 425                 430

Val Gly Lys Asn Val Tyr Leu Pro Pro Arg Glu Gly Gln Leu Thr Cys
         435                 440                 445

Asn Ser Thr Val Thr Ser Leu Ile Ala Asn Ile Asp Val Asp Val Gly

-continued

```
                450                 455                 460
Asn Asn Arg Thr Asn Ile Thr Phe Ser Ala Glu Val Ala Glu Leu Tyr
465                 470                 475                 480

Arg Leu Glu Leu Gly Asp Tyr Lys Leu Ile Glu Val Thr Pro Ile Gly
                485                 490                 495

Phe Ala Pro Thr Ser Glu Lys Arg Tyr Ser Ser Thr Pro Gly Arg His
                500                 505                 510

Lys Arg Gly Val Phe Val Leu Gly Phe Leu Gly Phe Leu Thr Thr Ala
                515                 520                 525

Gly Ala Ala Met Gly Ala Ala Ser Leu Thr Leu Ser Ala Gln Ser Arg
530                 535                 540

Thr Leu Leu Ala Gly Ile Val Gln Gln Gln Gln Leu Leu Asp Val
545                 550                 555                 560

Val Lys Arg Gln Gln Glu Met Leu Arg Leu Thr Val Trp Gly Thr Lys
                565                 570                 575

Asn Leu Gln Ala Arg Val Thr Ala Ile Glu Lys Tyr Leu Lys Asp Gln
                580                 585                 590

Ala Gln Leu Asn Ser Trp Gly Cys Ala Phe Arg Gln Val Cys His Thr
                595                 600                 605

Thr Val Pro Trp Val Asn Asp Ser Leu Thr Pro Asp Trp Asp Asn Met
610                 615                 620

Thr Trp Gln Gln Trp Glu Lys Gln Ile Arg Asp Leu Glu Ala Asn Ile
625                 630                 635                 640

Ser Glu Ser Leu Glu Gln Ala Gln Ile Gln Gln Glu Lys Asn Met Tyr
                645                 650                 655

Glu Leu Gln Lys Leu Asn Ser Trp Asp Val Phe Gly Asn Trp Phe Asp
                660                 665                 670

Leu Ala Ser Trp Val Lys Tyr Ile Gln Tyr Gly Val Tyr Ile Val Val
                675                 680                 685

Gly Ile Val Ala Leu Arg Val Ile Ile Tyr Val Val Gln Met Ile Gly
                690                 695                 700

Arg Leu Arg Arg Gly Tyr Arg Pro Val Phe Ser Ser Pro Gly Tyr
705                 710                 715                 720

Phe Gln Gln Ile Arg Ile His Lys Asp Gln Glu Gln Pro Ala Asn Glu
                725                 730                 735

Glu Thr Glu Glu Gly Gly Gly Asn Asp Gly Gly Tyr Arg Ser Trp Pro
                740                 745                 750

Trp Gln Ile Glu Tyr Ile His Phe Leu Ile Arg Gln Leu Arg Asn Leu
                755                 760                 765

Leu Ile Trp Leu Tyr Asp Gly Cys Arg Thr Leu Leu Leu Lys Thr Phe
770                 775                 780

Gln Thr Leu Gln Pro Ala Leu Gln Pro Leu Arg Leu Leu Phe Ala Tyr
785                 790                 795                 800

Leu Gln Tyr Gly Ile Gly Trp Phe Gln Glu Ala Val Gln Ala Ala Ala
                805                 810                 815

Gly Ala Thr Gly Glu Thr Leu Ala Ser Thr Gly Arg Thr Leu Trp Glu
                820                 825                 830

Ala Leu Arg Arg Thr Ala Arg Gly Ile Ile Ala Val Pro Arg Arg Ile
                835                 840                 845

Arg Gln Gly Leu Glu Leu Ala Leu Leu
850                 855

<210> SEQ ID NO 3
<211> LENGTH: 779
```

<212> TYPE: PRT
<213> ORGANISM: Simian immunodeficiency virus

<400> SEQUENCE: 3

```
Met Arg Cys Asn Lys Ser Glu Thr Asp Arg Trp Gly Leu Thr Gly Thr
 1               5                  10                  15

Pro Ala Pro Thr Thr Thr Gln Thr Thr Thr Gln Ala Ser Thr Thr
            20                  25                  30

Pro Thr Ser Pro Ile Thr Ala Lys Val Val Asn Asp Ser Asp Pro Cys
            35                  40                  45

Ile Lys Ile Asn Asn Cys Thr Gly Leu Glu Gln Glu Pro Met Val Ser
 50                  55                  60

Cys Lys Phe Asn Met Thr Gly Leu Lys Arg Asp Lys Lys Arg Glu Tyr
 65                  70                  75                  80

Asn Glu Thr Trp Tyr Ser Arg Asp Leu Val Cys Glu Gln Asn Asn Asn
                85                  90                  95

Glu Thr Asp Ser Lys Cys Tyr Met Asn His Cys Asn Thr Ser Val Ile
            100                 105                 110

Gln Glu Ser Cys Asp Lys His Tyr Trp Asp Ala Ile Arg Phe Arg Tyr
            115                 120                 125

Cys Ala Pro Pro Gly Tyr Ala Leu Leu Arg Cys Asn Asp Ser Asn Tyr
130                 135                 140

Ser Gly Phe Ala Pro Asn Cys Thr Lys Val Val Thr Ser Cys Thr
145                 150                 155                 160

Arg Met Met Glu Thr Gln Thr Ser Thr Trp Phe Gly Phe Asn Gly Thr
                165                 170                 175

Arg Ala Glu Asn Arg Thr Tyr Ile Tyr Trp His Gly Arg Ser Asn Arg
            180                 185                 190

Thr Ile Ile Ser Leu Asn Lys Tyr Tyr Asn Leu Thr Met Arg Cys Arg
        195                 200                 205

Arg Pro Gly Asn Lys Thr Val Leu Pro Val Thr Ile Met Ser Gly Leu
    210                 215                 220

Val Phe His Ser Gln Pro Ile Asn Glu Arg Pro Lys Gln Ala Trp Cys
225                 230                 235                 240

Trp Phe Gly Gly Glu Trp Lys Lys Ala Ile Gln Glu Val Lys Glu Thr
                245                 250                 255

Leu Val Lys His Pro Arg Tyr Thr Gly Thr Asn Lys Thr Glu Gln Ile
            260                 265                 270

Lys Leu Thr Ala Pro Gly Gly Gly Asp Pro Glu Val Thr Phe Met Trp
        275                 280                 285

Thr Asn Cys Arg Gly Glu Phe Leu Tyr Cys Lys Met Asn Trp Phe Leu
    290                 295                 300

Asn Trp Val Glu Glu Ile Gln Asn Gly Ser Arg Trp Thr Ser Gln Asn
305                 310                 315                 320

Gln Lys Glu Arg Gln Arg Asn Tyr Val Pro Cys His Ile Arg Gln
                325                 330                 335

Ile Ile Asn Thr Trp His Lys Val Gly Lys Asn Val Tyr Leu Pro Pro
            340                 345                 350

Arg Glu Gly Asp Leu Thr Cys Asn Ser Thr Val Thr Ser Leu Ile Ala
        355                 360                 365

Glu Ile Asp Trp Ile Asn Gly Asn Glu Thr Asn Ile Thr Met Ser Ala
    370                 375                 380

Glu Val Ala Glu Leu Tyr Arg Leu Glu Leu Gly Asp Tyr Lys Leu Val
385                 390                 395                 400
```

```
Glu Ile Thr Pro Ile Ala Phe Ala Pro Thr Ser Val Lys Arg Tyr Thr
                405                 410                 415
Thr Thr Gly Ala Ser Arg Asn Lys Arg Gly Val Phe Val Leu Gly Phe
            420                 425                 430
Leu Gly Phe Leu Ala Thr Ala Gly Ser Ala Met Gly Ala Ala Ser Val
        435                 440                 445
Thr Leu Ser Ala Gln Ser Arg Thr Leu Leu Ala Gly Ile Val Gln Gln
    450                 455                 460
Gln Gln Gln Leu Leu Asp Val Val Lys Arg Gln Gln Glu Leu Leu Arg
465                 470                 475                 480
Leu Thr Val Trp Gly Ala Lys Asn Leu Gln Thr Arg Val Thr Ala Ile
                485                 490                 495
Glu Lys Tyr Leu Lys Asp Gln Ala Gln Leu Asn Ser Trp Gly Cys Ala
            500                 505                 510
Phe Arg Gln Val Cys His Thr Thr Val Pro Trp Pro Asn Asp Thr Leu
        515                 520                 525
Thr Pro Asn Trp Asn Asn Met Thr Trp Gln Glu Trp Glu Lys Gln Val
    530                 535                 540
Asn Phe Leu Glu Ala Asn Ile Thr Gln Ser Leu Glu Glu Ala Gln Ile
545                 550                 555                 560
Gln Gln Glu Lys Asn Thr Tyr Glu Leu Gln Lys Leu Asn Ser Trp Asp
                565                 570                 575
Ile Phe Gly Asn Trp Phe Asp Leu Thr Ser Trp Ile Lys Tyr Ile Gln
            580                 585                 590
Tyr Gly Val Leu Ile Val Leu Gly Val Ile Gly Leu Arg Ile Val Ile
        595                 600                 605
Tyr Val Val Gln Met Leu Ala Arg Leu Arg Gln Gly Tyr Arg Pro Val
    610                 615                 620
Phe Ser Ser Pro Pro Ala Tyr Val Gln Gln Ile Pro Ile Gln Thr Gly
625                 630                 635                 640
Gln Glu Leu Pro Thr Lys Glu Gly Glu Gly Asp Gly Gly Gly Gly Arg
                645                 650                 655
Gly Gly Asn Arg Ser Trp Pro Trp Gln Ile Glu Tyr Ile His Phe Leu
            660                 665                 670
Ile Arg Gln Leu Ile Arg Leu Leu Thr Trp Leu Phe Ser Ser Cys Arg
        675                 680                 685
Asp Trp Leu Leu Arg Asn Cys Gln Thr Leu Gln Pro Val Leu Gln Ser
    690                 695                 700
Leu Ser Arg Thr Leu Gln Arg Ala Arg Glu Val Ile Arg Val Gln Ile
705                 710                 715                 720
Ala Tyr Leu Gln Tyr Gly Trp Arg Tyr Leu Gln Glu Ala Ala Gln Ala
                725                 730                 735
Trp Trp Lys Phe Val Arg Glu Thr Leu Ala Ser Ala Trp Arg Asp Leu
            740                 745                 750
Trp Glu Thr Leu Gly Arg Val Gly Arg Gly Ile Leu Ala Ile Pro Arg
        755                 760                 765
Arg Ile Arg Gln Gly Leu Glu Leu Thr Leu Leu
    770                 775

<210> SEQ ID NO 4
<211> LENGTH: 768
<212> TYPE: PRT
<213> ORGANISM: Simian immunodeficiency virus

<400> SEQUENCE: 4
```

-continued

```
Met Thr Lys Phe Leu Gly Ile Phe Ile Val Leu Gly Ile Gly Ile Gly
 1               5                  10                  15
Ile Gly Ile Ser Thr Lys Gln Gln Trp Ile Thr Val Phe Tyr Gly Val
                 20                  25                  30
Pro Val Trp Lys Asn Ser Ser Val Gln Ala Phe Cys Met Thr Pro Thr
             35                  40                  45
Thr Arg Leu Trp Ala Thr Thr Asn Cys Ile Pro Asp Asp His Asp Tyr
     50                  55                  60
Thr Glu Val Pro Leu Asn Ile Thr Glu Pro Phe Glu Ala Trp Ala Asp
 65                  70                  75                  80
Arg Asn Pro Leu Val Ala Gln Ala Gly Ser Asn Ile His Leu Leu Phe
                 85                  90                  95
Glu Gln Thr Leu Lys Pro Cys Val Lys Leu Ser Pro Leu Cys Ile Lys
             100                 105                 110
Met Asn Cys Val Glu Leu Lys Gly Ser Ala Thr Ser Thr Pro Ala Thr
             115                 120                 125
Ser Thr Thr Ala Gly Thr Lys Leu Pro Cys Val Arg Asn Lys Thr Asp
     130                 135                 140
Ser Asn Leu Gln Ser Cys Asn Asp Thr Ile Ile Glu Lys Glu Met Asn
145                 150                 155                 160
Asp Glu Ala Ala Ser Asn Cys Thr Phe Ala Met Ala Gly Tyr Ile Arg
                 165                 170                 175
Asp Gln Lys Lys Asn Tyr Ser Val Val Trp Asn Asp Ala Glu Ile Phe
                 180                 185                 190
Cys Lys Arg Ser Thr Ser His Asn Gly Thr Lys Glu Cys Tyr Met Ile
             195                 200                 205
His Cys Asn Asp Ser Val Ile Lys Glu Ala Cys Asp Lys Thr Tyr Trp
             210                 215                 220
Asp Glu Leu Arg Leu Arg Tyr Cys Ala Pro Ala Gly Tyr Ala Leu Leu
225                 230                 235                 240
Lys Cys Asn Asp Trp Asp Tyr Ala Gly Phe Lys Pro Glu Cys Ser Asn
                 245                 250                 255
Val Ser Val Val His Cys Thr Thr Leu Met Asn Thr Thr Val Thr Thr
             260                 265                 270
Gly Leu Leu Leu Asn Gly Ser Tyr Ser Glu Asn Arg Thr Gln Ile Trp
             275                 280                 285
Gln Lys His Gly Val Ser Asn Asp Ser Val Leu Ile Leu Leu Asn Lys
     290                 295                 300
His Tyr Asn Leu Thr Val Thr Cys Lys Arg Pro Gly Asn Lys Thr Val
305                 310                 315                 320
Leu Pro Val Thr Ile Met Ala Gly Leu Val Phe His Ser Gln Lys Tyr
                 325                 330                 335
Asn Thr Arg Leu Arg Gln Ala Trp Cys His Phe Gln Gly Asn Trp Lys
             340                 345                 350
Gly Ala Trp Lys Glu Val Gln Glu Glu Ile Val Lys Leu Pro Lys Glu
             355                 360                 365
Arg Tyr Gln Gly Thr Asn Asp Thr Asn Lys Ile Phe Leu Gln Arg Gln
     370                 375                 380
Phe Gly Asp Pro Glu Ala Ala Asn Leu Trp Phe Asn Cys Gln Gly Glu
385                 390                 395                 400
Phe Phe Tyr Cys Lys Met Asp Trp Phe Leu Asn Tyr Leu Asn Asn Leu
                 405                 410                 415
Thr Val Asp Ala Asp His Asn His Cys Lys Asn Asn Ala Gly Lys Gly
             420                 425                 430
```

```
Arg Ser Pro Gly Pro Cys Val Gln Arg Thr Tyr Val Ala Cys His Ile
        435                 440                 445

Arg Ser Val Ile Asn Asp Trp Tyr Thr Ile Ser Lys Lys Thr Tyr Ala
        450                 455                 460

Pro Pro Arg Glu Gly His Leu Gln Cys Thr Ser Thr Val Thr Gly Met
465                 470                 475                 480

Thr Val Glu Leu Asn Tyr Asn Asn Gln Asn Arg Thr Asn Val Thr Leu
                485                 490                 495

Ser Pro Gln Ile Glu Thr Ile Trp Ala Ala Glu Leu Gly Arg Tyr Lys
        500                 505                 510

Leu Val Glu Ile Thr Pro Ile Gly Phe Ala Pro Thr Glu Val Arg Arg
        515                 520                 525

Tyr Thr Gly Gly Gln Glu Arg Gln Lys Arg Val Pro Phe Val Leu Gly
        530                 535                 540

Phe Leu Gly Phe Leu Gly Ala Ala Gly Thr Ala Met Gly Ala Ala Ala
545                 550                 555                 560

Thr Ala Leu Thr Val Gln Ser Gln His Leu Leu Ala Gly Ile Leu Gln
                565                 570                 575

Gln Gln Lys Asn Leu Leu Ala Ala Val Gly Ala Gln Gln Gln Met Leu
        580                 585                 590

Lys Leu Thr Ile Trp Gly Val Lys Asn Leu Asn Ala Arg Val Thr Ala
        595                 600                 605

Leu Glu Lys Tyr Leu Ala Asp Gln Ala Arg Leu Asn Ala Trp Gly Cys
        610                 615                 620

Ala Trp Lys Gln Val Cys His Thr Thr Val Pro Trp Thr Trp Asn Asn
625                 630                 635                 640

Thr Pro Glu Trp Asn Asn Met Thr Trp Leu Glu Trp Glu Lys Gln Ile
                645                 650                 655

Glu Gly Leu Glu Gly Asn Ile Thr Lys Gln Leu Glu Gln Ala Arg Glu
        660                 665                 670

Gln Glu Glu Lys Asn Leu Asp Ala Tyr Gln Lys Leu Ser Asp Trp Ser
        675                 680                 685

Ser Phe Trp Ser Trp Phe Asp Phe Ser Lys Trp Leu Asn Ile Leu Lys
        690                 695                 700

Ile Gly Phe Leu Ala Val Ile Gly Val Ile Gly Leu Arg Leu Leu Tyr
705                 710                 715                 720

Thr Leu Tyr Thr Cys Ile Ala Arg Val Arg Gln Gly Tyr Ser Pro Leu
                725                 730                 735

Ser Pro Gln Ile His Ile His Pro Trp Lys Gly Gln Pro Asp Asn Ala
        740                 745                 750

Gly Glu Pro Glu Glu Gly Gly Arg Thr Gly Lys Ser Lys Ser Thr His
        755                 760                 765

<210> SEQ ID NO 5
<211> LENGTH: 879
<212> TYPE: PRT
<213> ORGANISM: Simian immunodeficiency virus

<400> SEQUENCE: 5

Met Gly Pro Leu Arg Gly Lys Gly Val Leu Leu Val Ile Leu Gly Leu
1               5                   10                  15

Ser Leu Ile Gly Leu Leu Tyr Gly Thr Gln Tyr Ile Thr Val Phe Tyr
                20                  25                  30

Gly Ile Pro Val Trp Lys Asn Ser Ser Val Gln Ala Phe Cys Met Thr
        35                  40                  45
```

```
Pro Asn Thr Asn Leu Trp Ala Thr Thr Asn Cys Ile Pro Asp Asp His
    50                  55                  60

Asp Tyr Thr Glu Val Gln Leu Asn Val Ser Glu Lys Phe Glu Ala Trp
65                  70                  75                  80

Lys Asp Arg Asn Pro Leu Val Ala Gln Ala Glu Ser Asn Ile His Leu
                85                  90                  95

Leu Phe Glu Ser Thr Leu Lys Pro Cys Val Lys Leu Thr Pro Met Cys
            100                 105                 110

Ile Lys Met Asn Cys Thr Lys Leu Thr Ser Thr Ala Pro Thr Ser Ser
        115                 120                 125

Thr Pro Thr Ser Ser Ser Thr Thr Asp Pro Cys Pro Asn Thr Asp Glu
    130                 135                 140

Ser Ser Cys Asn Ala Thr Leu Val Thr Asn Ser Met Asp Tyr Glu Asn
145                 150                 155                 160

Ser Ser Ile Cys Ser Phe Ala Met Ala Gly Tyr Arg Arg Asp Val Lys
                165                 170                 175

Lys Lys Tyr Asn Ser Thr Trp Tyr Asp Gln Glu Leu Val Cys Glu Lys
            180                 185                 190

Glu Asn Asn Thr Thr Gly Thr Arg Gly Cys Tyr Met Ile His Cys Asn
        195                 200                 205

Asp Ser Val Ile Lys Glu Ala Cys Glu Lys Thr Tyr Trp Asp Thr Leu
    210                 215                 220

Arg Leu Arg Tyr Cys Ala Pro Ala Gly Phe Ala Ile Leu Lys Cys Lys
225                 230                 235                 240

Asp Thr Asn Tyr Thr Gly Phe Gly Val Cys Arg Asn Val Ser Val Val
                245                 250                 255

Ser Cys Thr Gly Leu Met Asn Thr Thr Val Ser Ser Ala Phe Gly Ile
            260                 265                 270

Asn Gly Ser Gln Ala Glu Asn Arg Thr Glu Ile Trp Gln Lys His Gly
        275                 280                 285

Val Ser Asn Asn Ser Val Ile Ile Lys Leu Asn Lys His Tyr Lys Leu
    290                 295                 300

Lys Ile Val Cys Arg Arg Pro Gly Asn Lys Thr Val Leu Pro Val Thr
305                 310                 315                 320

Ile Met Ala Gly Leu Val Phe His Ser Gln Gln Tyr Asn Thr Lys Leu
                325                 330                 335

Arg Gln Ala Trp Cys His Phe Gln Gly Asp Trp Lys Gly Ala Trp Arg
            340                 345                 350

Glu Val Arg Lys Thr Ile Val Glu Leu Pro Lys Glu Lys Tyr Arg Gly
        355                 360                 365

Thr Asn Asn Thr Arg Gln Ile Trp Leu Ser Arg Gln Trp Gly Asp Pro
    370                 375                 380

Glu Ala Ala Asn Ile Trp Leu Asn Cys Gln Gly Glu Phe Phe Tyr Cys
385                 390                 395                 400

Thr Pro Asp Trp Phe Val Asn Trp Leu Asn Asn Glu Ser Asn Ser Gly
                405                 410                 415

Arg Asn Val Asp Val Glu Gly Asn Asn Cys Thr Thr Gly Lys Asp Lys
            420                 425                 430

Arg Cys Tyr Lys Arg Thr Tyr Val Pro Cys His Ile Arg Ser Ile Val
        435                 440                 445

Asn Asp Trp Tyr Thr Leu Ser Lys Lys Thr Tyr Ala Pro Pro Arg Glu
    450                 455                 460

Gly His Leu Glu Cys Thr Ser Thr Val Thr Ser Met Met Val Ser Leu
```

```
            465                 470                 475                 480
Asp Tyr Asn Ser Lys Glu Arg Thr Asn Val Thr Leu Thr Ala Asn Leu
                    485                 490                 495

Glu Asn Ile Trp Ala Tyr Glu Leu Gly Arg Tyr Lys Leu Ile Glu Ile
                500                 505                 510

Glu Pro Ile Gly Phe Ala Pro Thr Glu Ile Arg Arg Tyr Val Gly Pro
            515                 520                 525

Thr Arg Glu Lys Arg Val Pro Phe Val Leu Gly Phe Leu Gly Phe Leu
        530                 535                 540

Gly Ala Ala Gly Ala Ala Met Gly Ala Thr Ala Thr Ala Leu Thr Val
545                 550                 555                 560

Gln Ser Gln Gln Leu Leu Ala Gly Ile Leu Gln Gln Gln Lys Asn Leu
                    565                 570                 575

Leu Ala Ala Val Glu Gln Gln Gln Met Leu Lys Leu Thr Ile Trp
                580                 585                 590

Gly Val Lys Asn Leu Asn Ala Arg Val Thr Ala Leu Glu Lys Tyr Leu
                    595                 600                 605

Glu Asp Gln Thr Arg Leu Asn Leu Trp Gly Cys Ala Phe Lys Gln Val
                610                 615                 620

Cys His Thr Thr Val Pro Trp Thr Phe Asn Asn Thr Pro Asp Trp Asp
625                 630                 635                 640

Asn Met Thr Trp Gln Glu Trp Glu Ser Gln Ile Thr Ala Leu Glu Gly
                    645                 650                 655

Asn Ile Ser Thr Thr Leu Val Lys Ala Tyr Glu Gln Glu Gln Lys Asn
                    660                 665                 670

Met Asp Thr Tyr Gln Lys Leu Gly Asp Trp Thr Ser Trp Trp Asn Ile
                675                 680                 685

Phe Asp Val Ser Ser Trp Phe Trp Trp Ile Lys Trp Gly Phe Tyr Ile
        690                 695                 700

Val Ile Gly Leu Ile Leu Phe Arg Met Ala Trp Leu Ile Trp Gly Cys
705                 710                 715                 720

Ile Ala Arg Val Arg Gln Gly Tyr Phe Pro Leu Ser Pro Gln Ile Asn
                    725                 730                 735

Ile Arg Leu Gly Arg Glu Gln Pro Asp Asn Ala Gly Gly Glu Asp Lys
                740                 745                 750

Asp Ser Ser Ser Ser Arg Asp Lys Ser Pro Pro Ser Val Lys Glu Ser
                755                 760                 765

Leu Leu Pro Asn Arg Gly Gly Ile Gln Ala Glu Glu Arg Ala Trp Arg
        770                 775                 780

Gln His Leu Thr Asn Trp Cys Leu Thr Ile Ser Ser Trp Leu Leu Arg
785                 790                 795                 800

Leu Tyr Gln Ile Leu Arg Arg Ser Leu Thr Thr Leu Gln Leu Leu
                    805                 810                 815

Arg Gln Glu Cys Gln Tyr Ile Gln Tyr Gly Trp Gln Gln Phe Lys Glu
                820                 825                 830

Gly Ala Ala Arg Ser Phe Glu Ala Leu Ala Ser Ala Ala Gln Ser Ala
                835                 840                 845

Ser Arg Thr Leu Trp Asn Ala Cys Arg Ser Ala Tyr Arg Ala Ile Leu
        850                 855                 860

Glu His Pro Arg Arg Met Arg Gln Glu Leu Glu Arg Trp Phe Asn
865                 870                 875

<210> SEQ ID NO 6
<211> LENGTH: 390
```

```
<212> TYPE: PRT
<213> ORGANISM: Homo sapiens

<400> SEQUENCE: 6

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp
385                 390
```

<210> SEQ ID NO 7
<211> LENGTH: 857
<212> TYPE: PRT
<213> ORGANISM: Human immunodeficiency virus

<400> SEQUENCE: 7

Met Ala His Thr Ser Asn His Leu Phe Ile Leu Leu Leu Ile Ser
1               5                   10                  15

Val Tyr Gly Phe Leu Gly His Lys Lys Asn Tyr Val Thr Val Phe Tyr
            20                  25                  30

Gly Ile Pro Ala Trp Arg Asn Ala Thr Val Pro Leu Phe Cys Ala Thr
        35                  40                  45

Thr Asn Arg Asp Thr Trp Gly Thr Val Gln Cys Leu Pro Asp Asn Gly
    50                  55                  60

Asp Tyr Thr Glu Ile Ser Val Asn Ile Thr Glu Ala Phe Asp Ala Trp
65                  70                  75                  80

Asn Asn Thr Val Thr Glu Gln Ala Val Asp Asp Val Trp Ser Leu Phe
                85                  90                  95

Glu Thr Ser Ile Lys Pro Cys Val Lys Leu Thr Pro Leu Cys Val Ala
            100                 105                 110

Met Arg Cys Asn Asn Thr Gly Thr Asn Thr Thr Thr Lys Pro Ile Thr
        115                 120                 125

Thr Pro Ile Thr Thr Thr Lys Pro Ser Glu Asn Leu Leu Asn Asp Thr
    130                 135                 140

Ser Pro Cys Ile Lys Asn Asp Thr Cys Pro Gly Ile Gly Leu Glu Asn
145                 150                 155                 160

Thr Val Asp Cys Tyr Phe Asn Met Thr Gly Leu Arg Arg Asp Glu Lys
                165                 170                 175

Lys Gln Tyr Lys Asp Thr Trp Tyr Glu Lys Asp Leu Glu Cys Asn Gly
            180                 185                 190

Asn Ser Thr Ser Thr Ile Cys Tyr Met Arg Thr Cys Asn Thr Ser Val
        195                 200                 205

Ile Gln Glu Ser Cys Asp Lys His Tyr Trp Asp Ser Leu Arg Phe Arg
    210                 215                 220

Tyr Cys Ala Pro Pro Gly Tyr Ala Leu Leu Arg Cys Asn Asp Thr Asn
225                 230                 235                 240

Tyr Ser Gly Phe Met Pro Lys Cys Ser Lys Val Val Ser Ser Cys
                245                 250                 255

Thr Arg Met Met Glu Thr Gln Thr Ser Thr Trp Phe Gly Phe Asn Gly
            260                 265                 270

Thr Arg Thr Glu Asn Arg Thr Tyr Met Tyr Trp His Ser Lys Asp Asn
        275                 280                 285

Arg Thr Ile Ile Ser Leu Asn Lys Tyr Tyr Asn Leu Thr Met His Cys
    290                 295                 300

Arg Arg Pro Gly Asn Lys Thr Val Ile Pro Ile Thr Ile Met Ser Gly
305                 310                 315                 320

Leu Asn Phe His Ser Gln Pro Leu Asn Thr Arg Pro Arg Gln Ala Trp
                325                 330                 335

Cys Trp Phe Lys Gly Asn Trp Ile Glu Ala Ile Arg Glu Val Lys Glu
            340                 345                 350

Thr Ile Ile Lys His Pro Arg Tyr Lys Gly Thr Asn Asn Thr Glu Arg
        355                 360                 365

Ile Arg Leu Val Gly Pro Ser Ala Gly Ser Asp Pro Glu Val Arg His
    370                 375                 380

```
Met Trp Thr Asn Cys Arg Gly Glu Phe Phe Tyr Cys Asn Met Thr Trp
385                 390                 395                 400

Phe Leu Asn Trp Val Glu Asn Arg Thr Gly Thr Thr Gln Lys Asn Tyr
            405                 410                 415

Val Thr Cys His Ile Lys Gln Ile Val Asn Thr Trp His Lys Val Gly
        420                 425                 430

Lys Tyr Val Tyr Leu Pro Pro Arg Glu Gly Thr Leu Ser Cys Asn Ser
            435                 440                 445

Ser Val Thr Ser Leu Ile Ala Asn Ile Asp Val Tyr Tyr Asp Gly Asn
    450                 455                 460

Asp Thr Lys Thr Asn Ile Thr Met Ser Ala Glu Val Gly Glu Leu Tyr
465                 470                 475                 480

Arg Leu Glu Leu Gly Asp Tyr Lys Leu Val Glu Ile Thr Pro Ile Gly
                485                 490                 495

Phe Ala Pro Thr Glu Ile Lys Arg Tyr Ser Ser Thr Thr Pro Arg Asn
            500                 505                 510

Lys Arg Gly Val Met Val Leu Gly Phe Leu Gly Leu Leu Ala Met Ala
        515                 520                 525

Gly Ser Ala Met Gly Ala Thr Ser Leu Thr Leu Ser Ala Gln Ser Arg
530                 535                 540

Thr Leu Leu Ala Gly Ile Val Gln Gln Gln Gln Leu Leu Asp Val
545                 550                 555                 560

Val Lys Arg Gln Gln Glu Leu Leu Arg Leu Thr Val Trp Gly Thr Lys
                565                 570                 575

Asn Leu Gln Thr Arg Val Thr Ala Ile Glu Lys Tyr Leu Lys Asp Gln
            580                 585                 590

Ala Leu Leu Asn Ser Trp Gly Cys Ala Phe Arg Gln Val Cys His Thr
    595                 600                 605

Thr Val Pro Trp Pro Asn Glu Thr Leu Thr Pro Asp Trp Glu Asn Met
610                 615                 620

Thr Trp Gln Gln Trp Glu Lys Arg Val Asn Phe Leu Asp Ala Asn Ile
625                 630                 635                 640

Thr Ala Leu Leu Glu Glu Ala Gln Ile Gln Gln Glu Arg Asn Met Tyr
                645                 650                 655

Glu Leu Gln Lys Leu Asn Ser Trp Asp Val Phe Gly Asn Trp Phe Asp
            660                 665                 670

Phe Thr Ser Trp Met Ala Tyr Ile Arg Leu Gly Leu Tyr Val Val Ala
    675                 680                 685

Gly Leu Ile Val Leu Arg Ile Val Ile Tyr Ile Gln Met Leu Ala
690                 695                 700

Arg Leu Arg Lys Gly Tyr Arg Pro Val Phe Ser Ser Pro Ser Tyr
705                 710                 715                 720

Thr Gln Gln Ile Pro Ile Arg Lys His Arg Gly Gln Pro Ala Asn Glu
                725                 730                 735

Glu Thr Glu Asp Glu Gly Gly Asn Glu Gly Ala Tyr Arg Ser Trp Pro
            740                 745                 750

Trp Gln Ile Glu Tyr Ala His Phe Leu Ile Arg Gln Leu Arg Asn Leu
    755                 760                 765

Leu Ile Trp Leu Tyr Asn Gly Cys Arg Asn Leu Leu Leu Lys Thr Ser
770                 775                 780

Gln Ile Leu Gln Pro Ala Leu Gln Pro Leu Arg Leu Ser Leu Ala Tyr
785                 790                 795                 800

Leu Gln Tyr Gly Ile Ser Trp Phe Gln Glu Ala Ile Gln Ala Ala Thr
                805                 810                 815
```

-continued

Arg Ala Ala Arg Glu Thr Leu Ala Asn Thr Gly Arg Ala Leu Trp Lys
            820                 825                 830

Ala Leu Arg Arg Thr Ala Glu Ala Ile Ile Ala Ile Pro Arg Arg Ile
            835                 840                 845

Arg Gln Gly Leu Glu Leu Ala Leu Leu
            850                 855

<210> SEQ ID NO 8
<211> LENGTH: 865
<212> TYPE: PRT
<213> ORGANISM: Human immunodeficiency virus

<400> SEQUENCE: 8

Met Glu Pro Gly Arg Asn Gln Leu Leu Ala Val Ile Leu Leu Thr Ser
 1               5                  10                  15

Ala Cys Leu Ile Tyr Cys Lys Gln Tyr Val Thr Val Phe Tyr Gly Val
            20                  25                  30

Pro Val Trp Arg Asn Ala Ser Ile Pro Leu Phe Cys Ala Thr Lys Asn
        35                  40                  45

Arg Asp Thr Trp Gly Thr Ile Gln Cys Leu Pro Asp Asn Asp Asp Tyr
    50                  55                  60

Gln Glu Ile Pro Leu Asn Val Thr Glu Ala Phe Asp Ala Trp Asp Asn
65                  70                  75                  80

Thr Val Thr Glu Gln Ala Ile Glu Asp Val Trp Arg Leu Phe Glu Thr
                85                  90                  95

Ser Ile Lys Pro Cys Val Lys Leu Thr Pro Leu Cys Val Ala Met Asn
            100                 105                 110

Cys Asn Pro Val Thr Gly Asn Asn Thr Asn Ala Thr Ala Lys Pro Thr
        115                 120                 125

Ala Ala Arg Pro Thr Thr Asn Pro Ser Tyr Leu Thr Ile Ile Asn Glu
    130                 135                 140

Ser Ser Thr Cys Val Gly Ala Asp Asn Cys Thr Gly Leu Gly Asp Glu
145                 150                 155                 160

Gly Met Val Asn Cys Lys Phe Asn Met Thr Gly Leu Glu Gln Asp Lys
                165                 170                 175

Ile Lys Gly Tyr Thr Asp Thr Trp Tyr Ser Asp Asp Val Val Cys Asp
            180                 185                 190

Ser Thr Asn Lys Thr Gly Thr Asn Thr Thr Cys Tyr Met Arg His Cys
        195                 200                 205

Asn Thr Ser Val Ile Lys Glu Ser Cys Asp Lys His Tyr Trp Asp Ser
    210                 215                 220

Met Lys Phe Arg Tyr Cys Thr Pro Pro Gly Tyr Ala Leu Leu Arg Cys
225                 230                 235                 240

Asn Asp Thr Asn Tyr Ser Gly Phe Ala Pro Asn Cys Pro Lys Val Val
                245                 250                 255

Ala Ala Ser Cys Thr Arg Met Met Glu Thr Gln Thr Ser Thr Trp Phe
            260                 265                 270

Gly Phe Asn Gly Thr Arg Ala Glu Asn Arg Thr Tyr Ile Tyr Trp His
        275                 280                 285

Gly Arg Asp Asn Arg Thr Ile Ile Ser Leu Asn Lys His Tyr Asn Leu
    290                 295                 300

Thr Met His Cys Lys Arg Pro Gly Asn Lys Thr Val Val Pro Ile Thr
305                 310                 315                 320

Leu Met Ser Gly His Arg Phe His Ser Gln Ala Val Ile Asn Lys Lys
                325                 330                 335

-continued

Pro Arg Gln Ala Trp Cys Trp Phe Lys Gly Asn Trp Lys Gly Ala Met
        340                 345                 350

Gln Glu Val Lys Gln Thr Leu Ala Gly His Pro Arg Tyr Lys Gly Thr
        355                 360                 365

Asn Asp Thr Ser Lys Ile Asn Phe Val Lys Pro Gly Val Gly Ser Asp
        370                 375                 380

Pro Glu Val Thr Tyr Met Trp Thr Asn Cys Arg Gly Glu Phe Phe Tyr
385                 390                 395                 400

Cys Asn Met Thr Trp Phe Leu Asn Trp Val Glu Asn Arg Thr Ser Gln
                405                 410                 415

Lys Gln Arg Asn Tyr Ala Pro Cys His Ile Arg Gln Ile Ile Asn Thr
                420                 425                 430

Trp His Lys Val Gly Gln Tyr Val Tyr Leu Pro Pro Arg Glu Gly Glu
                435                 440                 445

Leu Thr Cys Asn Ser Thr Val Thr Ser Ile Ile Ala Asn Ile Asp Thr
        450                 455                 460

Asp Gly Asn Gln Thr Asn Ile Thr Phe Ser Ala Glu Val Ala Glu Leu
465                 470                 475                 480

Tyr Arg Leu Glu Leu Gly Asp Tyr Lys Leu Ile Glu Ile Thr Pro Ile
                485                 490                 495

Gly Phe Ala Pro Thr Ser Glu Lys Arg Tyr Ser Ser Ala Pro Ala Arg
                500                 505                 510

Asn Lys Arg Gly Val Phe Val Leu Gly Leu Leu Gly Phe Leu Ala Thr
                515                 520                 525

Ala Gly Ser Ala Met Gly Ala Ala Ser Leu Thr Leu Ser Ala Gln Ser
        530                 535                 540

Arg Thr Leu Leu Ala Gly Ile Val Gln Gln Gln Gln Gln Leu Leu Asp
545                 550                 555                 560

Ile Val Lys Arg Gln Gln Glu Leu Leu Arg Leu Thr Val Trp Gly Thr
                565                 570                 575

Lys Asn Leu Gln Ala Arg Val Thr Ala Ile Glu Lys Tyr Leu Lys Asp
                580                 585                 590

Gln Ala Gln Leu Asn Ser Trp Gly Cys Thr Phe Arg Gln Val Cys His
                595                 600                 605

Thr Thr Val Pro Trp Val Asn Asp Ser Leu Thr Pro Arg Trp Asn Asn
        610                 615                 620

Met Thr Trp Gln Glu Trp Glu Lys Gln Val Arg Tyr Leu Glu Ala Asn
625                 630                 635                 640

Ile Ser Gln Ser Leu Glu Glu Ala Gln Ile Gln Gln Glu Lys Asn Met
                645                 650                 655

Tyr Glu Leu Gln Lys Leu Asn Ser Trp Asp Val Phe Gly Asn Trp Phe
                660                 665                 670

Asp Leu Thr Ser Trp Ile Lys Tyr Ile Gln Tyr Gly Val Tyr Ile Val
                675                 680                 685

Val Gly Ile Ile Ala Leu Arg Ile Ala Ile Tyr Val Val Gln Leu Leu
        690                 695                 700

Ser Arg Phe Arg Lys Gly Tyr Arg Pro Val Phe Ser Ser Pro Pro Gly
705                 710                 715                 720

Tyr Leu Gln Gln Ile His Ile His Thr Asp Arg Gly Gln Pro Ala Asn
                725                 730                 735

Glu Glu Thr Glu Gly Asp Ala Gly Asp Ala Ser Gly Tyr Asp Phe Trp
                740                 745                 750

Pro Trp Pro Ile Asn Tyr Ile Gln Leu Leu Ile His Leu Leu Thr Arg

```
                    755                 760                 765
Leu Leu Thr Gly Leu Tyr Ser Ile Cys Arg Asp Leu Leu Ser Ala Asn
    770                 775                 780

Ser Pro Thr Arg Arg Leu Ile Ser Gln Asn Leu Thr Ala Ile Arg Asp
785                 790                 795                 800

Trp Leu Arg Leu Lys Ala Ala Tyr Leu Gln Tyr Gly Cys Glu Trp Ile
                805                 810                 815

Gln Glu Ala Phe Gln Ala Ile Ala Arg Thr Ala Arg Glu Thr Leu Ala
            820                 825                 830

Gly Ala Trp Arg Gly Leu Cys Lys Ala Val Gln Arg Ile Gly Arg Gly
        835                 840                 845

Ile Leu Ala Val Pro Arg Arg Ile Arg Gln Gly Ala Glu Ile Ala Leu
    850                 855                 860

Leu
865

<210> SEQ ID NO 9
<211> LENGTH: 443
<212> TYPE: PRT
<213> ORGANISM: Human immunodeficiency virus

<400> SEQUENCE: 9

Met Met Asn Gln Leu Leu Ile Ala Ile Leu Leu Ala Ser Ala Cys Leu
1               5                   10                  15

Val Tyr Cys Thr Gln Tyr Val Thr Val Phe Tyr Gly Val Pro Thr Trp
            20                  25                  30

Lys Asn Ala Thr Ile Pro Leu Phe Cys Ala Thr Arg Asn Arg Asp Thr
        35                  40                  45

Trp Gly Thr Ile Gln Cys Leu Pro Asp Asn Asp Asp Tyr Gln Glu Ile
    50                  55                  60

Thr Leu Asn Val Thr Glu Ala Phe Asp Ala Trp Asn Asn Thr Val Thr
65                  70                  75                  80

Glu Gln Ala Ile Glu Asp Val Trp His Leu Phe Glu Thr Ser Ile Lys
                85                  90                  95

Pro Cys Val Lys Leu Thr Pro Leu Cys Val Ala Met Lys Cys Ser Ser
            100                 105                 110

Thr Glu Ser Ser Ile Gly Asn Asn Thr Thr Ser Lys Ser Thr Ser Thr
        115                 120                 125

Thr Thr Thr Thr Pro Thr Asp Gln Glu Gln Glu Ile Ser Glu Asp Thr
    130                 135                 140

Pro Cys Ala Arg Ala Asp Asn Cys Ser Gly Leu Gly Lys Glu Glu Thr
145                 150                 155                 160

Ile Asn Cys Gln Phe Asn Met Thr Gly Leu Glu Arg Asp Lys Lys Lys
                165                 170                 175

Gln Tyr Asn Glu Thr Trp Tyr Ser Lys Asp Val Val Cys Lys Thr Asn
            180                 185                 190

Asn Ser Thr Asn Gln Thr Gln Cys Tyr Met Asn His Cys Asn Thr Ser
        195                 200                 205

Val Ile Thr Glu Ser Cys Asp Lys His Tyr Trp Asp Ala Ile Arg Phe
    210                 215                 220

Arg Tyr Cys Ala Pro Pro Gly Tyr Ala Leu Leu Arg Cys Asn Asp Thr
225                 230                 235                 240

Asn Tyr Ser Gly Phe Ala Pro Asn Cys Ser Lys Val Val Ala Ser Thr
                245                 250                 255

Cys Thr Arg Met Met Glu Thr Gln Thr Ser Thr Trp Phe Gly Phe Asn
```

```
                260                 265                 270
Gly Thr Arg Ala Glu Asn Arg Thr Tyr Ile Tyr Trp His Gly Arg Asp
            275                 280                 285
Asn Arg Thr Ile Ile Ser Leu Asn Lys Tyr Tyr Asn Leu Ser Leu His
        290                 295                 300
Cys Lys Arg Pro Gly Asn Lys Thr Val Lys Gln Ile Met Leu Met Ser
305                 310                 315                 320
Gly His Val Phe His Ser His Tyr Lys Pro Ile Asn Lys Arg Pro Arg
                325                 330                 335
Gln Ala Trp Cys Trp Phe Lys Gly Lys Trp Lys Asp Ala Met Gln Glu
            340                 345                 350
Val Lys Glu Thr Leu Ala Lys His Pro Arg Tyr Arg Gly Thr Asn Asp
        355                 360                 365
Thr Arg Asn Ile Ser Phe Ala Ala Pro Gly Lys Gly Ser Asp Pro Glu
370                 375                 380
Val Ala Tyr Met Trp Thr Asn Cys Arg Gly Glu Phe Phe Tyr Cys Asn
385                 390                 395                 400
Met Thr Trp Phe Leu Asn Trp Ile Glu Asn Lys Thr His Arg Asn Tyr
                405                 410                 415
Ala Pro Cys His Ile Arg Gln Ile Ile Asn Thr Trp His Lys Val Gly
            420                 425                 430
Ile Asn Val Tyr Leu Pro Pro Arg Glu Gly Glu
            435                 440

<210> SEQ ID NO 10
<211> LENGTH: 856
<212> TYPE: PRT
<213> ORGANISM: Human immunodeficiency virus

<400> SEQUENCE: 10

Met Arg Val Lys Glu Lys Tyr Gln His Leu Trp Arg Trp Gly Trp Arg
1               5                   10                  15
Trp Gly Thr Met Leu Leu Gly Met Leu Met Ile Cys Ser Ala Thr Glu
            20                  25                  30
Lys Leu Trp Val Thr Val Tyr Tyr Gly Val Pro Val Trp Lys Glu Ala
        35                  40                  45
Thr Thr Thr Leu Phe Cys Ala Ser Asp Ala Lys Ala Tyr Asp Thr Glu
    50                  55                  60
Val His Asn Val Trp Ala Thr His Ala Cys Val Pro Thr Asp Pro Asn
65                  70                  75                  80
Pro Gln Glu Val Val Leu Val Asn Val Thr Glu Asn Phe Asn Met Trp
                85                  90                  95
Lys Asn Asp Met Val Glu Gln Met His Glu Asp Ile Ile Ser Leu Trp
            100                 105                 110
Asp Gln Ser Leu Lys Pro Cys Val Lys Leu Thr Pro Leu Cys Val Ser
        115                 120                 125
Leu Lys Cys Thr Asp Leu Lys Asn Asp Thr Asn Thr Asn Ser Ser Ser
    130                 135                 140
Gly Arg Met Ile Met Glu Lys Gly Glu Ile Lys Asn Cys Ser Phe Asn
145                 150                 155                 160
Ile Ser Thr Ser Ile Arg Gly Lys Val Gln Lys Glu Tyr Ala Phe Phe
                165                 170                 175
Tyr Lys Leu Asp Ile Ile Pro Ile Asp Asn Asp Thr Thr Ser Tyr Lys
            180                 185                 190
Leu Thr Ser Cys Asn Thr Ser Val Ile Thr Gln Ala Cys Pro Lys Val
```

-continued

```
                195                 200                 205
Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
        260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Thr Arg
290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
                340                 345                 350

Phe Gly Asn Asn Lys Thr Ile Ile Phe Lys Gln Ser Ser Gly Gly Asp
                355                 360                 365

Pro Glu Ile Val Thr His Ser Phe Asn Cys Gly Gly Glu Phe Phe Tyr
        370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
        420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
        500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
        530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
                580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
        610                 615                 620
```

```
His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
            645                 650                 655

Glu Gln Glu Leu Leu Glu Leu Asp Lys Trp Ala Ser Leu Trp Asn Trp
        660                 665                 670

Phe Asn Ile Thr Asn Trp Leu Trp Tyr Ile Lys Leu Phe Ile Met Ile
    675                 680                 685

Val Gly Gly Leu Val Gly Leu Arg Ile Val Phe Ala Val Leu Ser Ile
690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
            725                 730                 735

Gly Gly Glu Arg Asp Arg Asp Arg Ser Ile Arg Leu Val Asn Gly Ser
        740                 745                 750

Leu Ala Leu Ile Trp Asp Asp Leu Arg Ser Leu Cys Leu Phe Ser Tyr
    755                 760                 765

His Arg Leu Arg Asp Leu Leu Leu Ile Val Thr Arg Ile Val Glu Leu
770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
            805                 810                 815

Ala Thr Ala Ile Ala Val Ala Glu Gly Thr Asp Arg Val Ile Glu Val
        820                 825                 830

Val Gln Gly Ala Cys Arg Ala Ile Arg His Ile Pro Arg Arg Ile Arg
    835                 840                 845

Gln Gly Leu Glu Arg Ile Leu Leu
    850                 855

<210> SEQ ID NO 11
<211> LENGTH: 879
<212> TYPE: PRT
<213> ORGANISM: Simian immunodeficiency virus
<220> FEATURE:
<221> NAME/KEY: VARIANT
<222> LOCATION: 176, 792
<223> OTHER INFORMATION: Xaa = Any Amino Acid

<400> SEQUENCE: 11

Met Gly Cys Leu Gly Asn Gln Leu Leu Ile Ala Ile Leu Leu Leu Ser
1               5                   10                  15

Val Tyr Gly Ile Tyr Cys Thr Leu Tyr Val Thr Val Phe Tyr Gly Val
            20                  25                  30

Pro Ala Trp Arg Asn Ala Thr Ile Pro Leu Phe Cys Ala Thr Lys Asn
        35                  40                  45

Arg Asp Thr Trp Gly Thr Thr Gln Cys Leu Pro Asp Asn Gly Asp Tyr
    50                  55                  60

Ser Glu Met Ala Leu Asn Val Thr Glu Ser Phe Asp Ala Trp Asn Asn
65                  70                  75                  80

Thr Val Thr Glu Gln Ala Ile Glu Asp Val Trp Gln Leu Phe Glu Thr
            85                  90                  95

Ser Ile Arg Pro Cys Val Lys Leu Ser Pro Leu Cys Ile Thr Met Arg
        100                 105                 110

Cys Asn Lys Ser Glu Thr Asp Arg Trp Gly Leu Thr Lys Ser Ile Thr
    115                 120                 125
```

```
Thr Thr Ala Ser Thr Thr Ser Thr Thr Ala Ser Ala Lys Val Asp Met
        130                 135                 140

Val Asn Glu Thr Ser Ser Cys Ile Ala Gln Asp Asn Cys Thr Gly Leu
145                 150                 155                 160

Glu Gln Glu Gln Met Ile Ser Cys Lys Phe Asn Met Thr Gly Leu Xaa
                165                 170                 175

Arg Asp Lys Lys Lys Glu Tyr Asn Glu Thr Trp Tyr Ser Ala Asp Leu
                180                 185                 190

Val Cys Glu Gln Gly Asn Asn Thr Gly Asn Glu Ser Arg Cys Tyr Met
            195                 200                 205

Asn His Cys Asn Thr Ser Val Ile Gln Glu Ser Cys Asp Lys His Tyr
        210                 215                 220

Trp Asp Ala Ile Arg Phe Arg Tyr Cys Ala Pro Pro Gly Tyr Ala Leu
225                 230                 235                 240

Leu Arg Cys Asn Asp Thr Asn Tyr Ser Gly Phe Met Pro Lys Cys Ser
                245                 250                 255

Lys Val Val Ser Ser Cys Thr Arg Met Met Glu Thr Gln Thr Ser
            260                 265                 270

Thr Trp Phe Gly Phe Asn Gly Thr Arg Ala Glu Asn Arg Thr Tyr Ile
        275                 280                 285

Tyr Trp His Gly Arg Asp Asn Arg Thr Ile Ile Ser Leu Asn Lys Tyr
        290                 295                 300

Tyr Asn Leu Thr Met Lys Cys Arg Arg Pro Gly Asn Lys Thr Val Leu
305                 310                 315                 320

Pro Val Thr Ile Met Ser Gly Leu Val Phe His Ser Gln Pro Ile Asn
                325                 330                 335

Asp Arg Pro Lys Gln Ala Trp Cys Trp Phe Gly Gly Lys Trp Lys Asp
                340                 345                 350

Ala Ile Lys Glu Val Lys Gln Thr Ile Val Lys His Pro Arg Tyr Thr
        355                 360                 365

Gly Thr Asn Asn Thr Asp Lys Ile Asn Leu Thr Ala Pro Arg Gly Gly
    370                 375                 380

Asp Pro Glu Val Thr Phe Met Trp Thr Asn Cys Arg Gly Glu Phe Leu
385                 390                 395                 400

Tyr Cys Lys Met Asn Trp Phe Leu Asn Trp Val Glu Asp Arg Asn Thr
                405                 410                 415

Ala Asn Gln Lys Pro Lys Glu Gln His Lys Arg Asn Tyr Val Pro Cys
            420                 425                 430

His Ile Arg Gln Ile Ile Asn Thr Trp His Lys Val Gly Lys Asn Val
        435                 440                 445

Tyr Leu Pro Pro Arg Glu Gly Asp Leu Thr Cys Asn Ser Thr Val Thr
    450                 455                 460

Ser Leu Ile Ala Asn Ile Asp Trp Ile Asp Gly Asn Gln Thr Asn Ile
465                 470                 475                 480

Thr Met Ser Ala Glu Val Ala Glu Leu Tyr Arg Leu Glu Leu Gly Asp
                485                 490                 495

Tyr Lys Leu Val Glu Ile Thr Pro Ile Gly Leu Ala Pro Thr Asx Val
            500                 505                 510

Lys Arg Tyr Thr Thr Gly Gly Thr Ser Arg Asn Lys Arg Gly Val Phe
            515                 520                 525

Val Leu Gly Phe Leu Gly Phe Leu Ala Thr Ala Gly Ser Ala Met Gly
    530                 535                 540

Ala Ala Ser Leu Thr Leu Thr Ala Gln Ser Arg Thr Leu Leu Ala Gly
```

```
                545                 550                 555                 560
    Ile Val Gln Gln Gln Gln Leu Leu Asp Val Val Lys Arg Gln Gln
                        565                 570                 575
    Glu Leu Leu Arg Leu Thr Val Trp Gly Thr Lys Asn Leu Gln Thr Arg
                    580                  585                 590
    Val Thr Ala Ile Glu Lys Tyr Leu Lys Asp Gln Ala Gln Leu Asn Ala
                595                 600                 605
    Trp Gly Cys Ala Phe Arg Gln Val Cys His Thr Thr Val Pro Trp Pro
        610                 615                 620
    Asn Ala Ser Leu Thr Pro Lys Trp Asn Asn Glu Thr Trp Gln Glu Trp
    625                 630                 635                 640
    Glu Arg Lys Val Asp Phe Leu Glu Glu Asn Ile Thr Ala Leu Leu Glu
                        645                 650                 655
    Glu Ala Gln Ile Gln Gln Glu Lys Asn Met Tyr Glu Leu Gln Lys Leu
                    660                 665                 670
    Asn Ser Trp Asp Val Phe Gly Asn Trp Phe Asp Leu Ala Ser Trp Ile
                675                 680                 685
    Lys Tyr Ile Gln Tyr Gly Val Tyr Ile Val Val Gly Val Ile Leu Leu
        690                 695                 700
    Arg Ile Val Ile Tyr Ile Val Gln Met Leu Ala Lys Leu Arg Gln Gly
    705                 710                 715                 720
    Tyr Arg Pro Val Phe Ser Ser Pro Ser Tyr Phe Gln Gln Thr His
                        725                 730                 735
    Ile Gln Gln Asp Pro Ala Leu Pro Thr Arg Glu Gly Lys Glu Gly Asp
                    740                 745                 750
    Gly Gly Glu Gly Gly Gly Asn Ser Ser Trp Pro Trp Gln Ile Glu Tyr
                755                 760                 765
    Ile His Phe Leu Ile Arg Gln Leu Ile Arg Leu Leu Thr Trp Leu Phe
        770                 775                 780
    Ser Asn Cys Arg Thr Leu Leu Xaa Arg Val Tyr Gln Ile Leu Gln Pro
    785                 790                 795                 800
    Ile Leu Gln Arg Leu Ser Ala Thr Leu Gln Arg Ile Arg Glu Val Leu
                        805                 810                 815
    Arg Thr Glu Leu Ala Tyr Leu Gln Tyr Gly Trp Ser Tyr Phe His Glu
                    820                 825                 830
    Ala Val Gln Ala Val Trp Arg Ser Ala Thr Glu Thr Leu Ala Gly Ala
                835                 840                 845
    Trp Gly Asp Leu Trp Glu Thr Leu Arg Arg Gly Gly Arg Trp Ile Leu
        850                 855                 860
    Ala Ile Pro Arg Arg Ile Arg Gln Gly Leu Glu Leu Thr Leu Leu
    865                 870                 875

<210> SEQ ID NO 12
<211> LENGTH: 865
<212> TYPE: PRT
<213> ORGANISM: Simian immunodeficiency virus
<220> FEATURE:
<221> NAME/KEY: VARIANT
<222> LOCATION: 770
<223> OTHER INFORMATION: Xaa = Any Amino Acid

<400> SEQUENCE: 12

Met Arg Tyr Thr Ile Ile Thr Leu Gly Ile Ile Val Ile Gly Ile Gly
1               5                   10                  15

Ile Val Leu Ser Lys Gln Trp Ile Thr Val Phe Tyr Gly Ile Pro Val
            20                  25                  30
```

```
Trp Lys Asn Ser Ser Val Gln Ala Phe Cys Met Thr Pro Thr Thr Ser
         35                  40                  45

Leu Trp Ala Thr Thr Asn Cys Ile Pro Asp Asp His Asp Tyr Thr Glu
 50                  55                  60

Val Pro Leu Asn Ile Thr Glu Pro Phe Glu Ala Trp Gly Asp Arg Asn
 65                  70                  75                  80

Pro Leu Ile Ala Gln Ala Ser Asn Ile His Leu Leu Phe Glu Gln
                 85                  90                  95

Thr Met Lys Pro Cys Val Lys Leu Ser Pro Leu Cys Ile Lys Met Asn
                100                 105                 110

Cys Val Glu Leu Asn Ser Thr Arg Glu Arg Ala Thr Thr Pro Thr Thr
             115                 120                 125

Thr Pro Lys Ser Thr Gly Leu Pro Cys Val Gly Pro Thr Ser Gly Glu
         130                 135                 140

Asn Leu Gln Ser Cys Asn Ala Ser Ile Ile Glu Arg Glu Met Glu Asp
145                 150                 155                 160

Glu Pro Ala Ser Asn Cys Thr Phe Ala Met Ala Gly Tyr Val Arg Asp
                 165                 170                 175

Gln Lys Lys Asn Tyr Tyr Ser Val Val Trp Asn Asp Ala Glu Ile Tyr
             180                 185                 190

Cys Lys Asn Lys Thr Asn Ser Thr Ser Lys Glu Cys Tyr Met Ile His
         195                 200                 205

Cys Asn Asp Ser Val Ile Lys Glu Ala Cys Asp Lys Thr Tyr Trp Asp
210                 215                 220

Gln Leu Arg Leu Arg Tyr Cys Ala Pro Ala Gly Tyr Ala Leu Leu Lys
225                 230                 235                 240

Cys Asn Asp Glu Asp Tyr Asn Gly Tyr Lys Gln Asn Cys Ser Asn Val
                 245                 250                 255

Ser Val Val His Cys Thr Gly Leu Met Asn Thr Thr Val Thr Thr Gly
             260                 265                 270

Leu Leu Leu Asn Gly Ser Tyr His Glu Asn Arg Thr Gln Ile Trp Gln
         275                 280                 285

Lys His Arg Val Asn Asn Asn Thr Val Leu Ile Leu Phe Asn Lys His
290                 295                 300

Tyr Asn Leu Ser Val Thr Cys Arg Arg Pro Gly Asn Lys Thr Val Leu
305                 310                 315                 320

Pro Val Thr Ile Met Ala Gly Leu Val Phe His Ser Gln Lys Tyr Asn
                 325                 330                 335

Met Lys Leu Arg Gln Ala Trp Cys His Phe Glu Gly Asn Trp Arg Gly
             340                 345                 350

Ala Trp Arg Glu Val Lys Gln Lys Ile Val Glu Leu Pro Lys Asp Arg
         355                 360                 365

Tyr Lys Gly Thr Asn Asn Thr Glu His Ile Tyr Leu Gln Arg Gln Trp
370                 375                 380

Gly Asp Pro Glu Ala Ser Asn Leu Trp Phe Asn Cys Gln Gly Glu Phe
385                 390                 395                 400

Phe Tyr Cys Lys Met Asp Trp Phe Leu Asn Tyr Leu Asn Asn Lys Thr
                 405                 410                 415

Trp Asp Ala Tyr His Asn Phe Cys Ser Ser Lys Lys Gly His Ala
             420                 425                 430

Pro Gly Pro Cys Val Gln Arg Thr Tyr Val Ala Tyr His Ile Arg Ser
         435                 440                 445

Val Ile Asn Asp Ser Tyr Thr Leu Ser Lys Lys Thr Tyr Ala Pro Pro
450                 455                 460
```

```
Arg Glu Gly His Leu Gln Cys Arg Ser Thr Val Thr Gly Met Thr Val
465                 470                 475                 480

Glu Leu Asn Tyr Asn Ser Lys Asn Arg Thr Asn Val Thr Leu Ser Pro
            485                 490                 495

Gln Ile Glu Ser Ile Trp Ala Ala Glu Leu Gly Arg Tyr Lys Leu Val
        500                 505                 510

Glu Ile Thr Pro Ile Gly Phe Ala Pro Thr Glu Val Arg Arg Tyr Thr
    515                 520                 525

Gly Gly His Glu Arg Gln Lys Arg Val Pro Phe Val Leu Gly Phe Leu
530                 535                 540

Gly Phe Leu Gly Ala Ala Gly Thr Ala Met Gly Ala Ala Ser Ser
545                 550                 555                 560

Leu Thr Val Gln Ser Arg His Leu Leu Ala Gly Ile Leu Gln Gln Gln
                565                 570                 575

Lys Asn Leu Leu Ala Ala Val Glu Ala Gln Gln Gln Met Leu Lys Leu
            580                 585                 590

Thr Ile Trp Gly Val Lys Asn Leu Asn Ala Arg Val Thr Ala Leu Glu
        595                 600                 605

Lys Tyr Leu Glu Asp Gln Ala Arg Leu Asn Ser Trp Gly Cys Ala Trp
    610                 615                 620

Lys Gln Val Cys His Thr Thr Val Glu Trp Pro Trp Thr Asn Arg Thr
625                 630                 635                 640

Pro Asp Trp Gln Asn Met Thr Trp Leu Glu Trp Glu Arg Gln Ile Ala
                645                 650                 655

Asp Leu Glu Ser Asn Ile Thr Gly Gln Leu Val Lys Ala Arg Glu Gln
            660                 665                 670

Glu Glu Lys Asn Leu Asp Ala Tyr Gln Lys Leu Thr Ser Trp Ser Asp
        675                 680                 685

Phe Trp Ser Trp Phe Asp Phe Ser Lys Trp Leu Asn Ile Leu Lys Met
    690                 695                 700

Gly Phe Leu Val Ile Val Gly Ile Ile Gly Leu Arg Leu Leu Tyr Thr
705                 710                 715                 720

Val Tyr Gly Cys Ile Val Arg Val Arg Gln Gly Tyr Val Pro Leu Ser
                725                 730                 735

Pro Gln Ile His Ile His Gln Val Gly Lys Gly Arg Pro Asp Asn Ala
            740                 745                 750

Asp Glu Pro Gly Glu Gly Gly Asp Asn Ser Arg Ile Lys Leu Glu Ser
        755                 760                 765

Trp Xaa Lys Asp Ser Lys Ser Arg Cys Met Gln Leu Thr Ala Trp Leu
    770                 775                 780

Thr Arg Leu Asn Thr Trp Leu Tyr Asn Ser Cys Leu Thr Leu Leu Ile
785                 790                 795                 800

Gln Leu Arg Lys Ala Phe Gln Tyr Leu Gln Tyr Gly Leu Ala Glu Leu
                805                 810                 815

Lys Thr Gly Ala Gln Glu Ile Leu Gln Thr Leu Ala Gly Val Ala Gln
            820                 825                 830

Asn Ala Cys His Gln Ile Trp Leu Ala Cys Arg Ser Ala Tyr Arg Asn
        835                 840                 845

Ile Val Asn Ser Pro Arg Arg Val Arg Gln Gly Leu Glu Glu Ile Leu
    850                 855                 860

Asn
865
```

```
<210> SEQ ID NO 13
<211> LENGTH: 843
<212> TYPE: PRT
<213> ORGANISM: Human immunodeficiency virus

<400> SEQUENCE: 13

Met Arg Ala Thr Glu Ile Arg Lys Asn Tyr Gln His Leu Trp Lys Gly
  1               5                  10                  15

Gly Thr Leu Leu Leu Gly Met Leu Met Ile Cys Ser Ala Ala Glu Gln
             20                  25                  30

Leu Trp Val Thr Val Tyr Tyr Gly Val Pro Val Trp Lys Glu Ala Thr
         35                  40                  45

Thr Thr Leu Phe Cys Ala Ser Asp Ala Lys Ala Tyr Asp Thr Glu Val
 50                  55                  60

His Asn Val Trp Ala Thr His Ala Cys Val Pro Thr Asp Pro Asn Pro
 65                  70                  75                  80

Gln Glu Val Lys Leu Glu Asn Val Thr Glu Asn Phe Asn Met Trp Lys
                 85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Arg Asn Ala Thr Asn Thr Thr Ser Ser Ser Trp
130                 135                 140

Glu Thr Met Glu Lys Gly Glu Ile Lys Asn Cys Ser Phe Asn Ile Thr
145                 150                 155                 160

Thr Ser Ile Arg Asp Lys Val Gln Lys Glu Tyr Ala Leu Phe Tyr Asn
                165                 170                 175

Leu Asp Val Val Pro Ile Asp Asn Ala Ser Tyr Arg Leu Ile Ser Cys
            180                 185                 190

Asn Thr Ser Val Ile Thr Gln Ala Cys Pro Lys Val Ser Phe Glu Pro
        195                 200                 205

Ile Pro Ile His Tyr Cys Ala Pro Ala Gly Phe Ala Ile Leu Lys Cys
    210                 215                 220

Asn Asp Lys Lys Phe Asn Gly Thr Gly Pro Cys Thr Asn Val Ser Thr
225                 230                 235                 240

Val Gln Cys Thr His Gly Ile Arg Pro Val Val Ser Thr Gln Leu Leu
                245                 250                 255

Leu Asn Gly Ser Leu Ala Glu Glu Ile Val Ile Arg Ser Glu Asn
            260                 265                 270

Phe Thr Asn Asn Ala Lys Thr Ile Ile Val Gln Leu Asn Glu Ser Val
        275                 280                 285

Val Ile Asn Cys Thr Arg Pro Asn Asn Asn Thr Arg Lys Ser Ile Asn
    290                 295                 300

Ile Gly Pro Gly Arg Ala Leu Tyr Thr Thr Gly Glu Ile Ile Gly Asp
305                 310                 315                 320

Ile Arg Gln Ala His Cys Asn Leu Ser Lys Thr Gln Trp Asn Thr
                325                 330                 335

Leu Glu Gln Ile Ala Ile Lys Leu Lys Glu Gln Phe Gly Asn Asn Lys
            340                 345                 350

Thr Ile Ile Phe Asn Pro Ser Ser Gly Gly Asp Pro Glu Ile Val Thr
        355                 360                 365

His Ser Phe Asn Cys Gly Gly Glu Phe Phe Tyr Cys Asn Ser Thr Gln
    370                 375                 380

Leu Phe Thr Trp Asn Asp Thr Arg Lys Leu Asn Asn Thr Gly Arg Asn
```

```
                385                 390                 395                 400
Ile Thr Leu Pro Cys Arg Ile Lys Gln Ile Ile Asn Met Trp Gln Glu
                    405                 410                 415

Val Gly Lys Ala Met Tyr Ala Pro Pro Ile Arg Gly Gln Ile Arg Cys
            420                 425                 430

Ser Ser Asn Ile Thr Gly Leu Leu Thr Arg Asp Gly Gly Lys Asp
                435                 440                 445

Thr Asn Gly Thr Glu Ile Phe Arg Pro Gly Gly Asp Met Arg Asp
    450                 455                 460

Asn Trp Arg Ser Glu Leu Tyr Lys Tyr Lys Val Val Lys Ile Glu Pro
465                 470                 475                 480

Leu Gly Val Ala Pro Thr Lys Ala Lys Arg Arg Val Val Gln Arg Glu
                485                 490                 495

Lys Arg Ala Val Gly Leu Gly Ala Leu Phe Leu Gly Phe Leu Gly Ala
                500                 505                 510

Ala Gly Ser Thr Met Gly Ala Ala Ser Ile Thr Leu Thr Val Gln Ala
            515                 520                 525

Arg Gln Leu Leu Ser Gly Ile Val Gln Gln Asn Asn Leu Leu Arg
    530                 535                 540

Ala Ile Glu Ala Gln Gln His Leu Leu Gln Leu Thr Val Trp Gly Ile
545                 550                 555                 560

Lys Gln Leu Gln Ala Arg Val Leu Ala Val Glu Arg Tyr Leu Arg Asp
                565                 570                 575

Gln Gln Leu Leu Gly Ile Trp Gly Cys Ser Gly Lys Leu Ile Cys Thr
            580                 585                 590

Thr Thr Val Pro Trp Asn Thr Ser Trp Ser Asn Lys Ser Leu Asn Glu
                595                 600                 605

Ile Trp Asp Asn Met Thr Trp Met Lys Trp Glu Arg Glu Ile Asp Asn
610                 615                 620

Tyr Thr His Ile Ile Tyr Ser Leu Ile Glu Gln Ser Gln Asn Gln Gln
625                 630                 635                 640

Glu Lys Asn Glu Gln Glu Leu Leu Ala Leu Asp Lys Trp Ala Ser Leu
                645                 650                 655

Trp Asn Trp Phe Asp Ile Thr Lys Trp Leu Trp Tyr Ile Lys Ile Phe
            660                 665                 670

Ile Met Ile Val Gly Gly Leu Ile Gly Leu Arg Ile Val Phe Val Val
                675                 680                 685

Leu Ser Ile Val Asn Arg Val Arg Gln Gly Tyr Ser Pro Leu Ser Phe
    690                 695                 700

Gln Thr His Leu Pro Ala Gln Arg Gly Pro Asp Arg Pro Asp Gly Ile
705                 710                 715                 720

Glu Glu Glu Gly Gly Glu Arg Asp Arg Asp Arg Ser Gly Pro Leu Val
                725                 730                 735

Asp Gly Phe Leu Ala Ile Ile Trp Val Asp Leu Arg Ser Leu Cys Leu
            740                 745                 750

Phe Ser Tyr His Arg Leu Arg Asp Leu Leu Leu Ile Val Thr Arg Ile
        755                 760                 765

Val Glu Leu Leu Gly Arg Arg Gly Trp Gly Val Leu Lys Tyr Trp Trp
    770                 775                 780

Asn Leu Leu Gln Tyr Trp Ile Gln Glu Leu Lys Asn Ser Ala Val Ser
785                 790                 795                 800

Leu Leu Asn Ala Thr Ala Ile Ala Val Ala Glu Gly Thr Asp Arg Val
                805                 810                 815
```

-continued

```
Ile Glu Ile Leu Gln Arg Ala Phe Arg Ala Val Leu His Ile Pro Val
            820                 825                 830

Arg Ile Arg Gln Gly Leu Glu Arg Ala Leu Leu
            835                 840

<210> SEQ ID NO 14
<211> LENGTH: 859
<212> TYPE: PRT
<213> ORGANISM: Human immunodeficiency virus

<400> SEQUENCE: 14

Met Cys Gly Arg Asn Gln Leu Phe Val Ala Ser Leu Leu Ala Ser Ala
  1               5                  10                  15

Cys Leu Ile Tyr Cys Val Gln Tyr Val Thr Val Phe Tyr Gly Val Pro
             20                  25                  30

Val Trp Arg Asn Ala Ser Ile Pro Leu Phe Cys Ala Thr Lys Asn Arg
         35                  40                  45

Asp Thr Trp Gly Thr Ile Gln Cys Leu Pro Asp Asn Asp Asp Tyr Gln
     50                  55                  60

Glu Ile Ala Leu Asn Val Thr Glu Ala Phe Asp Ala Trp Asn Asn Thr
 65                  70                  75                  80

Val Thr Glu Gln Ala Val Glu Asp Val Trp Ser Leu Phe Glu Thr Ser
                 85                  90                  95

Ile Lys Pro Cys Val Lys Leu Thr Pro Leu Cys Val Ala Met Arg Cys
            100                 105                 110

Asn Ser Thr Thr Ala Lys Asn Thr Thr Ser Thr Pro Thr Thr Thr Thr
        115                 120                 125

Thr Ala Asn Thr Thr Ile Gly Glu Asn Ser Ser Cys Ile Arg Thr Asp
    130                 135                 140

Asn Cys Thr Gly Leu Gly Glu Glu Glu Met Val Asp Cys Gln Phe Asn
145                 150                 155                 160

Met Thr Gly Leu Glu Arg Asp Lys Lys Lys Leu Tyr Asn Glu Thr Trp
                165                 170                 175

Tyr Ser Lys Asp Val Val Cys Glu Ser Asn Asp Thr Lys Lys Glu Lys
            180                 185                 190

Thr Cys Tyr Met Asn His Cys Asn Thr Ser Val Ile Thr Glu Ser Cys
        195                 200                 205

Asp Lys His Tyr Trp Asp Thr Met Arg Phe Arg Tyr Cys Ala Pro Pro
    210                 215                 220

Gly Phe Ala Leu Leu Arg Cys Asn Asp Thr Asn Tyr Ser Gly Phe Glu
225                 230                 235                 240

Pro Asn Cys Ser Lys Val Val Ala Ala Thr Cys Thr Arg Met Met Glu
                245                 250                 255

Thr Gln Thr Ser Thr Trp Phe Gly Phe Asn Gly Thr Arg Ala Glu Asn
            260                 265                 270

Arg Thr Tyr Ile Tyr Trp His Gly Arg Asp Asn Arg Thr Ile Ile Ser
        275                 280                 285

Leu Asn Lys Phe Tyr Asn Leu Thr Val His Cys Lys Arg Pro Gly Asn
    290                 295                 300

Lys Thr Val Val Pro Ile Thr Leu Met Ser Gly Leu Val Phe His Ser
305                 310                 315                 320

Gln Pro Ile Asn Arg Arg Pro Arg Gln Ala Trp Cys Trp Phe Lys Gly
                325                 330                 335

Glu Trp Lys Glu Ala Met Lys Glu Val Lys Leu Thr Leu Ala Lys His
            340                 345                 350
```

-continued

```
Pro Arg Tyr Lys Gly Thr Asn Asp Thr Glu Lys Ile Arg Phe Ile Ala
    355                 360                 365

Pro Gly Glu Arg Ser Asp Pro Glu Val Ala Tyr Met Trp Thr Asn Cys
    370                 375                 380

Arg Gly Glu Phe Leu Tyr Cys Asn Met Thr Trp Phe Leu Asn Trp Val
385                 390                 395                 400

Glu Asn Arg Thr Asn Gln Thr Gln His Asn Tyr Val Pro Cys His Ile
                405                 410                 415

Lys Gln Ile Ile Asn Thr Trp His Lys Val Gly Lys Asn Val Tyr Leu
                420                 425                 430

Pro Pro Arg Glu Gly Gln Leu Thr Cys Asn Ser Thr Val Thr Ser Ile
            435                 440                 445

Ile Ala Asn Ile Asp Gly Gly Glu Asn Gln Thr Asn Ile Thr Phe Ser
    450                 455                 460

Ala Glu Val Ala Glu Leu Tyr Arg Leu Glu Leu Gly Asp Tyr Lys Leu
465                 470                 475                 480

Ile Glu Val Thr Pro Ile Gly Phe Ala Pro Thr Pro Val Lys Arg Tyr
                485                 490                 495

Ser Ser Ala Pro Val Arg Asn Lys Arg Gly Val Phe Val Leu Gly Phe
            500                 505                 510

Leu Gly Phe Leu Thr Thr Ala Gly Ala Ala Met Gly Ala Ala Ser Leu
    515                 520                 525

Thr Leu Ser Ala Gln Ser Arg Thr Leu Leu Ala Gly Ile Val Gln Gln
530                 535                 540

Gln Gln Gln Leu Leu Asp Val Val Lys Arg Gln Gln Glu Met Leu Arg
545                 550                 555                 560

Leu Thr Val Trp Gly Thr Lys Asn Leu Gln Ala Arg Val Thr Ala Ile
                565                 570                 575

Glu Lys Tyr Leu Lys Asp Gln Ala Gln Leu Asn Ser Trp Gly Cys Ala
            580                 585                 590

Phe Arg Gln Val Cys His Thr Thr Val Pro Trp Val Asn Asp Thr Leu
    595                 600                 605

Thr Pro Asp Trp Asn Asn Met Thr Trp Gln Glu Trp Glu Gln Arg Ile
610                 615                 620

Arg Asn Leu Glu Ala Asn Ile Ser Glu Ser Leu Glu Gln Ala Gln Ile
625                 630                 635                 640

Gln Gln Glu Lys Asn Met Tyr Glu Leu Gln Lys Leu Asn Ser Trp Asp
                645                 650                 655

Val Phe Gly Asn Trp Phe Asp Leu Thr Ser Trp Ile Lys Tyr Ile Gln
            660                 665                 670

Tyr Gly Val Tyr Ile Val Gly Ile Ile Val Leu Arg Ile Val Ile
    675                 680                 685

Tyr Val Val Gln Met Leu Ser Arg Leu Arg Lys Gly Tyr Arg Pro Val
690                 695                 700

Phe Ser Ser Pro Pro Ala Tyr Phe Gln Gln Ile His Ile His Lys Asp
705                 710                 715                 720

Arg Glu Gln Pro Ala Arg Glu Glu Thr Glu Glu Asp Val Gly Asn Ser
                725                 730                 735

Val Gly Asp Asn Trp Trp Pro Trp Pro Ile Arg Tyr Ile His Phe Leu
            740                 745                 750

Ile Arg Gln Leu Ile Arg Leu Leu Asn Arg Leu Tyr Asn Ile Cys Arg
    755                 760                 765

Asp Leu Leu Ser Arg Ser Phe Gln Thr Leu Gln Leu Ile Ser Gln Ser
770                 775                 780
```

```
Leu Arg Arg Ala Leu Thr Ala Val Arg Asp Trp Leu Arg Phe Asn Thr
785                 790                 795                 800

Ala Tyr Leu Gln Tyr Gly Gly Glu Trp Ile Gln Ala Phe Arg Ala
            805                 810                 815

Phe Ala Arg Ala Thr Gly Glu Thr Leu Thr Asn Ala Trp Arg Gly Phe
            820                 825                 830

Trp Gly Thr Leu Gly Gln Ile Gly Arg Gly Ile Leu Ala Val Pro Arg
            835                 840                 845

Arg Ile Arg Gln Gly Ala Glu Ile Ala Leu Leu
    850                 855
```

<210> SEQ ID NO 15
<211> LENGTH: 6
<212> TYPE: PRT
<213> ORGANISM: Artificial Sequence
<220> FEATURE:
<223> OTHER INFORMATION: 4E10/Z13 epitope of gp41

<400> SEQUENCE: 15

```
Asn Trp Phe Asp Ile Thr
1               5
```

<210> SEQ ID NO 16
<211> LENGTH: 10
<212> TYPE: PRT
<213> ORGANISM: Artificial Sequence
<220> FEATURE:
<223> OTHER INFORMATION: 2F5 epitope of gp41

<400> SEQUENCE: 16

```
Glu Leu Leu Ala Leu Asp Lys Trp Ala Ser
1               5               10
```

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 17
tagagccctg gaagcatcca ggaag                                     25

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 18
ttgctacttg tgattgctcc atgt                                      24

<210> SEQ ID NO 19
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 19
gatcaagctt taggcatctc ctatggcagg aagaag                         36

<210> SEQ ID NO 20

```
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 20
agctggatcc gtctcgagat actgctccca ccc                           33

<210> SEQ ID NO 21
<211> LENGTH: 2574
<212> TYPE: DNA
<213> ORGANISM: Human immunodeficiency virus
<220> FEATURE:
<221> NAME/KEY: misc_feature
<222> LOCATION: (0)...(0)
<223> OTHER INFORMATION: gp120 envelope (GenBank Acc No. L36874)

<400> SEQUENCE: 21
```

| | | | |
|---|---|---|---|
| atgtgtggta agaatctact atttgttgcc agcttgctag ctagtgctta cttaatatat | 60 |
| tgcaccaaat atgtgactgt tttctatggc gtgcccgtgt ggagaaatgc atccattccc | 120 |
| ctcttttgtg caactaagaa cagagatact tggggaacca tacagtgctt gccagacaat | 180 |
| gatgattatc aagaaatagc cctgaatgtg acagaggctt cgatgcatg gaataataca | 240 |
| gtaacagaac aggcagtaga agatgtctgg agtctatttg agacatcaat aaaaccatgc | 300 |
| gtcaaactaa caccctctatg tgtagcaatg agttgtaaca gcaccaccgc caccactaca | 360 |
| ccaccaagca ccactaacaa cacaaccaca acagagccca acaggagg gccagagata | 420 |
| aatgaaactt ttccatgcat gcgcacagac aactgcacag gattgggaga ggaagagatg | 480 |
| gtcgattgtc agttcaacat gacaggatta gagagagata agacaaaaca atatagtgaa | 540 |
| acatggtact caaaagatgt agtttgtgag tcaaataacg ccagtgatgg gagagacaga | 600 |
| tgctacatga atcattgcaa cacatcagtc atcacagaat catgcgacaa gcactactgg | 660 |
| gatgctataa ggtttagata ctgtgcacca ccgggttttg ctctgctaag atgtaatgac | 720 |
| accaactatt caggctttat gcccaactgt agtaaggtag tagtgtcctc ttgcacaaga | 780 |
| atgatggaaa cacagacctc tacatggttt ggcttcaatg gtacaagggc agaaaatagg | 840 |
| acatatatgt attggcatag taaagataat aggactatta aagcttgaa taagtattat | 900 |
| aatttaacaa tacattgtaa gaggccagga acaagacag ttgtaccaat aacactcatg | 960 |
| tcagggttag tgttccattc ccagcctatc aataaaagac ctaggcaagc atggtgctgg | 1020 |
| ttcaaaggcg agtggaggga agccatgcag gaggtgaaac aaaccettat aaaacatccc | 1080 |
| aggtataaag gaaccaatga cacaaggaat attacccttta caaaccagg aacaggctca | 1140 |
| gacccagaag tggcatacat gtggactaac tgcagaggaa aatttctcta ctgcaacatg | 1200 |
| acttggttcc tcaattgggt agaaaacaga acgggtcaga cacagcacaa ttatgcgccg | 1260 |
| tgccatataa aacaataat taatacctgg cacaaggtag gaaaaatgt gtatttgcct | 1320 |
| cctagggaag gacaattgac ctgcaactca acagtgacca gcttgattgc taacattgac | 1380 |
| gtagacgtag gtaataaccg gacaaatatt acctttagtg cagaggtggc agaactgtac | 1440 |
| cgattagaat tgggagatta taaattaata gaagtgacac caattggttt cgcacctaca | 1500 |
| tcagaaaaaa gatactcctc tactccgggg agacataaaa gaggtgtatt cgtgctaggg | 1560 |
| ttcttggggtt ttctcacgac agcaggagct gcaatgggcg cggcgtcctt gacgctgtcg | 1620 |
| gctcagtctc ggactttact ggccgggata gtgcagcaac agcaacagct gttagacgtg | 1680 |
| gtcaagagac aacaagaaat gttgcgactg accgtctggg gaacaaaaaa tctccaggca | 1740 |

```
agagtcactg ctattgagaa atacttaaag gaccaggcgc aactaaattc atgggatgt    1800 gcgtttaggc aagtctgcca cactactgta ccatgggtaa atgacagctt gacacctgat   1860
tgggacaaca tgacgtggca acaatgggaa aaacaaatcc gcgacctgga ggcaaatatc   1920
agtgaaagtc tagaacaggc acaaatccag caagaaaaga acatgtatga attacaaaaa   1980
ttaaatagct gggatgtttt tggcaactgg tttgatttag cctcctgggt caaatatatt   2040
cagtatggag tttatatagt agtaggaata gtagctctca gagtaataat atatgtagta   2100
caaatgatag gtagacttag aagaggctat aggcctgttt tctcttcccc ccccggttac   2160
ttccaacaga tccgtatcca caaggaccag gaacagccag ccaacgaaga aacagaagaa   2220
ggaggtggaa acgacggggg ctacagatct tggccctggc agatcgaata catccacttc   2280
ctaattcgcc agctgaggaa cctcttgatt tggctatacg acggctgcag aaccttactg   2340
ttgaagacct tccaaaccct ccaaccagct ctccaaccac tcaggctcct gtttgcgtac   2400
ctccaatatg ggatcggctg gttccaagaa gcagtccaag cagcagcggg ggctacggga   2460
gagactcttg cgagcacagg gaggacctta tgggaggctc tcaggaggac ggcgagggga   2520
atcatcgcag tccccagaag aatcagacag gggcttgaac tcgccctcct gtga         2574
```

<210> SEQ ID NO 22
<211> LENGTH: 2670
<212> TYPE: DNA
<213> ORGANISM: Simian immunodeficiency virus
<220> FEATURE:
<221> NAME/KEY: misc_feature
<222> LOCATION: (0)...(0)
<223> OTHER INFORMATION: gp120 envelope sequence

<400> SEQUENCE: 22

```
atgggatgtc ttgggaatca gctgcttatc gcgctcttgc tattaagtgc ttcagggatt     60
tattgtgttc aatatgtaac agtattctat ggtataccag catggaggaa tgcgacagtt    120
cccctcttct gtgcaaccaa ggatagggac acttggggaa caacacaatg cttgccagat    180
aatggtgatt gctcagaatt ggcaattaat gtcacagagg cttttgatgc ttgggataat    240
acagtcacag aacaagcaat agaggatgta tggaacctct tgaaacatc cattaagccc    300 tgtgtaaaac tcaccccact atgtataaca atgaggtgta ataaaagtga cagacagaa    360 tggggtttaa caggaacacc agcaccaaca acaacacaaa caacaacaac acaagcatca    420
acaacaccaa catcaccaat aacagcaaag gttgtaaatg acagtgatcc ttgtataaaa    480
attaataatt gtacaggctt ggaacaggag cccatggtaa gttgtaaatt aacatgaca    540 gggttaaaaa gagacaaaaa gagagaatat aatgaaacat ggtattcaag agatttagtt    600
tgtgaacaaa taacaatga actgacagt aaatgctata tgaaccattg taacaccagt    660
gttattcaag aatcctgtga caaacattat gggatgcta ttagatttag atattgtgca    720
ccgccaggtt atgctttgct taggtgtaat gattcaaatt attcaggctt gctcctaac    780 tgtactaagg tagtagttac ttcatgcaca agaatgatgg aaacacaaac ctctacttgg    840
tttggtttca atggtactag agcagaaaat agaacataca tttattggca tggcagaagc    900
aatagaacca taattagctt aaataagtat tataatctaa caatgagatg tagaagacca    960
ggaaataaga cagtcttacc agtcaccatt atgtcagggt tggtcttcca ttcgcaaccc   1020
ataaatgaga gaccaaaaca ggcctggtgc tggtttggag gagaatggaa aaaggccatc   1080
caggaagtga aggaaccctt ggtcaaacat cccaggtata cgggaactaa taagactgaa   1140
caaattaagc taacagctcc aggaggagga gatccagaag ttactttcat gtggacaaat   1200
```

```
tgtcgaggag aattcttata ttgcaaaatg aattggtttc ttaattgggt agaagagata   1260
caaaatggtt ctagatggac aagtcaaaac cagaaagagc gacaaaggag aaattatgtg   1320
ccatgtcata ttagacagat aatcaacacg tggcacaaag taggcaaaaa tgtgtatttg   1380
cctcctaggg aaggagacct gacatgtaat tccactgtaa ctagcctcat agcagaaata   1440
gattggatca atggcaatga gaccaatatc accatgagtg cagaggtggc agaactgtat   1500
cgattggagt tgggagatta caaattagta gagattactc caattgcctt cgcccccaca   1560
agtgtaaaaa ggtacaccac aactggtgcc tcaagaaata aaagagtggt ctttgtgcta   1620
gggttcttgg gttttctcgc gacagcaggt tctgcaatgg gcgcggcgtc cgtgacgctg   1680
tcggctcagt cccggacttt gttggctggg atagtgcagc aacagcaaca gctgttggat   1740
gtggtcaaga gacaacaaga attgttgcga ctgaccgtct ggggagctaa gaacctccag   1800
actagagtca ctgctatcga gaagtaccta aaggatcagg cgcagctaaa ttcatgggga   1860
tgtgctttta ggcaggtctg ccacactact gtaccatggc caaatgacac attgacacct   1920
aactggaaca atatgacttg caagagtggg aaaaacagg tgaacttcct agaggcaaat   1980
ataactcaat cattggaaga agcacaaatt cagcaagaaa agaatacgta tgaattgcaa   2040
aaattaaata gctgggatat ttttggcaat tggtttgacc ttacttcttg gataaaatat   2100
atacaatatg gtgtactgat agttctagga gtaataggat taagaatagt gatatatgta   2160
gtgcagatgt tagctaggtt aagacagggt tataggccag tgttctcttc ccctcccgct   2220
tatgttcagc agatccctat ccagacgggc aggaactgc aaccaaaga aggagaagaa   2280 ggagacggtg gaggcagagg tggcaacaga tcttggcctt ggcagataga atatattcat   2340
ttcctgatcc gccagttgat acgcctcttg acttggctat tcagcagttg cagagattgg   2400
ctattgagga actgccaaac cctccagcca gtgctccaga gcctctcaag gacgctgcag   2460
agagcccgtg aagtcatcag agttcagata gcctacctac agtatgggtg gcgttacctc   2520
caagaagcag cgcaggcgtg gtggaaattt gtacgagaga ctcttgcaag cgcgtggaga   2580
gacttatggg agactctggg aagggttgga aggggaatac tcgcaatccc aagacgcatc   2640
aggcaagggc ttgagctcac tctcttgtga                                    2670
```

<210> SEQ ID NO 23
<211> LENGTH: 2307
<212> TYPE: DNA
<213> ORGANISM: Simian immunodeficiency virus
<220> FEATURE:
<221> NAME/KEY: misc_feature
<222> LOCATION: (0)...(0)
<223> OTHER INFORMATION: gp120 envelope (GenBank Acc. No. M29975)

<400> SEQUENCE: 23

```
atgacaaagt tcttaggaat ttttatagta ttaggaatag ggataggaat agggataagt     60
acaaaacagc agtggataac agtgttctat ggagtaccag tatggaaaaa cagctcagtc    120
caagcttttt gcatgacacc tactactagg ttgtgggcaa ctactaattg cataccagat    180
gatcatgact atacagaagt accactgaat ataacagagc catttgaagc atgggcagac    240
agaaatccct tagtagcaca agcaggaagt aacattcacc tgctgtttga acagacatta    300
aagccctgtg taaagctatc acctctatgt atcaaaatga attgtgtaga gttaaaaggc    360
tccgcaacct ctaccccagc aacctctact acggcaggaa ccaaactacc ctgtgttaga    420
aataaaacag actccaacct acagtcatgc aacgacacca tcatagaaaa ggagatgaat    480
gacgaggcag cgtcaaactg caccttttgct atggctgggt acattaggga ccaaaagaag    540
```

-continued

| | |
|---|---|
| aattactcag tagtatggaa tgatgcagaa atcttttgta agcgtagtac atcgcataat | 600 |
| gggacaaaag agtgctatat gatccactgt aatgattcag ttataaagga agcttgtgat | 660 |
| aagacatatt gggatgaatt aagactaaga tattgtgctc cagcaggata cgctttgctt | 720 |
| aaatgtaatg attgggatta tgcaggattt aagccagaat gttctaatgt ttcagtagtg | 780 |
| cattgcacaa ctttaatgaa tacaacagta accactggtc tgttattgaa tggaagctat | 840 |
| tcagaaaatc gaacccagat ctggcaaaaa catgagtga gcaatgactc agtgttaatc | 900 |
| ttgctcaata agcattataa cctgacagtt acatgcaaaa ggccagggaa taagacagtc | 960 |
| ttgccagtaa cgataatggc aggattagtc ttccactcac agaagtataa tacaagacta | 1020 |
| aggcaggcct ggtgccactt ccagggcaat tggaaaggag cttggaagga agtacaagag | 1080 |
| gaaatagtaa aattaccaaa agaacggtac caaggcacca atgatacaaa caaaatcttt | 1140 |
| ttgcaaagac aatttggaga cccagaagca gcaaatctat ggttcaactg tcaaggggaa | 1200 |
| ttcttctact gtaaaatgga ctggttttta aattatctga ataatttaac agtggatgct | 1260 |
| gatcataatc attgtaaaaa caacgcaggg aaaggtcgaa gtccaggtcc ctgtgtacag | 1320 |
| agaacttatg ttgcctgcca tatccgatct gtcataaatg attggtatac tatatcaaag | 1380 |
| aaaacatatg ctccaccaag agaaggacat tgcagtgca cgtccacagt tactgggatg | 1440 |
| acagtagagc taaactataa taaccagaac aggacaaatg taacattgag tccccagata | 1500 |
| gaaaccatct gggcggcaga attgggcaga tacaaattgg tagagattac accaattgga | 1560 |
| tttgcaccca cagaagtcag gcgatacacg ggaggccaag agaggcaaaa acgagtcccg | 1620 |
| ttcgtgctag ggttcctagg cttcttggga gctgctggga ctgcaatggg agcagcggcg | 1680 |
| acagccctga cggtccagtc tcagcattta cttgctggga tattgcagca gcagaagaat | 1740 |
| ctgctggcgg ctgtgggagc tcaacagcag atgttgaagc tgaccatttg ggtgtgaaa | 1800 |
| aacctcaatg cccgcgtcac agctcttgag aagtacctgg cggatcaggc acggttaaac | 1860 |
| gcttggggt gcgcgtggaa acaagtatgt catacaacag taccctggac gtggaataat | 1920 |
| acaccagagt ggaataatat gacctggttg gagtgggaaa acagataga aggattggag | 1980 |
| ggcaacataa caaacaatt ggaacaggca agggaacaag aggaaaagaa tttggatgct | 2040 |
| tatcaaaagt tgtcagactg gtcgagtttt tggtcttggt tcgattttc aaaatggctg | 2100 |
| aacattttaa agataggctt tttggcagta ataggcgtta tagggttaag attgctttac | 2160 |
| acattatata cttgcatagc tagggttagg cagggttact ctccttatc tcctcagatc | 2220 |
| catatccatc cgtggaaggg acagccagac aacgcaggag agccagaaga aggtggaaga | 2280 |
| acaggcaaaa gcaaatctac gcattag | 2307 |

<210> SEQ ID NO 24
<211> LENGTH: 2640
<212> TYPE: DNA
<213> ORGANISM: Simian immunodeficiency virus
<220> FEATURE:
<221> NAME/KEY: misc_feature
<222> LOCATION: (0)...(0)
<223> OTHER INFORMATION: gp120 envelope (GenBank Acc. No. U58991)

<400> SEQUENCE: 24

| | |
|---|---|
| atgggaccat taaggggaaa agggggtatta ttagtaattt tgggattaag cttaatagga | 60 |
| ctgttatatg ggacacagta tattacagtg ttttatggta tcccagtatg gaaaaacagc | 120 |
| tcagtgcaag ctttctgtat gacacctaat accaacctttt gggcaacaac taattgtata | 180 |
| ccagatgatc atgattatac tgaagtacag ttaaatgtct ctgagaaatt tgaagcatgg | 240 |

```
aaggacagga atccattagt ggcacaggcg gagagtaaca tacatttgct ctttgaaagc      300
actctgaagc catgcgtaaa actgacacct atgtgcataa agatgaattg tactaaatta      360
acaagtaccg cccctacatc aagtacccct acatcaagca gcactacgga tccctgtcca      420
aataccgacg aaagtagctg taacgccacc ttagttacaa atagcatgga ttatgagaat      480
agttctatat gctcctttgc tatggcagga tataggagag atgtaaaaaa gaaatataat      540
agtacttggt atgatcagga gttggtatgt gagaaggaaa acaacaccac aggcacgaga      600
ggttgttaca tgattcactg caacgactct gtaataaaag aagcttgtga gaaaacttat      660
tgggatacct taagattaag atactgtgca ccagcaggct ttgctatctt aaaatgtaag      720
gatactaatt atacaggatt tggtgtttgt agaaatgttt cagtagttag ttgtactgga      780
ttgatgaata ctacagtgag ctcagcattt ggcataaatg gcagtcaggc agaaaacaga      840
acagaaatat ggcaaaagca tggagtgagc aataattctg tgataataaa actaaataaa      900
cattataagt tgaagatagt gtgtagaaga ccaggaaata agacagtctt accagtaacc      960
atcatggcag gtctcgtgtt ccactcacaa caatataata caaaattaag acaagcatgg     1020
tgccatttcc agggtgattg gaaaggagcc tggaggaaag tgagaaaaac aatagtggag     1080
cttccaaaag agaaatatcg agggacaaat aacacaaggc agatttggct aagtagacaa     1140
tggggagatc cagaagcagc taacatttgg ctcaattgcc aaggagagtt tttctattgt     1200
actcctgatt ggtttgttaa ttggctgaat aatgagtcta atagtggaag aaatgtagat     1260
gtagaaggta ataattgcac cactggaaag gataaacgct gctacaaaag gacatatgtc     1320
ccctgccata ttaggtcaat tgtcaatgac tggtacacgc tcagtaagaa aacctatgca     1380
ccaccaaggg aaggacactt agaatgcaca tcaacagtga catctatgat ggtatcactg     1440
gattataaca gcaaagaaag gactaatgtg acattgacag ctaatttgga gaacatatgg     1500
gcttatgaat tgggaagata taagctcata gaaattgaac caatcggttt cgcgccaaca     1560
gagataagaa gatatgttgg gccaactcga gaaaagaggg tgcccttcgt gttggggttc     1620
ctaggctttt tgggggcagc tggagctgca atgggtgcaa cagcgacagc gttgacggtc     1680
cagtcccagc aattacttgc agggatattg cagcagcaga gaatctgctg gcggcagtt     1740 gagcagcagc agcagatgct aaagctcacc atttggggtg tgaaaaacct caatgcccgc     1800
gtcactgccc ttgaaaaata cctagaggat cagacacggc taaatttgtg gggatgtgca     1860
ttcaaacagg tgtgtcacac tacggtgccg tggactttca acaatacacc agactgggac     1920
aatatgacct ggcaggaatg ggagagccaa ataactgcct tggaaggaaa tattagtact     1980
actcttgtca aagcatatga gcaagagcag aaaaatatgg atacttatca aaagttaggt     2040
gattggactt cttggtggaa catctttgac gtctcatcat ggttctggtg gattaaatgg     2100 ggatttata tagtaatagg acttatattg tttaggatgg cttggcttat tgggggatgc     2160
atagctaggg ttaggcaggg ttactttcct ttgtctcctc agatcaatat ccgcctgggg     2220
agggaacagc cagacaacgc aggaggagaa gacaaagatt ccagcagcag cagagacaag     2280
tcgccgccct cagtgaaaga atctttattg cccaacagag gagggatcca agcggaggag     2340
agagcttggc ggcagcattt gaccaattgg tgcttgacaa tcagcagttg gttattgaga     2400
ctttaccaga tcctccgcag gagcctcacg actcttcttc aactgcttag acaggagtgc     2460
caatacattc agtatgggtg gcagcaattc aaagagggag cagcaaggtc ttttgaggct     2520
ttggcgagcg ctgcgcaaag cgccagtcgt acgctatgga atgcttgcag atccgcttat     2580
cgggcaatcc tcgaacatcc aagaagaatg cgacaagaac tggaacggtg gttcaactag     2640
```

<210> SEQ ID NO 25
<211> LENGTH: 1032
<212> TYPE: DNA
<213> ORGANISM: Human Immunodeficiency Virus
<220> FEATURE:
<221> NAME/KEY: misc_feature
<222> LOCATION: (0)...(0)
<223> OTHER INFORMATION: gp41 from HIV-2 7312A

<400> SEQUENCE: 25

```
ggtgtattcg tgctagggtt cttgggtttt ctcacgacag caggagctgc aatgggcgcg      60
gcgtccttga cgctgtcggc tcagtctcgg actttactgg ccgggatagt gcagcaacag     120
caacagctgt tagacgtggt caagagacaa caagaaatgt tgcgactgac cgtctgggga     180
acaaaaaatc tccaggcaag agtcactgct attgagaaat acttaaagga ccaggcgcaa     240
ctaaattcat ggggatgtgc gtttaggcaa gtctgccaca ctactgtacc atgggtaaat     300
gacagcttga cacctgattg gacaacatg acgtggcaac aatgggaaaa acaaatccgc     360
gacctggagg caaatatcag tgaaagtcta gaacaggcac aaatccagca agaaaagaac     420
atgtatgaat acaaaaaatt aaatagctgg gatgttttg caactggtt tgatttagcc     480
tcctgggtca atatattca gtatggagtt tatatagtag taggaatagt agctctcaga     540
gtaataatat atgtagtaca atgataggt agacttagaa gaggctatag gcctgttttc     600
tcttcccccc ccggttactt ccaacagatc cgtatccaca aggaccagga acagccagcc     660
aacgaagaaa cagaagaagg aggtggaaac gacgggggct acagatcttg gcctggcag     720
atcgaataca tccacttcct aattcgccag ctgaggaacc tcttgatttg ctatacgac     780
ggctgcagaa ccttactgtt gaagaccttc caaaccctcc aaccagctct ccaaccactc     840
aggctcctgt ttgcgtacct ccaatatggg atcggctggt ccaagaagc agtccaagca     900
gcagcggggg ctacgggaga gactcttgcg agcacaggga ggaccttatg ggaggctctc     960
aggaggacgg cgaggggaat catcgcagtc cccagaagaa tcagacaggg gcttgaactc    1020
gccctcctgt ga                                                        1032
```

<210> SEQ ID NO 26
<211> LENGTH: 1032
<212> TYPE: DNA
<213> ORGANISM: Artificial Sequence
<220> FEATURE:
<223> OTHER INFORMATION: chimeric polynucleotide comprising the
      nucleotide sequence encoding gp41 from HIV-2 7312A and a
      heterologous MPER epitope from HIV-1 (construct C1
      of Figure 7)
<221> NA

```
                  Gln Ala Arg Val Thr Ala Ile Glu Lys Tyr Leu Lys Asp Gln Ala Gln
                  65                  70                  75                  80 cta aat tca tgg gga tgt gcg ttt agg caa gtc tgc cac act act gta    288
Leu Asn Ser Trp Gly Cys Ala Phe Arg Gln Val Cys His Thr Thr Val
                85                  90                  95 cca tgg gta aat gac agc ttg aca cct gat tgg gac aac atg acg tgg    336
Pro Trp Val Asn Asp Ser Leu Thr Pro Asp Trp Asp Asn Met Thr Trp
            100                 105                 110 caa caa tgg gaa aaa caa atc cgc gac ctg gag gca aat atc agt gaa    384
Gln Gln Trp Glu Lys Gln Ile Arg Asp Leu Glu Ala Asn Ile Ser Glu
        115                 120                 125 agt cta gaa cag gca caa atc cag caa gaa aag aac atg tat gaa tta    432
Ser Leu Glu Gln Ala Gln Ile Gln Gln Glu Lys Asn Met Tyr Glu Leu
    130                 135                 140 ttg gca tta gat aaa tgg gca agt ttg tgg aat tgg ttt gac ata aca    480
Leu Ala Leu Asp Lys Trp Ala Ser Leu Trp Asn Trp Phe Asp Ile Thr
145                 150                 155                 160 aaa tgg ctg tgg tat ata aaa tat ggc gtc tat ata gta gta gga ata    528
Lys Trp Leu Trp Tyr Ile Lys Tyr Gly Val Tyr Ile Val Val Gly Ile
                165                 170                 175 gta gct ctc aga gta ata ata tat gta gta caa atg ata ggt aga ctt    576
Val Ala Leu Arg Val Ile Ile Tyr Val Val Gln Met Ile Gly Arg Leu
            180                 185                 190 aga aga ggc tat agg cct gtt ttc tct tcc ccc ccc ggt tac ttc caa    624
Arg Arg Gly Tyr Arg Pro Val Phe Ser Ser Pro Pro Gly Tyr Phe Gln
        195                 200                 205 cag atc cgt atc cac aag gac cag gaa cag cca gcc aac gaa gaa aca    672
Gln Ile Arg Ile His Lys Asp Gln Glu Gln Pro Ala Asn Glu Glu Thr
    210                 215                 220 gaa gaa gga ggt gga aac gac ggg ggc tac aga tct tgg ccc tgg cag    720
Glu Glu Gly Gly Gly Asn Asp Gly Gly Tyr Arg Ser Trp Pro Trp Gln
225                 230                 235                 240 atc gaa tac atc cac ttc cta att cgc cag ctg agg aac ctc ttg att    768
Ile Glu Tyr Ile His Phe Leu Ile Arg Gln Leu Arg Asn Leu Leu Ile
                245                 250                 255 tgg cta tac gac ggc tgc aga acc tta ctg ttg aag acc ttc caa acc    816
Trp Leu Tyr Asp Gly Cys Arg Thr Leu Leu Leu Lys Thr Phe Gln Thr
            260                 265                 270 ctc caa cca gct ctc caa cca ctc agg ctc ctg ttt gcg tac ctc caa    864
Leu Gln Pro Ala Leu Gln Pro Leu Arg Leu Leu Phe Ala Tyr Leu Gln
        275                 280                 285 tat ggg atc ggc tgg ttc caa gaa gca gtc caa gca gca gcg ggg gct    912
Tyr Gly Ile Gly Trp Phe Gln Glu Ala Val Gln Ala Ala Ala Gly Ala
    290                 295                 300 acg gga gag act ctt gcg agc aca ggg agg acc tta tgg gag gct ctc    960
Thr Gly Glu Thr Leu Ala Ser Thr Gly Arg Thr Leu Trp Glu Ala Leu
305                 310                 315                 320 agg agg acg gcg agg gga atc atc gca gtc ccc aga aga atc aga cag   1008
Arg Arg Thr Ala Arg Gly Ile Ile Ala Val Pro Arg Arg Ile Arg Gln
                325                 330                 335 ggg ctt gaa ctc gcc ctc ctg tga                                   1032
Gly Leu Glu Leu Ala Leu Leu *
            340

<210> SEQ ID NO 27
<211> LENGTH: 343
<212> TYPE: PRT
<213> ORGANISM: Artificial Sequence
<220> FEATURE:
<223> OTHER INFORMATION: chimeric polypeptide comprising gp41 from HIV-2
      7312A and a heterologous MPER epitope from HIV-1
      (construct C1 of Figure 7)
```

<400> SEQUENCE: 27

```
Gly Val Phe Val Leu Gly Phe Leu Gly Phe Leu Thr Thr Ala Gly Ala
1               5                   10                  15

Ala Met Gly Ala Ala Ser Leu Thr Leu Ser Ala Gln Ser Arg Thr Leu
            20                  25                  30

Leu Ala Gly Ile Val Gln Gln Gln Gln Leu Leu Asp Val Val Lys
        35                  40                  45

Arg Gln Gln Glu Met Leu Arg Leu Thr Val Trp Gly Thr Lys Asn Leu
50                  55                  60

Gln Ala Arg Val Thr Ala Ile Glu Lys Tyr Leu Lys Asp Gln Ala Gln
65                  70                  75                  80

Leu Asn Ser Trp Gly Cys Ala Phe Arg Gln Val Cys His Thr Thr Val
                85                  90                  95

Pro Trp Val Asn Asp Ser Leu Thr Pro Asp Trp Asp Asn Met Thr Trp
            100                 105                 110

Gln Gln Trp Glu Lys Gln Ile Arg Asp Leu Glu Ala Asn Ile Ser Glu
            115                 120                 125

Ser Leu Glu Gln Ala Gln Ile Gln Gln Glu Lys Asn Met Tyr Glu Leu
130                 135                 140

Leu Ala Leu Asp Lys Trp Ala Ser Leu Trp Asn Trp Phe Asp Ile Thr
145                 150                 155                 160

Lys Trp Leu Trp Tyr Ile Lys Tyr Gly Val Tyr Ile Val Val Gly Ile
                165                 170                 175

Val Ala Leu Arg Val Ile Ile Tyr Val Val Gln Met Ile Gly Arg Leu
            180                 185                 190

Arg Arg Gly Tyr Arg Pro Val Phe Ser Ser Pro Pro Gly Tyr Phe Gln
            195                 200                 205

Gln Ile Arg Ile His Lys Asp Gln Glu Gln Pro Ala Asn Glu Glu Thr
210                 215                 220

Glu Glu Gly Gly Gly Asn Asp Gly Gly Tyr Arg Ser Trp Pro Trp Gln
225                 230                 235                 240

Ile Glu Tyr Ile His Phe Leu Ile Arg Gln Leu Arg Asn Leu Leu Ile
                245                 250                 255

Trp Leu Tyr Asp Gly Cys Arg Thr Leu Leu Leu Lys Thr Phe Gln Thr
            260                 265                 270

Leu Gln Pro Ala Leu Gln Pro Leu Arg Leu Leu Phe Ala Tyr Leu Gln
            275                 280                 285

Tyr Gly Ile Gly Trp Phe Gln Glu Ala Val Gln Ala Ala Gly Ala
290                 295                 300

Thr Gly Glu Thr Leu Ala Ser Thr Gly Arg Thr Leu Trp Glu Ala Leu
305                 310                 315                 320

Arg Arg Thr Ala Arg Gly Ile Ile Ala Val Pro Arg Arg Ile Arg Gln
                325                 330                 335

Gly Leu Glu Leu Ala Leu Leu
            340
```

<210> SEQ ID NO 28
<211> LENGTH: 1032
<212> TYPE: DNA
<213> ORGANISM: Artificial Sequence
<220> FEATURE:
<223> OTHER INFORMATION: chimeric polynucleotide comprising the nucleotide sequence encoding gp41 from HIV-2 7312A and a heterologous MPER epitope from HIV-1 (construct C2 of Figure 7)
<221> NAME/KEY: CDS

<222> LOCATION: (1)...(1032)

<400> SEQUENCE: 28

| | | | | | | | | | | | | | | | | |
|---|---|---|---|---|---|---|---|---|---|---|---|---|---|---|---|---|
| ggt | gta | ttc | gtg | cta | ggg | ttc | ttg | ggt | ttt | ctc | acg | aca | gca | gga | gct | 48 |
| Gly | Val | Phe | Val | Leu | Gly | Phe | Leu | Gly | Phe | Leu | Thr | Thr | Ala | Gly | Ala | |
| 1 | | | | 5 | | | | | 10 | | | | | 15 | | |
| gca | atg | ggc | gcg | gcg | tcc | ttg | acg | ctg | tcg | gct | cag | tct | cgg | act | tta | 96 |
| Ala | Met | Gly | Ala | Ala | Ser | Leu | Thr | Leu | Ser | Ala | Gln | Ser | Arg | Thr | Leu | |
| | | 20 | | | | | 25 | | | | | 30 | | | | |
| ctg | gcc | ggg | ata | gtg | cag | caa | cag | caa | cag | ctg | tta | gac | gtg | gtc | aag | 144 |
| Leu | Ala | Gly | Ile | Val | Gln | Gln | Gln | Gln | Gln | Leu | Leu | Asp | Val | Val | Lys | |
| | | | 35 | | | | | 40 | | | | | 45 | | | |
| aga | caa | caa | gaa | atg | cga | ctg | acc | gtc | tgg | gga | aca | aaa | aat | ctc | | 192 |
| Arg | Gln | Gln | Glu | Met | Arg | Leu | Thr | Val | Trp | Gly | Thr | Lys | Asn | Leu | | |
| | 50 | | | | | 55 | | | | | 60 | | | | | |
| cag | gca | aga | gtc | act | gct | att | gag | aaa | tac | tta | aag | gac | cag | gcg | caa | 240 |
| Gln | Ala | Arg | Val | Thr | Ala | Ile | Glu | Lys | Tyr | Leu | Lys | Asp | Gln | Ala | Gln | |
| 65 | | | | | 70 | | | | | 75 | | | | | 80 | |
| cta | aat | tca | tgg | gga | tgt | gcg | ttt | agg | caa | gtc | tgc | cac | act | act | gta | 288 |
| Leu | Asn | Ser | Trp | Gly | Cys | Ala | Phe | Arg | Gln | Val | Cys | His | Thr | Thr | Val | |
| | | | | 85 | | | | | 90 | | | | | 95 | | |
| cca | tgg | gta | aat | gac | agc | ttg | aca | cct | gat | tgg | gac | aac | atg | acg | tgg | 336 |
| Pro | Trp | Val | Asn | Asp | Ser | Leu | Thr | Pro | Asp | Trp | Asp | Asn | Met | Thr | Trp | |
| | | | 100 | | | | | 105 | | | | | 110 | | | |
| caa | caa | tgg | gaa | aaa | caa | atc | cgc | gac | ctg | gag | gca | aat | atc | agt | gaa | 384 |
| Gln | Gln | Trp | Glu | Lys | Gln | Ile | Arg | Asp | Leu | Glu | Ala | Asn | Ile | Ser | Glu | |
| | | 115 | | | | | 120 | | | | | 125 | | | | |
| agt | cta | gaa | cag | gca | caa | atc | cag | caa | gaa | aag | aac | atg | tat | gaa | tta | 432 |
| Ser | Leu | Glu | Gln | Ala | Gln | Ile | Gln | Gln | Glu | Lys | Asn | Met | Tyr | Glu | Leu | |
| | 130 | | | | | 135 | | | | | 140 | | | | | |
| caa | gca | tta | gat | aaa | tgg | gca | agt | ttg | tgg | aat | tgg | ttt | gac | ata | aca | 480 |
| Gln | Ala | Leu | Asp | Lys | Trp | Ala | Ser | Leu | Trp | Asn | Trp | Phe | Asp | Ile | Thr | |
| 145 | | | | | 150 | | | | | 155 | | | | | 160 | |
| aaa | tgg | ctg | tgg | tat | ata | aaa | tat | ggc | gtc | tat | ata | gta | gta | gga | ata | 528 |
| Lys | Trp | Leu | Trp | Tyr | Ile | Lys | Tyr | Gly | Val | Tyr | Ile | Val | Val | Gly | Ile | |
| | | | | 165 | | | | | 170 | | | | | 175 | | |
| gta | gct | ctc | aga | gta | ata | ata | tat | gta | gta | caa | atg | ata | ggt | aga | ctt | 576 |
| Val | Ala | Leu | Arg | Val | Ile | Ile | Tyr | Val | Val | Gln | Met | Ile | Gly | Arg | Leu | |
| | | | 180 | | | | | 185 | | | | | 190 | | | |
| aga | aga | ggc | tat | agg | cct | gtt | ttc | tct | tcc | ccc | ccc | ggt | tac | ttc | caa | 624 |
| Arg | Arg | Gly | Tyr | Arg | Pro | Val | Phe | Ser | Ser | Pro | Pro | Gly | Tyr | Phe | Gln | |
| | | 195 | | | | | 200 | | | | | 205 | | | | |
| cag | atc | cgt | atc | cac | aag | gac | cag | gaa | cag | cca | gcc | aac | gaa | gaa | aca | 672 |
| Gln | Ile | Arg | Ile | His | Lys | Asp | Gln | Glu | Gln | Pro | Ala | Asn | Glu | Glu | Thr | |
| | 210 | | | | | 215 | | | | | 220 | | | | | |
| gaa | gaa | gga | ggt | gga | aac | gac | ggg | ggc | tac | aga | tct | tgg | ccc | tgg | cag | 720 |
| Glu | Glu | Gly | Gly | Gly | Asn | Asp | Gly | Gly | Tyr | Arg | Ser | Trp | Pro | Trp | Gln | |
| 225 | | | | | 230 | | | | | 235 | | | | | 240 | |
| atc | gaa | tac | atc | cac | ttc | cta | att | cgc | cag | ctg | agg | aac | ctc | ttg | att | 768 |
| Ile | Glu | Tyr | Ile | His | Phe | Leu | Ile | Arg | Gln | Leu | Arg | Asn | Leu | Leu | Ile | |
| | | | | 245 | | | | | 250 | | | | | 255 | | |
| tgg | cta | tac | gac | ggc | tgc | aga | acc | tta | ctg | ttg | aag | acc | ttc | caa | acc | 816 |
| Trp | Leu | Tyr | Asp | Gly | Cys | Arg | Thr | Leu | Leu | Leu | Lys | Thr | Phe | Gln | Thr | |
| | | | 260 | | | | | 265 | | | | | 270 | | | |
| ctc | caa | cca | gct | ctc | caa | cca | ctc | agg | ctc | ctg | ttt | gcg | tac | ctc | caa | 864 |
| Leu | Gln | Pro | Ala | Leu | Gln | Pro | Leu | Arg | Leu | Leu | Phe | Ala | Tyr | Leu | Gln | |
| | | 275 | | | | | 280 | | | | | 285 | | | | |
| tat | ggg | atc | ggc | tgg | ttc | caa | gaa | gca | gtc | caa | gca | gca | gcg | ggg | gct | 912 |
| Tyr | Gly | Ile | Gly | Trp | Phe | Gln | Glu | Ala | Val | Gln | Ala | Ala | Ala | Gly | Ala | |
| | 290 | | | | | 295 | | | | | 300 | | | | | |

```
acg gga gag act ctt gcg agc aca ggg agg acc tta tgg gag gct ctc      960
Thr Gly Glu Thr Leu Ala Ser Thr Gly Arg Thr Leu Trp Glu Ala Leu
305                 310                 315                 320 agg agg acg gcg agg gga atc atc gca gtc ccc aga aga atc aga cag     1008
Arg Arg Thr Ala Arg Gly Ile Ile Ala Val Pro Arg Arg Ile Arg Gln
                325                 330                 335 ggg ctt gaa ctc gcc ctc ctg tga                                     1032
Gly Leu Glu Leu Ala Leu Leu *
                340
```

<210> SEQ ID NO 29
<211> LENGTH: 343
<212> TYPE: PRT
<213> ORGANISM: Artificial Sequence
<220> FEATURE:
<223> OTHER INFORMATION: chimeric polypeptide encoding gp41 from HIV-2
      7312A

```
Thr Gly Glu Thr Leu Ala Ser Thr Gly Arg Thr Leu Trp Glu Ala Leu
305                 310                 315                 320

Arg Arg Thr Ala Arg Gly Ile Ile Ala Val Pro Arg Arg Ile Arg Gln
            325                 330                 335

Gly Leu Glu Leu Ala Leu Leu
            340
```

<210> SEQ ID NO 30
<211> LENGTH: 1032
<212> TYPE: DNA
<213> ORGANISM: Artificial Sequence
<220> FEATURE:
<223> OTHER INFORMATION: chimeric polynucleotide comprising the
      nucleotide sequence encoding gp41 from HIV-2 7312A and a
      heterologous MPER epitope from HIV-1 (construct C3
      of Figure 7)
<221> NAME/KEY: CDS
<222> LOCATION: (1)...(1032)

<400> SEQUENCE: 30

```
ggt gta ttc gtg cta ggg ttc ttg ggt ttt ctc acg aca gca gga gct      48
Gly Val Phe Val Leu Gly Phe Leu Gly Phe Leu Thr Thr Ala Gly Ala
1               5                   10                  15 gca atg ggc gcg gcg tcc ttg acg ctg tcg gct cag tct cgg act tta      96
Ala Met Gly Ala Ala Ser Leu Thr Leu Ser Ala Gln Ser Arg Thr Leu
            20                  25                  30 ctg gcc ggg ata gtg cag caa cag caa cag ctg tta gac gtg gtc aag     144
Leu Ala Gly Ile Val Gln Gln Gln Gln Gln Leu Leu Asp Val Val Lys
        35                  40                  45 aga caa caa gaa atg ttg cga ctg acc gtc tgg gga aca aaa aat ctc     192
Arg Gln Gln Glu Met Leu Arg Leu Thr Val Trp Gly Thr Lys Asn Leu
 50                  55                  60 cag gca aga gtc act gct att gag aaa tac tta aag gac cag gcg caa     240
Gln Ala Arg Val Thr Ala Ile Glu Lys Tyr Leu Lys Asp Gln Ala Gln
65                  70                  75                  80 cta aat tca tgg gga tgt gcg ttt agg caa gtc tgc cac act act gta     288
Leu Asn Ser Trp Gly Cys Ala Phe Arg Gln Val Cys His Thr Thr Val
                85                  90                  95 cca tgg gta aat gac agc ttg aca cct gat tgg gac aac atg acg tgg     336
Pro Trp Val Asn Asp Ser Leu Thr Pro Asp Trp Asp Asn Met Thr Trp
            100                 105                 110 caa caa tgg gaa aaa caa atc cgc gac ctg gag gca aat atc agt gaa     384
Gln Gln Trp Glu Lys Gln Ile Arg Asp Leu Glu Ala Asn Ile Ser Glu
        115                 120                 125 agt cta gaa cag gca caa atc cag caa gaa aag aac atg tat gaa tta     432
Ser Leu Glu Gln Ala Gln Ile Gln Gln Glu Lys Asn Met Tyr Glu Leu
    130                 135                 140 caa gca tta gat aaa tgg gca agt ttg tgg aat tgg ttt gac ata aca     480
Gln Ala Leu Asp Lys Trp Ala Ser Leu Trp Asn Trp Phe Asp Ile Thr
145                 150                 155                 160 aaa tgg ctg tgg tat ata aaa tat ggc gtc tat ata gta gta gga ata     528
Lys Trp Leu Trp Tyr Ile Lys Tyr Gly Val Tyr Ile Val Val Gly Ile
                165                 170                 175 gta gct ctc aga gta ata ata tat gta gta caa atg ata ggt aga ctt     576
Val Ala Leu Arg Val Ile Ile Tyr Val Val Gln Met Ile Gly Arg Leu
            180                 185                 190 aga aga ggc tat agg cct gtt ttc tct tcc ccc ccc ggt tac ttc caa     624
Arg Arg Gly Tyr Arg Pro Val Phe Ser Ser Pro Pro Gly Tyr Phe Gln
        195                 200                 205 cag atc cgt atc cac aag gac cag gaa cag cca gcc aac gaa gaa aca     672
Gln Ile Arg Ile His Lys Asp Gln Glu Gln Pro Ala Asn Glu Glu Thr
    210                 215                 220
```

```
gaa gaa gga ggt gga aac gac ggg ggc tac aga tct tgg ccc tgg cag      720
Glu Glu Gly Gly Gly Asn Asp Gly Gly Tyr Arg Ser Trp Pro Trp Gln
225                 230                 235                 240 atc gaa tac atc cac ttc cta att cgc cag ctg agg aac ctc ttg att      768
Ile Glu Tyr Ile His Phe Leu Ile Arg Gln Leu Arg Asn Leu Leu Ile
                245                 250                 255 tgg cta tac gac ggc tgc aga acc tta ctg ttg aag acc ttc caa acc      816
Trp Leu Tyr Asp Gly Cys Arg Thr Leu Leu Leu Lys Thr Phe Gln Thr
            260                 265                 270 ctc caa cca gct ctc caa cca ctc agg ctc ctg ttt gcg tac ctc caa      864
Leu Gln Pro Ala Leu Gln Pro Leu Arg Leu Leu Phe Ala Tyr Leu Gln
        275                 280                 285 tat ggg atc ggc tgg ttc caa gaa gca gtc caa gca gca gcg ggg gct      912
Tyr Gly Ile Gly Trp Phe Gln Glu Ala Val Gln Ala Ala Ala Gly Ala
    290                 295                 300 acg gga gag act ctt gcg agc aca ggg agg acc tta tgg gag gct ctc      960
Thr Gly Glu Thr Leu Ala Ser Thr Gly Arg Thr Leu Trp Glu Ala Leu
305                 310                 315                 320 agg agg acg gcg agg gga atc atc gca gtc ccc aga aga atc aga cag     1008
Arg Arg Thr Ala Arg Gly Ile Ile Ala Val Pro Arg Arg Ile Arg Gln
                325                 330                 335 ggg ctt gaa ctc gcc ctc ctg tga                                     1032
Gly Leu Glu Leu Ala Leu Leu  *
            340
```

<210> SEQ ID NO 31
<211> LENGTH: 343
<212> TYPE: PRT
<213> ORGANISM: Artificial Sequence
<220> FEATURE:
<223> OTHER INFORMATION: chimeric polypeptide encoding gp41 from HIV-2
      7312A and a heterologous MPER epitope from HIV-1
      (construct C3 of Figure 7)

<400> SEQUENCE: 31

```
Gly Val Phe Val Leu Gly Phe Leu Gly Phe Leu Thr Thr Ala Gly Ala
1               5                   10                  15

Ala Met Gly Ala Ala Ser Leu Thr Leu Ser Ala Gln

```
Arg Arg Gly Tyr Arg Pro Val Phe Ser Ser Pro Pro Gly Tyr Phe Gln
            195                 200                 205

Gln Ile Arg Ile His Lys Asp Gln Glu Gln Pro Ala Asn Glu Glu Thr
            210                 215                 220

Glu Glu Gly Gly Gly Asn Asp Gly Gly Tyr Arg Ser Trp Pro Trp Gln
225                 230                 235                 240

Ile Glu Tyr Ile His Phe Leu Ile Arg Gln Leu Arg Asn Leu Leu Ile
            245                 250                 255

Trp Leu Tyr Asp Gly Cys Arg Thr Leu Leu Lys Thr Phe Gln Thr
            260                 265                 270

Leu Gln Pro Ala Leu Gln Pro Leu Arg Leu Leu Phe Ala Tyr Leu Gln
            275                 280                 285

Tyr Gly Ile Gly Trp Phe Gln Glu Ala Val Gln Ala Ala Ala Gly Ala
            290                 295                 300

Thr Gly Glu Thr Leu Ala Ser Thr Gly Arg Thr Leu Trp Glu Ala Leu
305                 310                 315                 320

Arg Arg Thr Ala Arg Gly Ile Ile Ala Val Pro Arg Arg Ile Arg Gln
            325                 330                 335

Gly Leu Glu Leu Ala Leu Leu
            340

<210> SEQ ID NO 32
<211> LENGTH: 1032
<212> TYPE: DNA
<213> ORGANISM: Artificial Sequence
<220> FEATURE:
<223> OTHER INFORMATION: chimeric polynucleotide comprising the
      nucleotide sequence encoding gp41 from HIV-2 7312A and a
      heterologous MPER epitope from HIV-1 (construct C4
      of Figure 7)
<221> NAME/KEY: CDS
<222> LOCATION: (1)...(1032)

<400> SEQUENCE: 32 ggt gta ttc gtg cta ggg ttc ttg ggt ttt ctc acg aca gca gga gct      48
Gly Val Phe Val Leu Gly Phe Leu Gly Phe Leu Thr Thr Ala Gly Ala
1               5                   10                  15 gca atg ggc gcg gcg tcc ttg acg ctg tcg gct cag tct cgg act tta     96
Ala Met Gly Ala Ala Ser Leu Thr Leu Ser Ala Gln Ser Arg Thr Leu
            20                  25                  30 ctg gcc ggg ata gtg cag caa cag caa cag ctg tta gac gtg gtc aag    144
Leu Ala Gly Ile Val Gln Gln Gln Gln Gln Leu Leu Asp Val Val Lys
        35                  40                  45 aga caa caa gaa atg ttg cga ctg acc gtc tgg gga aca aaa aat ctc    192
Arg Gln Gln Glu Met Leu Arg Leu Thr Val Trp Gly Thr Lys Asn Leu
50                  55                  60 cag gca aga gtc act gct att gag aaa tac tta aag gac cag gcg caa    240
Gln Ala Arg Val Thr Ala Ile Glu Lys Tyr Leu Lys Asp Gln Ala Gln
65                  70                  75                  80 cta aat tca tgg gga tgt gcg ttt agg caa gtc tgc cac act act gta    288
Leu Asn Ser Trp Gly Cys Ala Phe Arg Gln Val Cys His Thr Thr Val
                85                  90                  95 cca tgg gta aat gac agc ttg aca cct gat tgg gac aac atg acg tgg    336
Pro Trp Val Asn Asp Ser Leu Thr Pro Asp Trp Asp Asn Met Thr Trp
            100                 105                 110 caa caa tgg gaa aaa caa atc cgc gac ctg gag gca aat atc agt gaa    384
Gln Gln Trp Glu Lys Gln Ile Arg Asp Leu Glu Ala Asn Ile Ser Glu
        115                 120                 125 agt cta gaa cag gca caa atc cag caa gaa aag aac atg tat gaa tta    432
Ser Leu Glu Gln Ala Gln Ile Gln Gln Glu Lys Asn Met Tyr Glu Leu
```

```
                130                 135                 140
ttg gca tta gat aaa tgg gca agt ttg tgg aac tgg ttt gat tta gcc      480
Leu Ala Leu Asp Lys Trp Ala Ser Leu Trp Asn Trp Phe Asp Leu Ala
145                 150                 155                 160 tcc tgg gtc aaa tat att cag tat gga gtt tat ata gta gta gga ata      528
Ser Trp Val Lys Tyr Ile Gln Tyr Gly Val Tyr Ile Val Val Gly Ile
                165                 170                 175 gta gct ctc aga gta ata ata tat gta gta caa atg ata ggt aga ctt      576
Val Ala Leu Arg Val Ile Ile Tyr Val Val Gln Met Ile Gly Arg Leu
            180                 185                 190 aga aga ggc tat agg cct gtt ttc tct tcc ccc ccc ggt tac ttc caa      624
Arg Arg Gly Tyr Arg Pro Val Phe Ser Ser Pro Pro Gly Tyr Phe Gln
        195                 200                 205 cag atc cgt atc cac aag gac cag gaa cag cca gcc aac gaa gaa aca      672
Gln Ile Arg Ile His Lys Asp Gln Glu Gln Pro Ala Asn Glu Glu Thr
    210                 215                 220 gaa gaa gga ggt gga aac gac ggg ggc tac aga tct tgg ccc tgg cag      720
Glu Glu Gly Gly Gly Asn Asp Gly Gly Tyr Arg Ser Trp Pro Trp Gln
225                 230                 235                 240 atc gaa tac atc cac ttc cta att cgc cag ctg agg aac ctc ttg att      768
Ile Glu Tyr Ile His Phe Leu Ile Arg Gln Leu Arg Asn Leu Leu Ile
                245                 250                 255 tgg cta tac gac ggc tgc aga acc tta ctg ttg aag acc ttc caa acc      816
Trp Leu Tyr Asp Gly Cys Arg Thr Leu Leu Leu Lys Thr Phe Gln Thr
            260                 265                 270 ctc caa cca gct ctc caa cca ctc agg ctc ctg ttt gcg tac ctc caa      864
Leu Gln Pro Ala Leu Gln Pro Leu Arg Leu Leu Phe Ala Tyr Leu Gln
        275                 280                 285 tat ggg atc ggc tgg ttc caa gaa gca gtc caa gca gca gcg ggg gct      912
Tyr Gly Ile Gly Trp Phe Gln Glu Ala Val Gln Ala Ala Ala Gly Ala
    290                 295                 300 acg gga gag act ctt gcg agc aca ggg agg acc tta tgg gag gct ctc      960
Thr Gly Glu Thr Leu Ala Ser Thr Gly Arg Thr Leu Trp Glu Ala Leu
305                 310                 315                 320 agg agg acg gcg agg gga atc atc gca gtc ccc aga aga atc aga cag     1008
Arg Arg Thr Ala Arg Gly Ile Ile Ala Val Pro Arg Arg Ile Arg Gln
                325                 330                 335 ggg ctt gaa ctc gcc ctc ctg tga                                     1032
Gly Leu Glu Leu Ala Leu Leu *
            340
```

<210> SEQ ID NO 33
<211> LENGTH: 343
<212> TYPE: PRT
<213> ORGANISM: Artificial Sequence
<220> FEATURE:
<223> OTHER INFORMATION: chimeric polypeptide encoding gp41 from HIV-2
      7312A and a heterologous MPER epitope from HIV-1
      (construct C4 of Figure 7)

<400> SEQUENCE: 33

```
Gly Val Phe Val Leu Gly Phe Leu Gly Phe Leu Thr Thr Ala Gly Ala
1               5                   10                  15

Ala Met Gly Ala Ala Ser Leu Thr Leu Ser Ala Gln Ser Arg Thr Leu
            20                  25                  30

Leu Ala Gly Ile Val Gln Gln Gln Gln Leu Leu Asp Val Val Lys
        35                  40                  45

Arg Gln Gln Glu Met Leu Arg Leu Thr Val Trp Gly Thr Lys Asn Leu
    50                  55                  60

Gln Ala Arg Val Thr Ala Ile Glu Lys Tyr Leu Lys Asp Gln Ala Gln
65                  70                  75                  80
```

```
Leu Asn Ser Trp Gly Cys Ala Phe Arg Gln Val Cys His Thr Thr Val
                 85                  90                  95
Pro Trp Val Asn Asp Ser Leu Thr Pro Asp Trp Asp Asn Met Thr Trp
            100                 105                 110
Gln Gln Trp Glu Lys Gln Ile Arg Asp Leu Glu Ala Asn Ile Ser Glu
        115                 120                 125
Ser Leu Glu Gln Ala Gln Ile Gln Gln Glu Lys Asn Met Tyr Glu Leu
130                 135                 140
Gln Lys Leu Asn Ser Trp Asp Val Phe Gly Asn Trp Phe Asp Ile Thr
145                 150                 155                 160
Lys Trp Leu Trp Tyr Ile Lys Tyr Gly Val Tyr Ile Val Val Gly Ile
                165                 170                 175
Val Ala Leu Arg Val Ile Ile Tyr Val Val Gln Met Ile Gly Arg Leu
            180                 185                 190
Arg Arg Gly Tyr Arg Pro Val Phe Ser Ser Pro Gly Tyr Phe Gln
        195                 200                 205
Gln Ile Arg Ile His Lys Asp Gln Glu Gln Pro Ala Asn Glu Glu Thr
    210                 215                 220
Glu Glu Gly Gly Gly Asn Asp Gly Gly Tyr Arg Ser Trp Pro Trp Gln
225                 230                 235                 240
Ile Glu Tyr Ile His Phe Leu Ile Arg Gln Leu Arg Asn Leu Leu Ile
                245                 250                 255
Trp Leu Tyr Asp Gly Cys Arg Thr Leu Leu Leu Lys Thr Phe Gln Thr
            260                 265                 270
Leu Gln Pro Ala Leu Gln Pro Leu Arg Leu Leu Phe Ala Tyr Leu Gln
        275                 280                 285
Tyr Gly Ile Gly Trp Phe Gln Glu Ala Val Gln Ala Ala Ala Gly Ala
    290                 295                 300
Thr Gly Glu Thr Leu Ala Ser Thr Gly Arg Thr Leu Trp Glu Ala Leu
305                 310                 315                 320
Arg Arg Thr Ala Arg Gly Ile Ile Ala Val Pro Arg Arg Ile Arg Gln
                325                 330                 335
Gly Leu Glu Leu Ala Leu Leu
            340
```

<210> SEQ ID NO 34
<211> LENGTH: 1032
<212> TYPE: DNA
<213> ORGANISM: Artificial Sequence
<220> FEATURE:
<223> OTHER INFORMATION: chimeric polynucleotide comprising the
      nucleotide sequence encoding gp41 from HIV-2 7312A and a
      heterologous MPER epitope from HIV-1 (construct C5
      of Figure 7)
<221> NAME/KEY: CDS
<222> LOCATION: (1)...(1032)

<400> SEQUENCE: 34

```
ggt gta ttc gtg cta ggg ttc ttg ggt ttt ctc acg aca gca gga gct    48
Gly Val Phe Val Leu Gly Phe Leu Gly Phe Leu Thr Thr Ala Gly Ala
1               5                   10                  15 gca atg ggc gcg gcg tcc ttg acg ctg tcg gct cag tct cgg act tta    96
Ala Met Gly Ala Ala Ser Leu Thr Leu Ser Ala Gln Ser Arg Thr Leu
            20                  25                  30 ctg gcc ggg ata gtg cag caa cag caa ctg tta gac gtg gtc aag       144
Leu Ala Gly Ile Val Gln Gln Gln Gln Leu Leu Asp Val Val Lys
        35                  40                  45 aga caa caa gaa atg ttg cga ctg acc gtc tgg gga aca aaa aat ctc    192
```

```
Arg Gln Gln Glu Met Leu Arg Leu Thr Val Trp Gly Thr Lys Asn Leu
     50                  55                  60 cag gca aga gtc act gct att gag aaa tac tta aag gac cag gcg caa      240
Gln Ala Arg Val Thr Ala Ile Glu Lys Tyr Leu Lys Asp Gln Ala Gln
 65                  70                  75                  80 cta aat tca tgg gga tgt gcg ttt agg caa gtc tgc cac act act gta      288
Leu Asn Ser Trp Gly Cys Ala Phe Arg Gln Val Cys His Thr Thr Val
                 85                  90                  95 cca tgg gta aat gac agc ttg aca cct gat tgg gac aac atg acg tgg      336
Pro Trp Val Asn Asp Ser Leu Thr Pro Asp Trp Asp Asn Met Thr Trp
                100                 105                 110 caa caa tgg gaa aaa caa atc cgc gac ctg gag gca aat atc agt gaa      384
Gln Gln Trp Glu Lys Gln Ile Arg Asp Leu Glu Ala Asn Ile Ser Glu
            115                 120                 125 agt cta gaa cag gca caa atc cag caa gaa aag aac atg tat gaa tta      432
Ser Leu Glu Gln Ala Gln Ile Gln Gln Glu Lys Asn Met Tyr Glu Leu
        130                 135                 140 caa aaa tta aat agc tgg gat gtt ttt ggc aac tgg ttt gat ata acc      480
Gln Lys Leu Asn Ser Trp Asp Val Phe Gly Asn Trp Phe Asp Ile Thr
145                 150                 155                 160 tcc tgg gtc aaa tat att cag tat gga gtt tat ata gta gta gga ata      528
Ser Trp Val Lys Tyr Ile Gln Tyr Gly Val Tyr Ile Val Val Gly Ile
                165                 170                 175 gta gct ctc aga gta ata ata tat gta gta caa atg ata ggt aga ctt      576
Val Ala Leu Arg Val Ile Ile Tyr Val Val Gln Met Ile Gly Arg Leu
                180                 185                 190 aga aga ggc tat agg cct gtt ttc tct tcc ccc ccc ggt tac ttc caa      624
Arg Arg Gly Tyr Arg Pro Val Phe Ser Ser Pro Pro Gly Tyr Phe Gln
            195                 200                 205 cag atc cgt atc cac aag gac cag gaa cag cca gcc aac gaa gaa aca      672
Gln Ile Arg Ile His Lys Asp Gln Glu Gln Pro Ala Asn Glu Glu Thr
        210                 215                 220 gaa gaa gga ggt gga aac gac ggg ggc tac aga tct tgg ccc tgg cag      720
Glu Glu Gly Gly Gly Asn Asp Gly Gly Tyr Arg Ser Trp Pro Trp Gln
225                 230                 235                 240 atc gaa tac atc cac ttc cta att cgc cag ctg agg aac ctc ttg att      768
Ile Glu Tyr Ile His Phe Leu Ile Arg Gln Leu Arg Asn Leu Leu Ile
                245                 250                 255 tgg cta tac gac ggc tgc aga acc tta ctg ttg aag acc ttc caa acc      816
Trp Leu Tyr Asp Gly Cys Arg Thr Leu Leu Leu Lys Thr Phe Gln Thr
                260                 265                 270 ctc caa cca gct ctc caa cca ctc agg ctc ctg ttt gcg tac ctc caa      864
Leu Gln Pro Ala Leu Gln Pro Leu Arg Leu Leu Phe Ala Tyr Leu Gln
            275                 280                 285 tat ggg atc ggc tgg ttc caa gaa gca gtc caa gca gca gcg ggg gct      912
Tyr Gly Ile Gly Trp Phe Gln Glu Ala Val Gln Ala Ala Ala Gly Ala
        290                 295                 300 acg gga gag act ctt gcg agc aca ggg agg acc tta tgg gag gct ctc      960
Thr Gly Glu Thr Leu Ala Ser Thr Gly Arg Thr Leu Trp Glu Ala Leu
305                 310                 315                 320 agg agg acg gcg agg gga atc atc gca gtc ccc aga aga atc aga cag     1008
Arg Arg Thr Ala Arg Gly Ile Ile Ala Val Pro Arg Arg Ile Arg Gln
                325                 330                 335 ggg ctt gaa ctc gcc ctc ctg tga                                     1032
Gly Leu Glu Leu Ala Leu Leu *
        340

<210> SEQ ID NO 35
<211> LENGTH: 343
<212> TYPE: PRT
<213> ORGANISM: Artificial Sequence
```

<220> FEATURE:
<223> OTHER INFORMATION: chimeric polypeptide comprising the gp41 from
    HIV-2 7312A and a heterologous MPER epitope from
    HIV-1 (construct C5 of Figure 7)

<400> SEQUENCE: 35

Gly Val Phe Val Leu Gly Phe Leu Gly Phe Leu Thr Thr Ala Gly Ala
 1               5                  10                  15

Ala Met Gly Ala Ala Ser Leu Thr Leu Ser Ala Gln Ser Arg Thr Leu
             20                  25                  30

Leu Ala Gly Ile Val Gln Gln Gln Gln Leu Leu Asp Val Val Lys
         35                  40                  45

Arg Gln Gln Glu Met Leu Arg Leu Thr Val Trp Gly Thr Lys Asn Leu
 50                  55                  60

Gln Ala Arg Val Thr Ala Ile Glu Lys Tyr Leu Lys Asp Gln Ala Gln
 65                  70                  75                  80

Leu Asn Ser Trp Gly Cys Ala Phe Arg Gln Val Cys His Thr Thr Val
                 85                  90                  95

Pro Trp Val Asn Asp Ser Leu Thr Pro Asp Trp Asp Asn Met Thr Trp
             100                 105                 110

Gln Gln Trp Glu Lys Gln Ile Arg Asp Leu Glu Ala Asn Ile Ser Glu
             115                 120                 125

Ser Leu Glu Gln Ala Gln Ile Gln Gln Glu Lys Asn Met Tyr Glu Leu
 130                 135                 140

Gln Lys Leu Asn Ser Trp Asp Val Phe Gly Asn Trp Phe Asp Ile Thr
 145                 150                 155                 160

Ser Trp Val Lys Tyr Ile Gln Tyr Gly Val Tyr Ile Val Val Gly Ile
                 165                 170                 175

Val Ala Leu Arg Val Ile Ile Tyr Val Val Gln Met Ile Gly Arg Leu
             180                 185                 190

Arg Arg Gly Tyr Arg Pro Val Phe Ser Ser Pro Pro Gly Tyr Phe Gln
             195                 200                 205

Gln Ile Arg Ile His Lys Asp Gln Glu Gln Pro Ala Asn Glu Glu Thr
 210                 215                 220

Glu Glu Gly Gly Gly Asn Asp Gly Gly Tyr Arg Ser Trp Pro Trp Gln
 225                 230                 235                 240

Ile Glu Tyr Ile His Phe Leu Ile Arg Gln Leu Arg Asn Leu Leu Ile
                 245                 250                 255

Trp Leu Tyr Asp Gly Cys Arg Thr Leu Leu Leu Lys Thr Phe Gln Thr
             260                 265                 270

Leu Gln Pro Ala Leu Gln Pro Leu Arg Leu Leu Phe Ala Tyr Leu Gln
         275                 280                 285

Tyr Gly Ile Gly Trp Phe Gln Glu Ala Val Gln Ala Ala Ala Gly Ala
     290                 295                 300

Thr Gly Glu Thr Leu Ala Ser Thr Gly Arg Thr Leu Trp Glu Ala Leu
305                 310                 315                 320

Arg Arg Thr Ala Arg Gly Ile Ile Ala Val Pro Arg Arg Ile Arg Gln
                 325                 330                 335

Gly Leu Glu Leu Ala Leu Leu
             340

<210> SEQ ID NO 36
<211> LENGTH: 1032
<212> TYPE: DNA
<213> ORGANISM: Artificial Sequence
<220> FEATURE:
<223> OTHER INFORMATION: chimeric polynucleotide encoding the gp41 from -continued HIV-2 7312A and a heterologous MPER epitope from
HIV-1 (construct C6 of Figure 7)
<221> NAME/

```
Tyr Gly Ile Gly Trp Phe Gln Glu Ala Val Gln Ala Ala Gly Ala
        290                 295                 300 acg gga gag act ctt gcg agc aca ggg agg acc tta tgg gag gct ctc    960
Thr Gly Glu Thr Leu Ala Ser Thr Gly Arg Thr Leu Trp Glu Ala Leu
305                 310                 315                 320 agg agg acg gcg agg gga atc atc gca gtc ccc aga aga atc aga cag   1008
Arg Arg Thr Ala Arg Gly Ile Ile Ala Val Pro Arg Arg Ile Arg Gln
                325                 330                 335 ggg ctt gaa ctc gcc ctc ctg tga                                   1032
Gly Leu Glu Leu Ala Leu Leu *
            340
```

<210> SEQ ID NO 37
<211> LENGTH: 343
<212> TYPE: PRT
<213> ORGANISM: Artificial Sequence
<220> FEATURE:
<223> OTHER INFORMATION: chimeric polypeptide comprising the gp41 from
      HIV-2 7312A and a heterologous MPER epitope from
      HIV-1 (construct C6 of Figure 7)

<400> SEQUENCE: 37

```
Gly Val Phe Val Leu Gly Phe Leu Gly Phe Leu Thr Thr Ala Gly Ala
1               5                   10                  15

Ala Met Gly Ala Ala Ser Leu Thr Leu Ser Ala Gln Ser Arg Thr Leu
            20                  25                  30

Leu Ala Gly Ile Val Gln Gln Gln Gln Gln Leu Leu Asp Val Val Lys
        35                  40                  45

Arg Gln Gln Glu Met Leu Arg Leu Thr Val Trp Gly Thr Lys Asn Leu
    50                  55                  60

Gln Ala Arg Val Thr Ala Ile Glu Lys Tyr Leu Lys Asp Gln Ala Gln
65                  70                  75                  80

Leu Asn Ser Trp Gly Cys Ala Phe Arg Gln Val Cys His Thr Thr Val
                85                  90                  95

Pro Trp Val Asn Asp Ser Leu Thr Pro Asp Trp Asp Asn Met Thr Trp
            100                 105                 110

Gln Gln Trp Glu Lys Gln Ile Arg Asp Leu Glu Ala Asn Ile Ser Glu
        115                 120                 125

Ser Leu Glu Gln Ala Gln Ile Gln Gln Glu Lys Asn Met Tyr Glu Leu
    130                 135                 140

Gln Ala Leu Asp Lys Trp Ala Val Phe Gly Asn Trp Phe Asp Leu Ala
145                 150                 155                 160

Ser Trp Val Lys Tyr Ile Gln Tyr Gly Val Tyr Ile Val Val Gly Ile
                165                 170                 175

Val Ala Leu Arg Val Ile Ile Tyr Val Val Gln Met Ile Gly Arg Leu
            180                 185                 190

Arg Arg Gly Tyr Arg Pro Val Phe Ser Ser Pro Gly Tyr Phe Gln
        195                 200                 205

Gln Ile Arg Ile His Lys Asp Gln Glu Gln Pro Ala Asn Glu Glu Thr
    210                 215                 220

Glu Glu Gly Gly Gly Asn Asp Gly Gly Tyr Arg Ser Trp Pro Trp Gln
225                 230                 235                 240

Ile Glu Tyr Ile His Phe Leu Ile Arg Gln Leu Arg Asn Leu Leu Ile
                245                 250                 255

Trp Leu Tyr Asp Gly Cys Arg Thr Leu Leu Lys Thr Phe Gln Thr
            260                 265                 270

Leu Gln Pro Ala Leu Gln Pro Leu Arg Leu Leu Phe Ala Tyr Leu Gln
        275                 280                 285
```

```
Tyr Gly Ile Gly Trp Phe Gln Glu Ala Val Gln Ala Ala Gly Ala
    290                 295                 300

Thr Gly Glu Thr Leu Ala Ser Thr Gly Arg Thr Leu Trp Glu Ala Leu
305                 310                 315                 320

Arg Arg Thr Ala Arg Gly Ile Ile Ala Val Pro Arg Arg Ile Arg Gln
                325                 330                 335

Gly Leu Glu Leu Ala Leu Leu
            340

<210> SEQ ID NO 38
<211> LENGTH: 23
<212> TYPE: PRT
<213> ORGANISM: Human Immunodeficiency Virus
<220> FEATURE:
<221> NAME/KEY: DOMAIN
<222> LOCATION: (0)...(0)
<223> OTHER INFORMATION: Membrane Proximal External Region (MPER) of gp
      41 from HIV-1 YU2.

<400> SEQUENCE: 38

Leu Ala Leu Asp Lys Trp Ala Ser Leu Trp Asn Trp Phe Asp Ile Thr
1               5                   10                  15

Lys Trp Leu Trp Tyr Ile Lys
            20

<210> SEQ ID NO 39
<211> LENGTH: 343
<212> TYPE: PRT
<213> ORGANISM: Human Immunodeficiency Virus

<400> SEQUENCE: 39

Gly Val Phe Val Leu Gly Phe Leu Gly Phe Leu Thr Thr Ala Gly Ala
1               5                   10                  15

Ala Met Gly Ala Ala Ser Leu Thr Leu Ser Ala Gln Ser Arg Thr Leu
            20                  25                  30

Leu Ala Gly Ile Val Gln Gln Gln Gln Leu Leu Asp Val Val Lys
        35                  40                  45

Arg Gln Gln Glu Met Leu Arg Leu Thr Val Trp Gly Thr Lys Asn Leu
    50                  55                  60

Gln Ala Arg Val Thr Ala Ile Glu Lys Tyr Leu Lys Asp Gln Ala Gln
65                  70                  75                  80

Leu Asn Ser Trp Gly Cys Ala Phe Arg Gln Val Cys His Thr Thr Val
                85                  90                  95

Pro Trp Val Asn Asp Ser Leu Thr Pro Asp Trp Asp Asn Met Thr Trp
            100                 105                 110

Gln Gln Trp Glu Lys Gln Ile Arg Asp Leu Glu Ala Asn Ile Ser Glu
        115                 120                 125

Ser Leu Glu Gln Ala Gln Ile Gln Gln Glu Lys Asn Met Tyr Glu Leu
    130                 135                 140

Gln Lys Leu Asn Ser Trp Asp Val Phe Gly Asn Trp Phe Asp Leu Ala
145                 150                 155                 160

Ser Trp Val Lys Tyr Ile Gln Tyr Gly Val Tyr Ile Val Val Gly Ile
                165                 170                 175

Val Ala Leu Arg Val Ile Tyr Val Val Gln Met Ile Gly Arg Leu
            180                 185                 190

Arg Arg Gly Tyr Arg Pro Val Phe Ser Ser Pro Pro Gly Tyr Phe Gln
        195                 200                 205

Gln Ile Arg Ile His Lys Asp Gln Glu Gln Pro Ala Asn Glu Glu Thr
```

-continued

```
                210                 215                 220
Glu Glu Gly Gly Gly Asn Asp Gly Gly Tyr Arg Ser Trp Pro Trp Gln
225                 230                 235                 240

Ile Glu Tyr Ile His Phe Leu Ile Arg Gln Leu Arg Asn Leu Leu Ile
                245                 250                 255

Trp Leu Tyr Asp Gly Cys Arg Thr Leu Leu Leu Lys Thr Phe Gln Thr
                260                 265                 270

Leu Gln Pro Ala Leu Gln Pro Leu Arg Leu Leu Phe Ala Tyr Leu Gln
                275                 280                 285

Tyr Gly Ile Gly Trp Phe Gln Glu Ala Val Gln Ala Ala Ala Gly Ala
        290                 295                 300

Thr Gly Glu Thr Leu Ala Ser Thr Gly Arg Thr Leu Trp Glu Ala Leu
305                 310                 315                 320

Arg Arg Thr Ala Arg Gly Ile Ile Ala Val Pro Arg Arg Ile Arg Gln
                325                 330                 335

Gly Leu Glu Leu Ala Leu Leu
                340
```

MOLECULAR SCAFFOLDS FOR HIV-1 IMMUNOGENS

FIELD OF THE INVENTION

The invention relates to the field of retroviruses, particularly lentivirus.

BACKGROUND OF THE INVENTION

Broadly neutralizing antibodies to HIV will likely be needed if any AIDS vaccine is to prevent people from becoming infected with HIV. Most of the AIDS vaccine candidates now entering clinical trials are aimed at stimulating certain infection-fighting white blood cells, not antibodies. While these vaccines may prevent people who become infected with HIV from progressing to AIDS, they are not likely to prevent an infection in the first place. To do that, neutralizing antibodies against HIV-1 will likely be needed as well.

Given the potential anti-viral effects of neutralizing antibodies, it is not unexpected that HIV-1 has evolved multiple mechanisms to protect it from antibody binding including, for example, the heavy glycosylation of the envelope polypeptide, the trimerization of the gp120 and gp41 structure which can shield antibody access to the underlying peptide structure, and the kinetics and spatial constraints that impede antibodies from binding potentially vulnerable sites during receptor binding and membrane fusion. However, despite all of the defense mechanisms of HIV against neutralizing antibodies, primary isolates of HIV from different genetic subtypes can be neutralized by some broadly reactive human monoclonal antibodies such as b12, 2G12, 2F5, Z13, and 4E10. In addition, a few rare sera from HIV-1 infected individuals have broad neutralizing activity. The existence of such broadly neutralizing antibodies provides an indication that a vaccine inducing neutralizing antibodies can indeed be created.

Methods and compositions are needed in the art which provide immunogens that elicit neutralizing antibodies against HIV-1.

BRIEF SUMMARY OF THE INVENTION

An immunogenic composition is provided which comprises a chimeric envelope polypeptide or a functional variant thereof wherein the envelope polypeptide is from a lentivirus that is not HIV-1, and the chimeric envelope polypeptide comprises at least one heterologous epitope recognized by an HIV-1 neutralizing antibody. In specific embodiments, the envelope polypeptide is selected from the group consisting of an HIV-2 envelope polypeptide, a functional variant of the HIV-2 envelope, a Simian Immunodeficiency virus (SIV) envelope polypeptide or a functional variant of the SIV envelope polypeptide. In other embodiments, the heterologous epitope is derived from an HIV-1 envelope polypeptide.

Also provided is an immunogenic composition comprising a polynucleotide encoding a chimeric envelope polypeptide or a functional variant thereof that is not from HIV-1. The polypeptide encoded by the polynucleotide further comprises at least one heterologous epitope that is recognized by an HIV-1 neutralizing antibody. In specific embodiments, a nucleotide sequence encoding the chimeric envelope polypeptide encodes an HIV-2 envelope polypeptide, a functional variant of the HIV-2 envelope polypeptide, a Simian Immunodeficiency virus (SIV) envelope polypeptide, or a functional variant of the SIV envelope polypeptide. In specific embodiments, the heterologous epitope is derived from an HIV-1 envelope polypeptide.

In further compositions, the heterologous epitope recognized by the HIV-1 neutralizing antibody is from the gp41 polypeptide, the gp120 polypeptide, the membrane proximal external region of gp41, or the variable loop region of gp120. In still other compositions, the heterologous epitope comprises a 4E10 epitope, a Z13 epitope, or a 2F5 epitope.

The immunogenic compositions of the invention can further comprise a pharmaceutically acceptable carrier, diluent, or adjuvant. In addition, in specific embodiments, the immunogenic composition comprises a vaccine.

A method for eliciting an immune response in a subject is provided. The method comprises introducing into a subject an effective concentration of the immunogenic composition of the invention. Further provided is a method for generating antibodies specific for a chimeric polypeptide of the invention. The method comprises introducing into a subject an effective concentration of an immunogenic composition of the invention. Additional methods are provided for inhibiting or preventing infection by HIV-1 in a subject. Such a method comprises administering to the subject an effective amount of an immunogenic composition of the invention.

BRIEF DESCRIPTION OF FIGURES

FIG. 1 shows the envelope gp120 alignments for HIV-2 (7312A (SEQ ID NO:2) and UC1 (SEQ ID NO:7)), SIV (Mac239 (SEQ ID NO:11) and Ver-TyO1 (SEQ ID NO:12)), and HIV-1 (YU2 (SEQ ID NO:13) and HXB2 (SEQ ID NO:10)). Bridging sheet, variable loops, amino acid identities, and site-directed mutations (H419R, Q422L, and V434M) are indicated. The signal peptide-gp120 cleavage position for HIV-1 is shown. Variable loops (V1/V2, V3, and V4) have conventionally been defined by disulfide-linked cysteine residues at their bases, as depicted. However, the actual limits of variable loops have been resolved structurally in the HXB2-CD4-17b crystal complex (Kwong (1998) *Nature* 393:648-659), and these sequences are indicated by green bars. It is possible that structural details diverge in the more distantly related HIV/SIV sequences. The amino acids contributing to the bridging sheet are highlighted. Circles indicate residues contributing to chemokine co-receptor binding based on site-directed mutagenesis studies (Rizzuto (1998) *Science* 280:1949-1953; Rizzuto (2000) *AIDS Res Hum Retroviruses* 16:741-749). Additional amino acids within the stem of V3, including 298R, 301N, 303T, 3231, 325N, 326M and 327R, may contribute to gp120 interaction with CCR5 (Cormier (2001) *J Virol* 75:5541-5549). Triangles indicate HIV-1 contact residues for CD4 based on crystal structure analyses (Kwong (1998) *Nature* 393:648-659). Asterisks below the sequence indicate conservation of amino acid identity across all five virus strains. Overall gp120 sequence identity was calculated based on amino acid residues exclusive of the initiator methionine of the (cleaved) signal peptide and a gap-stripped alignment of the sequences shown. Except for SIVverTYO1, sequences were obtained from the *HIV Sequence Compendium* 2002 (*HIV Sequence Compendium* (2002) Kuiken et al. Eds. Los Alamos National Laboratory, Los Alamos, N. Mex., LA-UR 03-3564). We determined experimentally the nucleotide sequence of the SIVverTYO1 clone used in our studies (lambda phage SAH12) and found that it differed from the reported sequence of the same clone in the Compendium at positions 171(−), 172(N), 402(D), 418(C) and 427(W).

FIG. 2 shows the complete sequences for thirty-one gp160 envelope clones of plasma virus from subject SUMA0874 with V3 region indicated. Clones are identified according to the day following onset of symptoms of the acute retroviral syndrome the plasma sample was obtained (e.g., S004-11 refers to clone number 04 from a plasma sample taken 11 days following symptom onset, a point when the patient was viral RNA positive and viral antibody negative by ELISA and immunoblot). A subset of the clones depicted was analyzed previously in a study of neutralizing antibody escape (Wei et al. (2003) *Nature* 422:307-312). Four additional gp160 sequences depicted correspond to wild-type clones S736-68 and S736-73 that were modified by site-directed mutagenesis to contain substitutions at the 308 or 309 positions. These are designated S736-68 nm/T1, S736-68 m/P1, S736-73 m/TT, and S736-73 m/PI. The critical amino acid substitution at position 309 (isoleucine to threonine) in clones S736-68 and S736-75 responsible for spontaneous co-receptor exposure is highlighted in yellow as is the site-directed mutation made in the wild-type clone S736-73 (S736-73 m/TT).

Figures 1, 2:
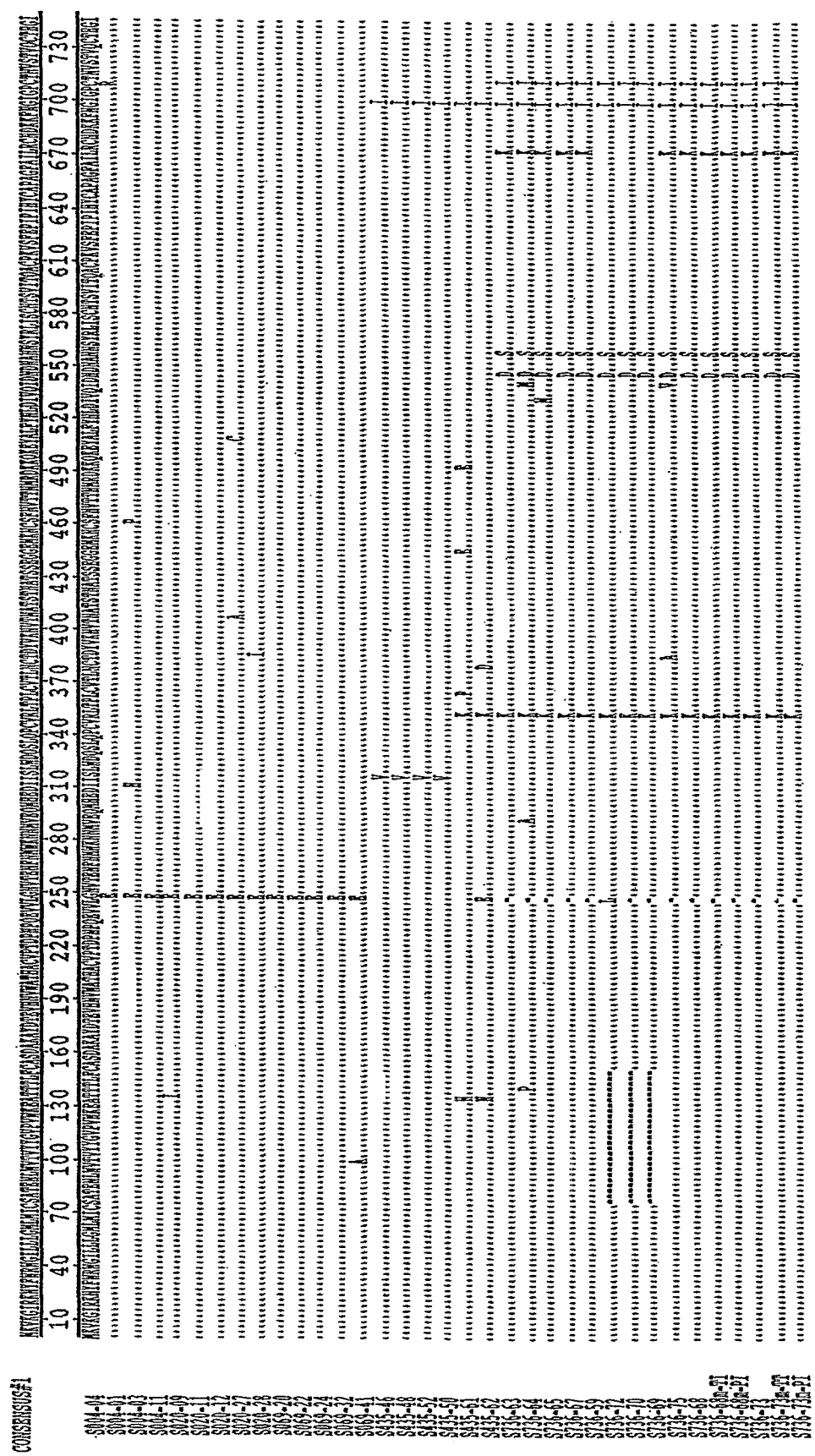
Figure 2:
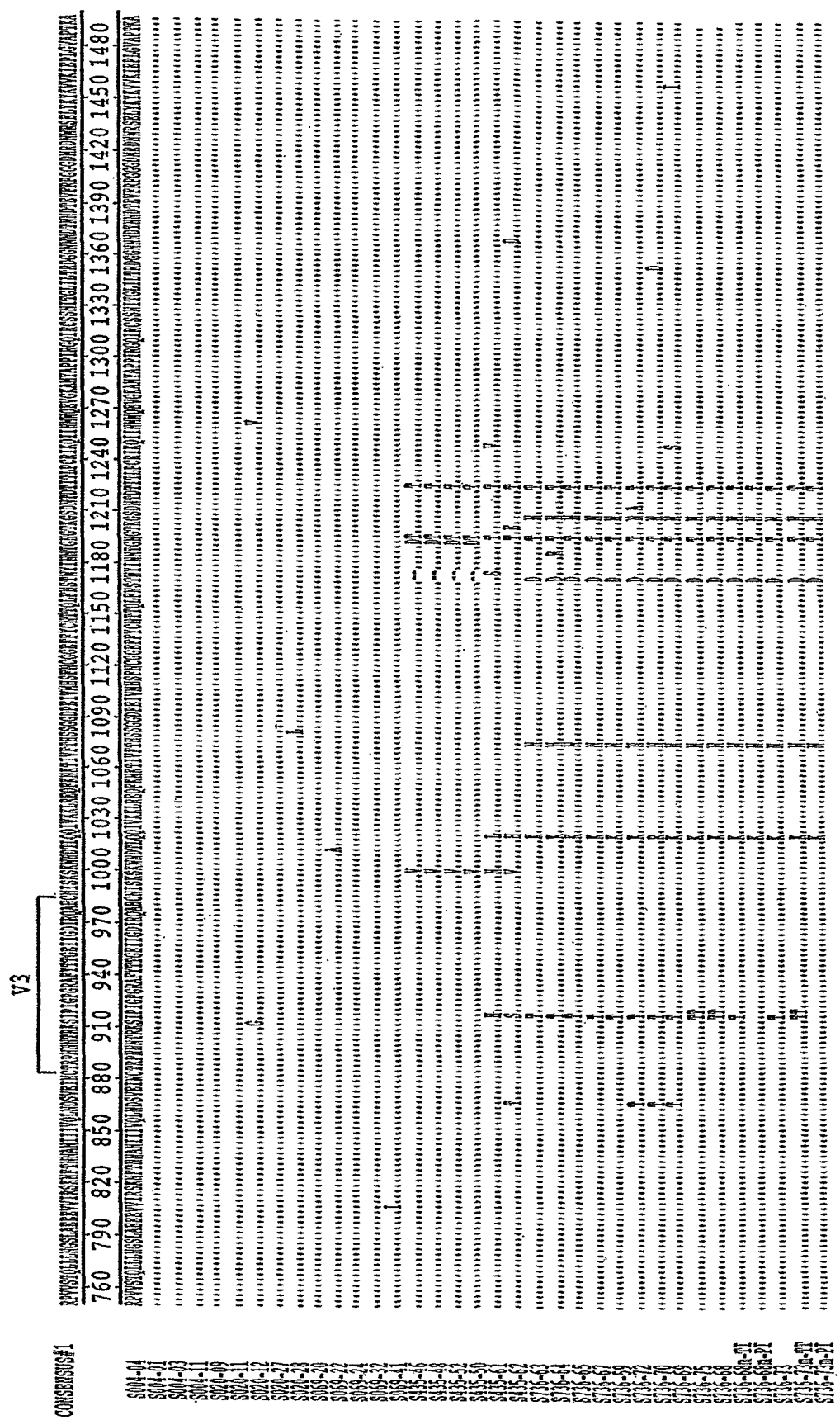
Figures 2, 3:
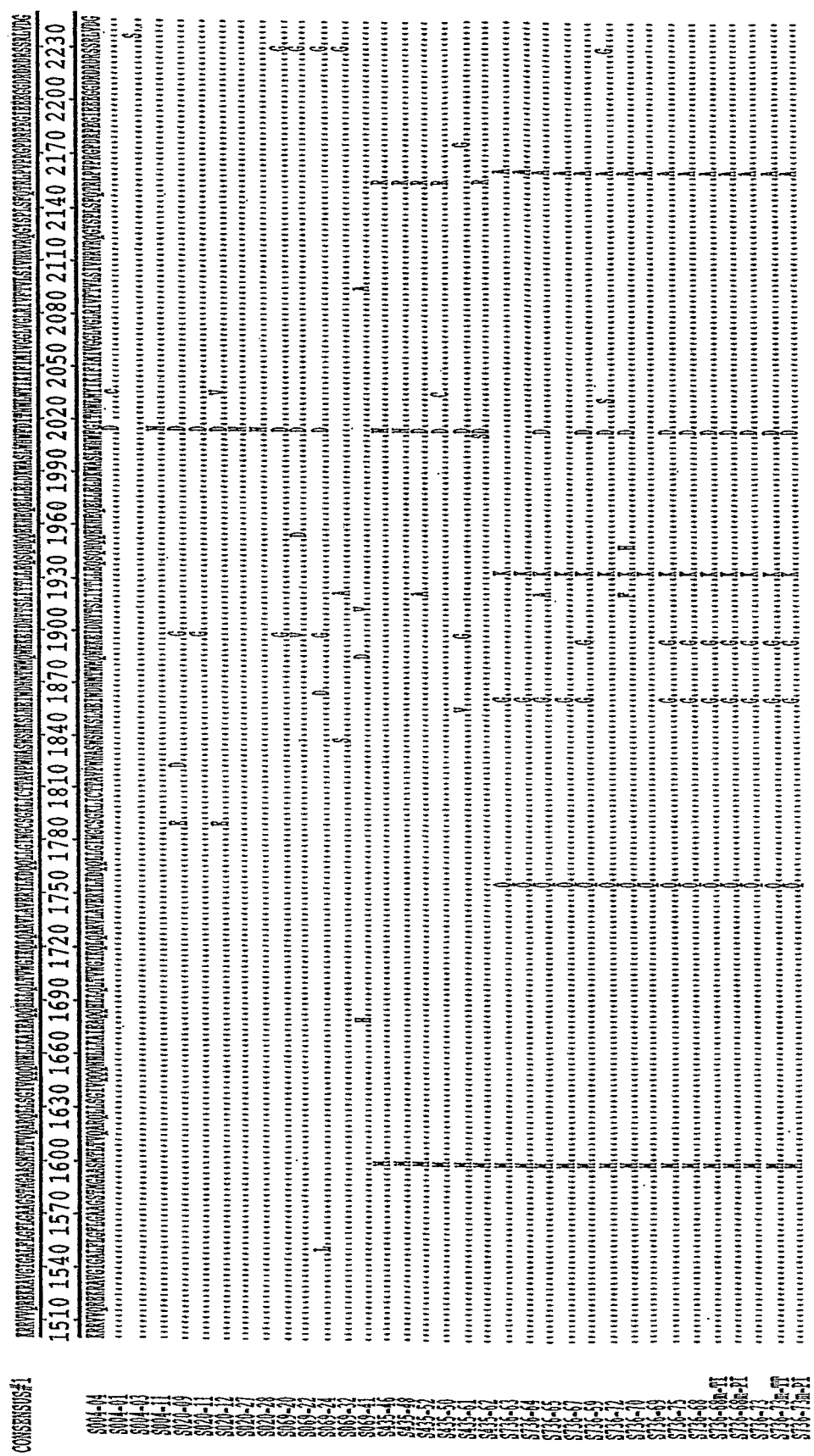

FIG. 3 provides an alignment of the amino acid sequences of various envelope polypeptides from HIV-2 viruses including, 7312A (SEQ ID NO:2), UC1 (SEQ ID NO:7), UC2 (SEQ ID NO:8) and ROD-D.14 (SEQ ID NO:9) and the amino acid sequence of envelope from HIV-1 virus HXB2 (SEQ ID NO:10).

Figures 2, 3, 4:
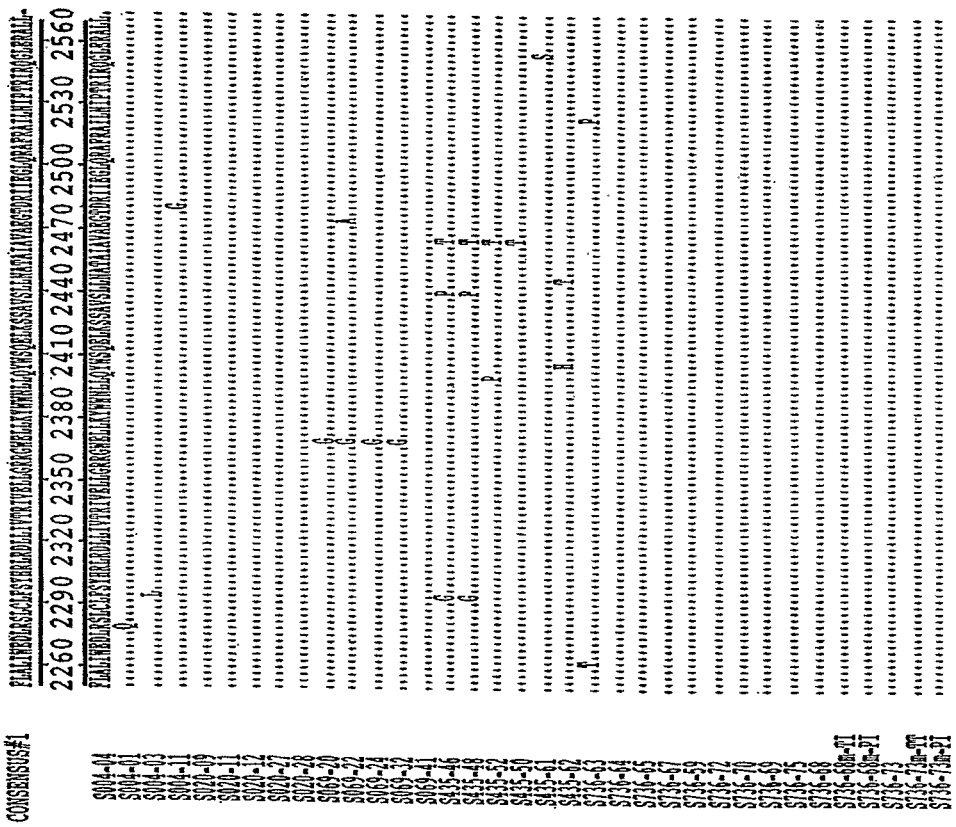

FIG. 4 provides the location of 2F5 (single underline) and 4E10 (double underline) Epitopes in HIV-1 (YU-2 and HXB-2) gp41 and corresponding sequences in HIV-2 (ST, 7312A, and UC1). This alignment shows the conservation of the 4E10 epitope at a sequence level and as a target of 4E10-mediated neutralization between HIV-1 and HIV-2. The envelope polypeptides comprises ST (SEQ ID NO:14), 7312A (SEQ ID NO:2); UC1 (SEQ ID NO:7), HXB-2 (SEQ ID NO:10), and YU-2 (SEQ ID NO:13).

Figure 5:
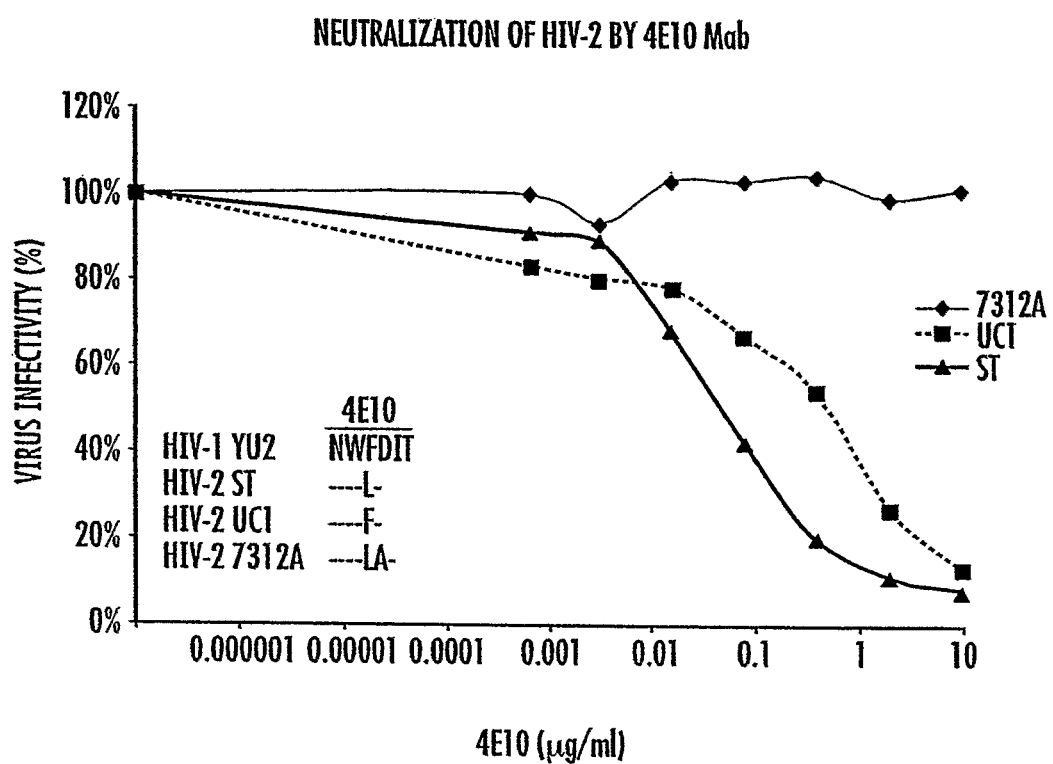

FIG. 5 shows the neutralization of HIV-1 by 4E10 monoclonal antibodies. These data show that certain naturally-occurring or genetically-modified strains of HIV-2 can be used to detect HIV neutralization by 4E10 and 4E10-like antibodies.

Figure 6:
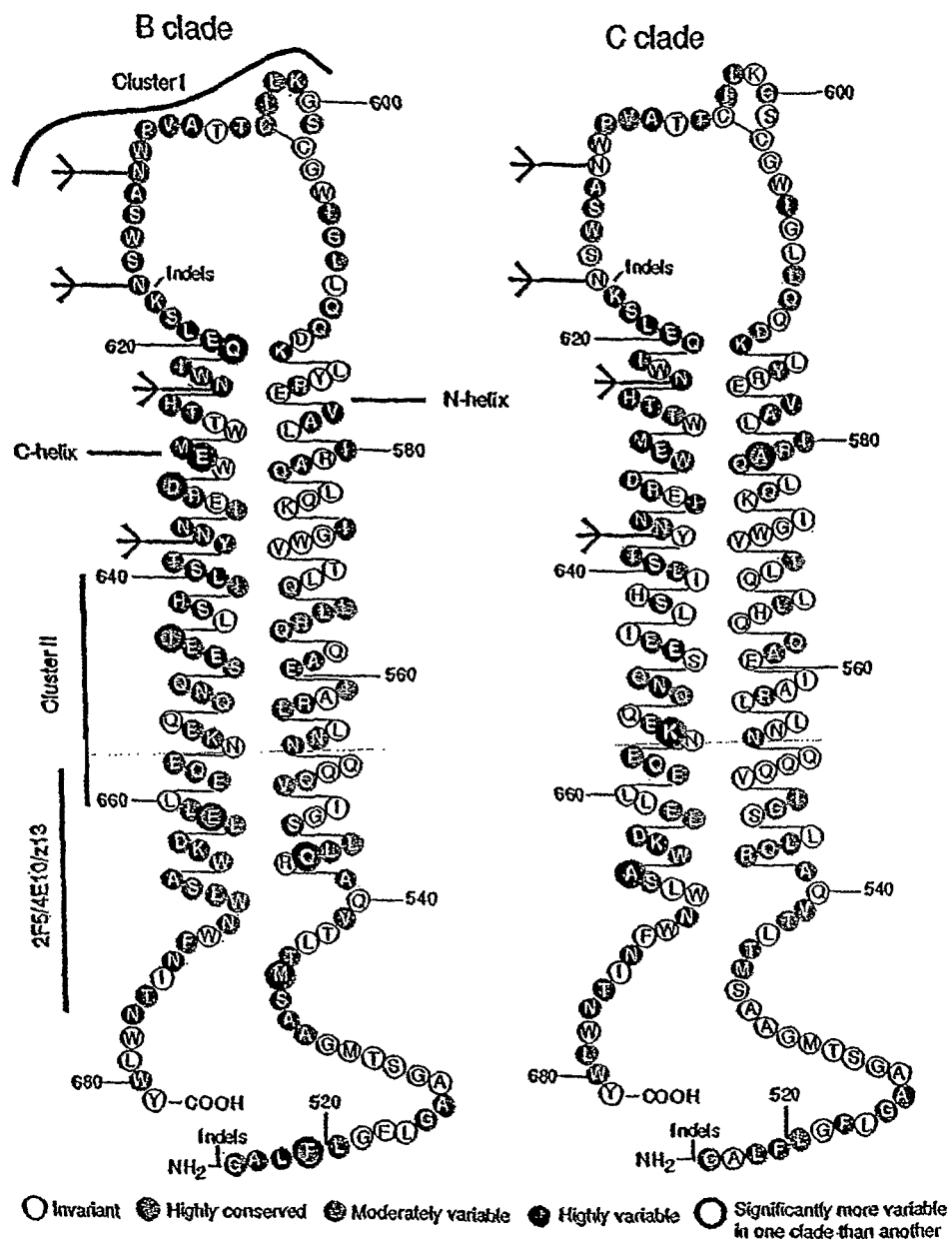

FIG. 6 provides a 2-D schematic of HXB2 gp41e from *HIV Molecular Immunology* (2002) Bette et al. eds., Los Alamos National Laboratory, Theoretical Biology and Biophysics, Los Alamos, N. Mex. LA-UR 03-5816. The figure illustrates the position of the 2F5/4E10/Z13 epitope cluster, epitope cluster II, the C-helix, N-helix, and epitope cluster I.

FIG. 7 provides the amino acids sequence of 6 chimeric envelope polypeptides from HIV-2 7312A. Amino acids 648 to 687 of the 7312A envelope polypeptide (SEQ ID NO:2) is shown with a region of the MPER double underlined. The constructs designated as 7312A-C1, 7312A-C2, 7312A-C3, 7312A-C4 (SEQ ID NO:27, 29, 31, and 33, respectively) are chimeric 7312A envelope polypeptides in which a region of the MPER domain from an HIV-1 envelope polypeptide has been substituted for the native HIV-2 sequence. The heterologous domain derived from HIV-1 is in bold and highlighted. Similarly, constructs 7312A-C5 and 7312A-C6 (SEQ ID NO:35 and 37, respectively) represent chimeric 7312A envelope polypeptides in which specific amino acid substitutions were made to introduce HIV-1 epitopes into the HIV-2 envelope polypeptide.

FIG. 8 provides an alignment of the gp41 region of HIV-1 (YU-2) and corresponding sequences in HIV-2 (ST, 7312A, and UC1) highlighting the 2F5 (single underline) and 4E10 (double underline) epitopes within the MPER. The envelope polypeptides comprises ST (SEQ ID NO:14), 7312A (SEQ ID NO:2); UC1 (SEQ ID NO:7), and YU-2 (SEQ ID NO:13).

DETAILED DESCRIPTION OF THE INVENTION

The present inventions now will be described more fully hereinafter with reference to the accompanying examples, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The article "a" and "an" are used herein to refer to one or more than one (i.e., to at least one) of the grammatical object of the article. By way of example, "an element" means one or more than one element.

Overview

The membrane proximal external region (MPER) epitopes 4E10 and 2F5, and surrounding peptide sequences, are broadly cross-reactive neutralizing epitopes on HIV-1. However, to date, all studies attempting to use this region of the HIV-1 envelope glycoprotein as an immunogen to elicit neutralizing antibodies have failed (reviewed in Burton et al. (2004) *Nature Immunol* 5:233-6; Zolla-Pazner et al. (2004) *Nature Rev Immunol* 4:199-210; Offek et al. (2004) *J Virol* 78:10724-37; Binley et al. (2004) *J Virol* 78:13232-52; and, Zwick et al. (2005) *J Virol* 79:1252-61). The present invention demonstrates that envelope polypeptides from lentiviruses that are not HIV-1 can be successfully employed as molecular scaffolds to present various heterologous epitopes that are recognized by HIV-1 neutralizing antibodies. We demonstrate that the heterologous epitopes in these chimeric polypeptides are more fully exposed to neutralizing antibodies when they are presented within the backbone of the chimeric polypeptide than when the epitope is presented within the context of an HIV-1 backbone. The present invention discloses various compositions and methods which employ these chimeric polypeptides as immunogens which can elicit protective antibodies against HIV.

Compositions

The present invention provides various immunogenic compositions. As used herein an "immunogenic composition" refers to any composition that is capable of eliciting an immune response. The term "vaccine" refers to an immunogenic composition that reduces the risk of, or prevents, infection by an infectious agent (a "prophylactic vaccine") or that ameliorates, to any extent, an existing infection (a "therapeutic vaccine"). If a vaccine protects an organism from subsequent challenge with the infectious agent, the vaccines is said to be "protective."

1. Chimeric Envelope Polypeptides and Polynucleotides

The present invention provides an immunogen comprising a chimeric envelope polypeptide which is not from HIV-1 which comprises at least one heterologous epitope that is recognized by an HIV-1 neutralizing antibody. Additional immunogens of the invention include chimeric polynucleotides comprising a nucleotide sequence encoding an envelope polypeptide or a variant thereof, wherein the envelope sequence is not from HIV-1 and wherein the nucleotide sequence further encodes a heterologous epitope recognized by an HIV-1 neutralizing antibody.

As used herein, a "heterologous domain" or "heterologous epitope" comprises a domain that is not present in the native polynucleotide or polypeptide or the domain/epitope is found in an alternative location in the native polynucleotide or polypeptide. For example, a heterologous epitope for an HIV-1 neutralizing antibody comprises an epitope that is not present in the native non-HIV-1 envelope polypeptide (or the polynucleotide encoding the same). Alternatively, the heterologous epitope could comprise an epitope that is found in an alternative location in the native non-HIV-1 envelope polypeptide (or the polynucleotide encoding the same). Polypeptides or polynucleotides comprising such heterologous epitopes are referred to herein as "chimeric polypeptides" or "chimeric polynucleotides", respectively. Heterologous epitopes which can be employed in the chimeric polypeptides of the invention are discussed elsewhere herein, as are various methods to determine if such an epitope is present in the envelope polypeptide.

In specific embodiments, the chimeric polynucleotides or polypeptides of the invention are isolated or substantially purified polynucleotide or polypeptide compositions. An "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the polypeptide of the invention or biologically active portion thereof is recombinantly produced, optimally culture medium represents less than about 30%, 20%, 10%, 5%, or 1% (by dry weight) of chemical precursors or non-protein-of-interest chemicals.

The chimeric envelope polypeptide employed in the methods may be either in the glycosylated or deglycosylated form. In addition, the envelope polypeptide of the invention or polynucleotide encoding the same can be an envelope polypeptide from any lentivirus or any primate lentivirus. In specific methods, the envelope polypeptide is from any primate lentivirus that is not HIV-1. Such primate lentivirus include, for example, HIV-2 (Isolate BEN), HIV-2 (Isolate CAM2), HIV-2 (Isolate D194), HIV-2 (Isolate D205,7), HIV-2 (Isolate GHANA-1), HIV-2 (Isolate ROD); Simian AIDS retrovirus (SRV-1) such as, SIV (AGM155), SIV (AGM266 isolate), SIV (AGM3 isolate), SIV (AGM385 isolate), SIV (F236/SMH4 isolate, Sooty Mangabey), SIV (TyO-1 isolate) and SIVagm; Simian immunodeficiency virus, such as, SIV (1A11 isolate), SIV (isolate African mandril), SIV (AGM/clone Gri-1), SIV (vervet), SIV (Tantalus), SIV (STM isolate), SIV (17E-C1), SIV Qu, SIVdeb, SIVmac, SIVMND, SIVmon, SIVsm; Simian immunodeficiency virus 2; and Simian-Human immunodeficiency virus.

In specific embodiments, the envelope polypeptide used to construct the chimeric polypeptide is from HIV-2. For example, in one method, an HIV-2 envelope polypeptide or functional variants thereof is used. By "HIV-2 envelope polypeptide" or "envelope encoded by an HIV-2 polynucleotide" is intended the form of the HIV-2 envelope polypeptide, or polynucleotide encoding the same, in the HIV-2 viral isolate 7312A. The amino acid of the envelope polypeptide of the HIV-2 isolate 7312A is set forth in SEQ ID NO:2. The nucleotide sequence encoding the envelope polypeptide of the HIV-2 isolate 7312A is set forth in SEQ ID NO:21.

Variants of the HIV-2 envelope polypeptide are biologically active, that is they continue to possess the desired biological activity of the native protein, that is, they continue to interact with CD4 and/or facilitate virus fusion and/or facilitate viral entry into a permissive cell. It is further recognized that the viral envelope polypeptide is produced as a precursor (gp 160) that is subsequently cleaved into two parts, gp120 which binds CD4 and chemokine receptors, and gp41, which is anchored in the viral membrane and mediates viral fusion. Variants of the HIV-2 envelope polypeptide encompass fragments of HIV-2 envelope including, for example, gp41, gp120 or any other fragment that retains the necessary activity. The amino acid sequence comprising gp41 and gp120 is denoted in FIGS. 1, 2, 3 and 4. Various domains of the HIV-2 envelope polypeptide include gp41 (about amino acids 513-857 of SEQ ID NO:2) and gp120 (about amino acids 20-514 of SEQ ID NO:2). Additional domains of HIV envelope polypeptides are discussed in further detail in Burton et al. (2004) *Nature Immunology* 5:233 and Zwick et al. (2004) *Nature Medicine* 10:133, both of which are herein incorporated by reference.

Variants of HIV-2 envelope polypeptide are known. See, for example, FIGS. 1 and 3 which provide the amino acid sequence of envelope polypeptides from various HIV-2 strains, including UC1, UC2, and ROD-B. Assays to measure HIV-2 envelope activity include, for example, envelope binding assays to CD4 and cell fusion assays. Such methods are described in detail in Martin et al. (2003) *Nature Biotechnology* 21:71-76, herein incorporated by reference in its entirety.

In other embodiments, the envelope polypeptide used to construct the chimeric polypeptide is an SIV envelope polypeptide or a functional variant thereof. By "SIVsm envelope polypeptide" or "envelope encoded by an SIVsm envelope polynucleotide" is intended the form of the SIVsm envelope polypeptide or polynucleotide encoding the same in SIVsm PBJ1.9. The amino acid of the envelope polypeptide of the SIVsm PBJ1.9 is set forth in SEQ ID NO:3 and the nucleotide sequence encoding this polypeptide is set forth in SEQ ID NO:22. In other methods, a SIVsm envelope polypeptide, polynucleotide, or a functional variant thereof is used to generate the chimeric polypeptide or polynucleotide. See, also, Israel et al. (1993) *AIDS Res. Hum. Retroviruses* 9:277-286; Hirsch et al. (1998) *Nat. Med.* 4(12):1401-8; Mahalingam et al. (2001) *J. Virol.* 75(1):362-74, each of which is herein incorporated by reference.

By "SIVagm envelope polypeptide" or "envelope encoded by an SIVagm polynucleotide" is intended the form of the SIVagm envelope polypeptide or polynucleotide encoding the same in SIVagmVer155. The amino acid sequence of the envelope polypeptide of SIVagmVer155 is set forth in SEQ ID NO:4. See, also, Johnson et al. (1990) *J. Virol.* 64 (3), 1086-1092, herein incorporated by reference. Other envelope polypeptides from SIVagm are known. For example, the amino acid sequence for the envelope polypeptide from SIVagmTAN is provided in SEQ ID NO:5. See, also, Soares et al. (1997) *Virology* 228 (2): 394-399.

Variants of the SIV envelope polypeptide are biologically active, that is they continue to possess the desired biological activity of the native protein (i.e., they continue to interact with CD4 and/or facilitate virus fusion and/or facilitate viral entry into a permissive cell). Variants of the SIV envelope polypeptides encompass fragments of SIV envelope including, for example, gp41, gp120 or any other fragment that retains the necessary activity. The amino acid sequences of gp41 and gp120 are denoted in FIGS. 1, 2, 3 and 4.

2. Variant Polynucleotides and Polypeptides

As discussed throughout, the compositions disclosed herein can employ variant envelope polypeptides, variant polynucleotides encoding the envelope polypeptides, as well as variants of the heterologous epitopes recognized by the HIV-1 neutralizing antibodies. As used herein, "variants" is intended to mean substantially similar sequences. A "variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. As used herein, a "native" polynucleotide or polypeptide comprises a naturally occurring nucleotide sequence or amino acid sequence, respectively. As defined herein, the "native" envelope polypeptide of HIV-2 or polynucleotide encoding the same is from the HIV-2 isolate 7312A (SEQ ID NO:2 and 21), the "native" envelope polypeptide of SIVsm or the polynucleotide encoding the same is from SIVsmPBj1.9 (SEQ ID NO:3 and 22), the "native" envelope polypeptide of SIVagm or the polynucleotide encoding the same is from SIVagmVer155 (SEQ ID NO:4 and 23) or SIVagmTAN (SEQ ID NO:5 and 24), and the "native" sCD4 polypeptide is set forth in SEQ ID NO: 1. Variant proteins encompassed by the present invention are biologically active, that is they continue to possess the desired biological activity of the native protein activity as described herein for envelope. Such variants may result from, for example, genetic polymorphism or from human manipulation. Biologically active variants of a native envelope polypeptide and/or a native soluble CD4 polypeptide employed in the methods of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

A fragment of a biologically active portion of an envelope polypeptide of the invention will encode at least 15, 25, 30, 50, 100, 150, 200, 250, 300, 350, 400, 450, 500, 550, 600, 650, 700, 750, 800, 850, 900, 1000, or 1,200 contiguous amino acids, or up to the total number of amino acids present in a full-length envelope polypeptide of the invention.

For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the envelope polypeptides of the invention. Naturally occurring allelic variants such as these can be identified with the use of well-known molecular biology techniques, such as, for example, with polymerase chain reaction (PCR) and hybridization techniques as outlined below. Variant polynucleotides also include synthetically derived polynucleotides, such as those generated, for example, by using site-directed mutagenesis but which still encode an envelope protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO:21, 22, 23, or 24 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides has at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

A fragment of an envelope polynucleotide may encode a biologically active portion of an envelope polypeptide. A biologically active portion of an envelope polypeptide can be prepared by isolating a portion of one of the envelope polynucleotides of the invention, expressing the encoded portion of the envelope protein (e.g., by recombinant expression in vitro), and assessing the activity of the portion of the envelope polypeptide. Polynucleotides that are fragments of an envelope nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400 or more contiguous nucleotides, or up to the number of nucleotides present in a full-length envelope polynucleotide disclosed herein.

Variant envelope polypeptides of the invention, as well as polynucleotides encoding these variants, are known in the art and are discussed in further detail elsewhere herein. The polypeptide employed in the methods of the invention may be altered in various ways including amino acid substitutions, deletions, truncations, and insertions. Methods for such manipulations are generally known in the art. As discussed below, variant polypeptides or polynucleotides of the invention can comprise heterologous epitopes for HIV-1 binding antibodies. For example, amino acid sequence variants and fragments of the envelope polypeptide can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the polypeptides and polynucleotides employed in the methods of the invention encompass naturally occurring sequences as well as variations and modified forms thereof. Such variants will continue to possess the desired activity for envelope as discussed elsewhere herein. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated for functional variants of the envelope polypeptides by the ability to interact with CD4 and/or facilitate virus fusion and/or facilitate viral entry into a permissive cell. See, for example, Martin et al. (2003) *Nature Biotechnology* 21:71-76, herein incorporated by reference.

Methods of alignment of sequences for comparison are well known in the art. Thus, the determination of percent sequence identity between any two sequences can be accomplished using a mathematical algorithm. As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

3. Heterologous Epitopes

As used herein, an "HIV-1 binding antibody" comprises an antibody that specifically interacts with an epitope of HIV-1. An HIV-1 binding antibody that can neutralize a virus is referred to herein as an "HIV-1 neutralizing antibody." As discussed above, the chimeric envelope polypeptides, and polynucleotides encoding the same, are from a lentivirus that is not HIV-1 and further comprises at least one heterologous epitope that is recognized by an HIV-1 neutralizing antibody.

By "specifically interacts" is intended that the antibody that recognizes the epitope of an HIV-1 envelope polypeptide forms a specific antibody-antigen complex with that epitope (either in an in vitro or in vivo setting) when the epitope is contained in an envelope polypeptide that is not from HIV-1. Thus, the HIV-1 binding antibody binds preferentially to the non-HIV-1 envelope polypeptide comprising the heterologous HIV-1 epitope. By "binds preferentially" is meant that the antibody immunoreacts with (binds) substantially more of the non-HIV-1 envelope polypeptide comprising the HIV-1 epitope than the non-HIV-1 envelope polypeptide lacking the epitope, when both polypeptides are present in an immunoreaction admixture. Substantially more typically indicates at least greater than 10%, 20%, 30%, 40%, 50%, 60%, 70%, 80%, 90%, 95%, or greater of the immunoprecipitated material is the non-HIV-1 envelope polypeptide comprising the HIV-1 epitope.

The heterologous epitope can be native to the HIV-1 envelope polypeptide or alternatively, the epitope can be synthetically derived, so long as the epitope continues to be recognized by the HIV-1 neutralizing antibody. In addition, the heterologous epitope or the heterologous domain containing the epitope can be of any length including about 2 to about 7 amino acids, about 5 to about 10 amino acids, about 11 to about 20 amino acids, about 21 to about 30 amino acids, about 31 to about 40 amino acids, about 41 to about 50 amino acids, about 51 to about 60 amino acids, about 61 to about 70 amino acids, about 71 amino acids to about 80 amino acids, about 81 to about 90 amino acids, about 91 to about 100 amino acids, about 101 to about 110 amino acids, or longer.

The heterologous epitope can be placed anywhere in the envelope sequence, as long as the chimeric polypeptide retains the activity of the native envelope polypeptide. In still further embodiments, the amino acid sequence of a non-HIV-1 envelope polypeptide is aligned with the amino acid sequence of an HIV-1 envelope polypeptide. The chimeric polypeptide is then engineered to comprise the necessary amino acid substitutions, deletions and/or additions that result in the heterologous epitope from the HIV-1 polypeptide to be placed in the corresponding region of the non-HIV-1 envelope polypeptide. Determining such corresponding regions between two polypeptides or polynucleotides is routine in the art. See, for example, FIGS. 1, 3, and 4, which provide representative alignments that allow one to determine "corresponding" amino acids for a subset of lentiviruses.

The nucleotide sequence encoding the heterologous epitope or the domain it is contained in can be of any length including about 15 to about 30 nucleotides, about 31 to about 60 nucleotides, about 61 to about 90 nucleotides, about 91 to about 120 nucleotides, about 121 to about 150 nucleotides, about 151 to about 180 nucleotides, about 181 to about 210 nucleotides, about 210 to about 240 nucleotides, about 241 to about 270, about 271 to about 300, about 301 to about 330 nucleotides, or longer. It is recognized that various methods can be employed to generate the chimeric polynucleotide having the heterologous epitope including nucleic acid substitutions, deletions, truncations, and insertions. Methods for such manipulations are generally known in the art.

Assays to measure envelope activity include, for example, envelope binding assays to CD4, cell fusion assays, and virus entry assays. Such assays are discussed in further detail elsewhere herein. It is recognized that various methods can be employed to generate the chimeric polypeptide having the heterologous epitope including amino acid substitutions, deletions, truncations, and insertions. Methods for such manipulations are generally known in the art.

Methods for determining if the heterologous epitope is recognized by an HIV-1 neutralizing antibody are disclosed in U.S. Provisional Application No. 60/606,053, filed Aug. 31, 2004 and 60/562,824, filed Apr. 16, 2004 and U.S. Provisional Application No. 60/649,551, filed Feb. 3, 2005, entitled "Molecular Scaffolds for HIV-1 Epitopes," each of these references is herein incorporated by reference. In addition, the formation of an antibody-antigen complex can be assayed using a number of well-defined diagnostic assays including conventional immunoassay formats to detect and/or quantitate antigen-specific antibodies. Such assays include, for example, enzyme immunoassays, e.g., ELISA, cell-based assays, flow cytometry, radioimmunoassays, and immunohistochemical staining. Numerous competitive and non-competitive protein binding assays are known in the art and many are commercially available. Representative assays include, for example, various binding assays with chemokine receptors (CCR5 or CXCR4), gp41, characterized domains of these polypeptides, and competitive binding assays with characterized HIV-1 binding antibodies.

In addition, if the chimeric envelope polypeptide is associated with a retrovirus, "neutralization" of the virus in the presence of an appropriate neutralizing antibody can be assayed. For example, a reduction in the establishment of HIV infection and/or reducing subsequent HIV disease progression in this sample when compared to a control sample that lacks the HIV-1 neutralizing antibody can also be monitored. A reduction in the establishment of HIV infection and/or a reduction in subsequent HIV disease progression encompass any statistically significant reduction in HIV activity in the sample. Methods to assay for the neutralization activity include, but are not limited to, a single-cycle infection assay as described in Martin et al. (2003) *Nature Biotechnology* 21:71-76. In this assay, the level of viral activity is measured via a selectable marker whose activity is reflective of the amount of viable virus in the sample, and the IC50 is determined. In other assays, acute infection can be monitored in the PM1 cell line or in primary cells (normal PBMC). In this assay, the level of viral activity can be monitored by determining the p24 concentrations using ELISA. See, for example, Martin et al. (2003) *Nature Biotechnology* 21:71-76, herein incorporated by reference. Further methods include those employing the adherent HeLa cell-derived JC53BL-13 cell line (NIH AIDS Research and Reference Reagent Program Catalogue No. 8129, TZM-b1) as described in Wei et al. (2003) *Nature* 422:307-312, herein incorporated by reference.

A variety of epitopes for HIV-1 neutralizing antibodies are known in the art. Such epitopes are found, for example, in gp160, gp120, or gp41. In specific embodiments, the epitope recognized by the HIV-1 neutralizing antibody is from an HIV-1 envelope polypeptide. Any HIV strain or isolate can be used. See, for example, *HIV Molecular Immunology* (2002) Korber et al. ed., Los Alamos National Laboratory, Theoretical Biology and Biophysics, Los Alamos, N. Mex. LA-UR 03-5816, which is herein incorporated by reference in its entirety.

In specific embodiments, the epitope recognized by the HIV-1 neutralizing antibody is in gp41. For example, epitopes found in the N-terminal hydrophobic fusion peptide of gp41 (about amino acids 512 to about 527 of SEQ ID NO: 10), the disulfide-loop region of gp41 that links the N-HR and C-HR regions (about amino acids 581 to about 628 of SEQ ID NO: 10), the N-HR region of gp41 (about amino acids 546 to about 581 of SEQ ID:10), the C-HR of gp41 (about amino acids 628 to about 661 of SEQ ID NO: 10), the membrane proximal region of gp41 (about amino acids 657 to about amino acids 684 of SEQ ID NO: 10) can be used.

As used herein, an "MPER region" comprises the MPER region found in HIV-1 YU-2 (i.e., N-LALDKWASLWN-WFDITKWLWYIK-C (SEQ ID NO:38)). A functional variant of an MPER region will continue to be recognized by an HIV-1 binding antibody. Methods to assay for the binding of the HIV-1 binding antibody are discussed elsewhere herein as are methods to determine if the variant sequence is immunologically equivalent. Such variants can include internal and/or terminal additions, deletions, and/or substitutions. The variants can differ by 1, 2, 3, 4, 5, 6, 7, 8, 9, 10, 11, 12, 13, 14, 15, or more amino acids. Variants of the MPER region are known. See, for example, FIG. 8 which provides the MPER region of HXB2C, ST, and UC1. Additional variants of the MPER region are shown in FIG. 7.

Epitopes of interest within the membrane proximal region of gp41 can be found, for example, between about amino acids 657 to 675, about amino acid 670 to 684, about amino acids 665 to about 680, or about amino acids 667 to about 681 of SEQ ID NO:10. See, Follis et al. (2002) *J. of Virology* 76:7356-7362 for additional domains of gp41 that are of interest. In other embodiments, an epitope of the HIV-1 neutralizing antibody is found in the bridging sheet, variable loop 1, variable loop 2, variable loop 3, variable loop 4, the chemokine receptor binding site, or the CD4 binding site. See, for example, FIG. 1 which outlines the various domains of gp120 in the HXB2 HIV-1 isolate. It is recognized that an entire domain of the HIV-1 envelope protein may be inserted into the heterologous envelope polypeptide or alternatively, any fragment of the domain from the HIV-1 envelope polypeptide can be used as the epitope for the HIV-1 binding antibody.

Additional epitopes of interest include, but are not limited to, the 4E 10 epitope (SEQ ID NO:15), the Z13 epitope (SEQ ID NO:15) and the 2F5 epitope (SEQ ID NO: 16). See, for example, U.S. Publication No. 20030157063, Muster et al. (1993) *J. Virol.* 67:6642-6647, Zwick et al. (2001) *J. Virology* 75:10892-10905, Ferrantelli et al (2002) *Curr. Opin. Immunol.* 14:495-502, and Wang et al. (2003) *Curr. Pharm. Des.* 9:1771-87. Each of these epitopes is denoted in FIG. 4. Alternatively, the entire neutralization 2F5/4E10/Z13 cluster could be employed. Accordingly, each of the epitopes or domains from HIV-1 can be engineered into the corresponding position of a non-HIV-1 envelope polypeptide. For example, amino acids 657 to 684 of SEQ ID NO: 10 can replace the corresponding amino acids (i.e., amino acids 655-682) of SEQ ID NO:2. Alternatively, amino acids 657 to 684 of SEQ ID NO:10 can replace the corresponding amino acids (i.e., amino acids 665 to 673 or amino acids 648-675) of SEQ ID NO: 14.

Additional epitopes for HIV-1 binding antibodies include the epitope located at amino acid number 662 to 667 of gp41 of the HIV-1 isolate BH10 (GenBank Acc No. M1565) with the number as described in the Swissprot database entry ENV$HIV10; the epitope located at amino acid position 79 to 184 or amino acid position 326 to 400 of the processed gp120 of HIV-1 isolate BH10 (GenBank Acc. No. M15165, with numbering as described in Swissprot database entry ENV$SHIV10). See, for example, U.S. Pat. No. 6,268,484. See, also, Rizzuto et al. (2000) *AIDS Res Hum Retroviruses* 16:741-749 and Xiang et al. (2002) *AIDS Res Hum Retroviruses* 18:1207-1217 which characterize the HIV-1 gp120 structures implicated in the CCR5 and CD4-induced antibodies. Epitopes for 17b, 48d, b12, and 2G12 are also known. See, for example, Rizzuto et al. (1998) *Science* 280:1949-1953, Thali et al. (1993) *J. Virol.* 67:3978-3988, and Trkola et al. (1996) *J. Virol.* 70:1100-1108. A review of additional characterized epitopes for HIV-1 binding antibodies and their location in the HIV-1 envelope polypeptide can be found in *HIV Molecular Immunology* (2002) Bette et al. eds., Los Alamos National Laboratory, Theoretical Biology and Biophysics, Los Alamos, N. Mex. LA-UR 03-5816. The contents of each of these references are herein incorporated by reference in their entirety.

It is further recognized that immunologically equivalent epitopes for the HIV-1 neutralizing antibodies discussed above are known and can be used in the methods and compositions of the invention. Immunologically equivalent epitopes for 2F5 are known. See, for example, U.S. Application Publication No. 20030157063, Kattinger et al. (1992) Septime Colloque des Cent Gardes, 299-303, EP-0570357, and Zwick et al. (2001) *J. Virology* 75:10892-10900 which disclose immunologically equivalent epitopes of the 2F5 epitope. Such immunologically equivalent epitopes, while differing in their amino acid sequence, continue to be recognized by the 2F5 monoclonal antibody (Virus Testing Systems, Houston, Tex., USA). Immunologically equivalent epitopes for 4E10 and Z13 are also known. See, for example, Zwick et al. (2001) *J. Virology* 75:10892-10900. Again, such immunologically equivalent epitopes, while differing in their amino acid sequence continue to be recognized by the 4E10 monoclonal antibody or the Z13 antibody. Accordingly, immunologically equivalent epitopes can differ from the epitope set forth in SEQ ID NO: 15 and 16 by at least 1, 2, 3, 4, 5, 6, 7, 8 or more amino acids. The differences can be generated by amino acid substitutions, deletions and insertions. Methods to determine if two epitopes are immunologically equivalent are known in the art. See, for example, U.S. Application Publication No. 20030157063, EP-0570357 and Zwick et al. (2001) *J. Virology* 75:10892-10900, all of which are herein incorporated by reference.

Exemplary chimeric polynucleotides and polypeptides of the invention include sequences encoding non-HIV-1 envelope polypeptides, or variants thereof, which have been modified to have a heterologous HIV-1 MPER region, a 4E10, a Z13, or a 2F5 epitope or a functional variant (immunologically equivalent epitope) thereof as discussed elsewhere herein. Non-limiting examples of such chimeric polynucleotides and polypeptides include the envelope polypeptide of HIV-2 7312A in which amino acids 675 and 676 (HXB-2c, SEQ ID NO:10) are altered from L to I and from A to T, respectively. As shown in FIG. 4, these positions correspond to amino acids 673 and 674 of the envelope polypeptide of HIV-2 7312A. This chimeric polypeptide comprises a heterologous epitope that renders the virus sensitive to neutralization by 4E10 antibodies. In other embodiments, the chimeric envelope polypeptide, or nucleotide sequence encoding it, comprises the HIV-2 ST envelope polypeptide in which amino acids 675 and 676 (HXB-2c, SEQ ID NO: 10) are altered from L to A and from T to A, respectively. This alteration eliminates 4E10 binding. As shown in FIG. 4, these positions correspond to amino acid 664 and 665 of the HIV-2 ST envelope polypeptide (SEQ ID NO:14).

Additional non-limiting examples include the chimeric envelope polypeptide of HIV-2 7312A or HIV-2 ST in which the heterologous 2F5 epitope, or the immunologically equivalent epitope thereof, is engineered into the polynucleotide. One such chimeric polypeptide, and the chimeric polynucleotide encoding it includes the polypeptide having site-directed mutations in the HIV-2 7312A envelope polypeptide at positions 660 (K to A), 662 (N to D), 663 (S to K), and 665 (D to A) of SEQ ID NO:2, which together make the HIV-2 sequence identical to that of the 2F5 epitope region of HIV-1 YU2. As shown in FIG. 4, these positions correspond to amino acids 662, 664, 665, and 667, respectively, of HXB-2c (SEQ ID NO:10). Additional chimeric HIV-1 envelope polypeptides having a heterologous MPER region, or a functional variant or fragment thereof, are set forth in FIG. 7.

4. Immunogenic Compositions

Immunogenic compositions of the invention can include an isolated chimeric polypeptide or active variant thereof or an isolated polynucleotide encoding the chimeric envelope polypeptide of the invention or active variant thereof. An isolated chimeric envelope polypeptide of the invention is present in an immunogenic composition in an amount sufficient to elicit an immune response against the heterologous epitope upon administration of a suitable dose to a subject. An isolated chimeric polynucleotide encoding a chimeric envelope polypeptide of the invention can also be present in the immunogenic composition in an amount sufficient such that administration of a suitable dose to a subject results in the expression of the encoded chimeric envelope polypeptide, which stimulates an immune response against the heterologous HIV-1 epitope. As used herein, a "subject" is defined as any animal including any mammal, such as, rodents, rabbits, goats, sheep, humans, primates, etc.

It is recognized that the immunogenic compositions can comprise at least two different chimeric envelope polypeptides and/or polynucleotides encoding the chimeric polynucleotides. Variations of this embodiment can provide as many different immunogenic sequences as desired, for example, 3, 4, 5, 6, 7, 8, 9, 10 or more different sequences encoding the chimeric polypeptides.

a. Immunogenic Compositions Comprising the Chimeric Envelope Polynucleotide

The invention provides immunogenic compositions comprising a chimeric envelope polypeptide of the invention or an active variant or fragment thereof. In one embodiment, an immunogenic composition of the invention includes cells expressing a chimeric envelope polypeptide of the invention, a cell lysate, or a fraction thereof, containing the chimeric polypeptide, such as, e.g., a membrane fraction. In other embodiments, the immunogenic composition comprises an isolated chimeric envelope polypeptide or variant thereof.

In other embodiments, the immunogenic chimeric envelope polypeptide or active variant thereof can be provided as a virus-derived vaccine. As used herein, the term "virus-derived vaccine" refers to a vaccine containing a viral particle, a virus-like particle (VLP), some portion of a viral particle or VLP, and/or a virally infected cell that displays the antigen on its surface, wherein administration of the particle or cell to an organism elicits an immune response to the displayed antigen.

Immunization of subjects with engineered viral-like particles and/or infected cells is well known in the art. Virus-derived vaccines can be advantageous because the viral infection component can promote a vigorous immune response that activates B lymphocytes, helper T lymphocytes, and cytotoxic T lymphocytes. Numerous viral species can be used to produce recombinant viruses useful in virus-derived vaccines. Examples include vaccinia virus (International Patent Publication WO 87/06262; Cooney et al. (1993) *Proc. Natl. Acad. Sci. USA* 90:1882-6; Graham et al. (1992) *J. Infect. Dis.* 166:244-52; McElrath et al. (1994) *J Infect. Dis.* 169:41-7) and canarypox virus (Pialoux et al. (1995) *AIDS Res. Hum. Retroviruses* 11:373-81; Andersson et al. (1996) *J. Infect. Dis.* 174:977-85; Fries et al. (1995) *Vaccine* 14:428-34; Gonczol et al. (1995) *Vaccine* 13:1080-5).

Virus-derived vaccines can be treated in a manner to inactivate or attenuate the virus. An attenuated recombinant virus refers to a virus that has been altered in a manner that renders the virus less virulent than the native virus. Methods for inactivating or attenuating virus are known in the art, and include, for example, treatment with paraformaldehyde, formalin, phenol, UV light, elevated temperature and the like. U.S. Pat. No. 6,503,753 describes methods for photoinactivation of HIV reverse transcriptase which thereby inactivates the HIV virus. Primate immunodeficiency viruses can also be prepared that are replication-defective. U.S. Pat. No. 6,500,623 describes HIV replication-defective viral particles and means for producing them. Other techniques for producing inactivated, attenuated and replication defective viruses are known in the art.

Virus-derived vaccines have also been prepared using defective adenovirus or adenovirus (Gilardi-Hebenstreit et al. (1990) *J. Gen. Virol.* 71:2425-31; Prevec et al. (1990) *J. Infect. Dis.* 161:27-30; Lubeck et al. (1989) *Proc. Natl. Acad. Sci. USA* 86:6763-7; Xiang et al. (1996) *Virology* 219:220-7). Other viruses that can be engineered to produce recombinant viruses useful in vaccines include retroviruses that are packaged in cells with amphotropic host range (see Miller (1990) *Human Gene Ther.* 1:5-14), and attenuated or defective DNA virus, such as, but not limited to, herpes simplex virus (HSV) (see, e.g., Kaplitt et al. (1991) *Molec. Cell. Neurosci.* 2:320-330), papillomavirus, Epstein Barr virus (EBV), adeno-associated virus (AAV) (see, e.g., Samulski et al. (1987) *J. Virol.* 61:3096-3101; Samulski et al. (1989) *J. Virol.* 63:3822-3828), poxvirus (U.S. Pat. Nos. 4,769,330, 4,722,848, 4,603,112, 5,110,587, 5,174,993, and 5,863,542), and the like.

A pharmaceutically acceptable carrier suitable for use in the invention is non-toxic to cells, tissues, or subjects at the dosages employed, and can include a buffer (such as a phosphate buffer, citrate buffer, and buffers made from other organic acids), an antioxidant (e.g., ascorbic acid), a low-molecular weight (less than about 10 residues) peptide, a polypeptide (such as serum albumin, gelatin, and an immunoglobulin), a hydrophilic polymer (such as polyvinylpyrrolidone), an amino acid (such as glycine, glutamine, asparagine, arginine, and/or lysine), a monosaccharide, a disaccharide, and/or other carbohydrates (including glucose, mannose, and dextrins), a chelating agent (e.g., ethylenediaminetetratacetic acid [EDTA]), a sugar alcohol (such as mamuitol and sorbitol), a salt-forming counterion (e.g., sodium), and/or an anionic surfactant (such as Tween™, Pluronics™, and PEG).

In one embodiment, the pharmaceutically acceptable carrier is an aqueous pH-buffered solution.

Preferred embodiments include sustained-release compositions. An exemplary sustained-release composition has a semi permeable matrix of a solid hydrophobic polymer to which the polypeptide is attached or in which the polypeptide is encapsulated. Examples of suitable polymers include a polyester, a hydrogel, a polylactide, a copolymer of L-glutamic acid and T-ethyl-L-glutamase, non-degradable ethylene-vinylacetate, a degradable lactic acid-glycolic acid copolymer, and poly-D-(−)-3-hydroxybutyric acid. Such matrices are in the form of shaped articles, such as films, or microcapsules.

Exemplary sustained release compositions include polypeptides attached, typically via ϵ-amino groups, to a polyalkylene glycol (e.g., polyethylene glycol [PEG]). Attachment of PEG to proteins is a well-known means of extending in vivo half-life (see, e.g., Abuchowski et al. (1977) *J. Biol. Chem.* 252:3582-86. Any conventional "pegylation" method can be employed, provided the "pegylated" variant retains the desired function(s).

In another embodiment, a sustained-release composition includes a liposomally entrapped polypeptide. Liposomes are small vesicles composed of various types of lipids, phospholipids, and/or surfactants. These components are typically arranged in a bilayer formation, similar to the lipid arrangement of biological membranes. Liposomes containing polypeptides are prepared by known methods, such as, for example, those described in Epstein et al. (1985) *PNAS USA* 82:3688-92, and Hwang et al. (1980) *PNAS USA* 77:4030-34.

Immunogenic compositions of the invention can be stored in any standard form, including, e.g., an aqueous solution or a lyophilized cake. Such compositions are typically sterile when administered to subjects. Sterilization of an aqueous solution is readily accomplished by filtration through a sterile filtration membrane. If the composition is stored in lyophilized form, the composition can be filtered before or after lyophilization and reconstitution.

b. Immunogenic Compositions Comprising Polynucleotides Encoding the Chimeric Envelope Polypeptides or Variants Thereof An alternative to traditional immunization with a polypeptide antigen involves the direct in vivo introduction of a polynucleotide encoding the antigen into tissues of a subject for expression of the antigen by the cells of the subject's tissue. Polynucleotide-based compositions used to vaccinate a subject are termed "polynucleotide vaccines." As used herein, the term "polynucleotide-vaccine" is a vaccine containing one or more polynucleotides encoding an antigen, wherein administration of the polynucleotide to an organism results in expression of the encoded antigen, followed by an immune response to that antigen. Accordingly, an immunogenic composition comprising a chimeric polynucleotide encoding a chimeric envelope polypeptide or variant thereof is provided. Such compositions can include other components including, for example, a storage solution, such as a suitable buffer, e.g., a physiological buffer. In another embodiment, the other component is a pharmaceutically acceptable carrier as described above.

The use of polynucleotide vaccines are described in Donnelly et al. (1997) *Annual Review Immuno* 15:617-648; Gurunathan et al. (2000) *Annu. Rev. Immunol.* 18:927-974; WO 95/20660; WO 93/19183; Conry et al. (1994) *Cancer Res.* 54:1164-1168; Cox et al. (1993) *Virol* 67:5664-5667; Davis et al. (1993) *Hum. Mole. Genet.* 2:1847-1851; Sedegah et al. *Proc. Natl. Acad. Sci.* 91:9866-9870; Montgomery et al. (1993) *DNA Cell Bio.* 12:777-783; Ulmer et al. (1993) *Science* 259:1745-1749; Wang et al. (1993) *Proc. Natl. Acad. Sci.* 90:4156-4160; and, Xiang et al. (1994) *Virology* 199:132-140).

In other embodiments, the composition comprising the polynucleotide encoding the chimeric envelope polypeptide further includes a component that facilitates entry of the polynucleotide into a cell. Components that facilitate intracellular delivery of polynucleotides are well-known and include, for example, lipids, liposomes, water-oil emulsions, polyethylene imines and dendrimers, any of which can be used in compositions according to the invention. Lipids are among the most widely used components of this type, and any of the available lipids or lipid formulations can be employed with the polynucleotides of the invention. Typically, cationic lipids are preferred. Preferred cationic lipids include N-[1-(2,3-dioleyloxy)propyl]--n,n,n-trimethylammonium chloride (DOTMA), dioleoyl phosphotidylethanolamine (DOPE), and/or dioleoyl phosphatidylcholine (DOPC). Polynucleotides can also be entrapped in liposomes, as described above for polypeptides.

In another embodiment, polynucleotides are complexed to dendrimers, which can be used to transfect cells. Dendrimer polycations are three dimensional, highly ordered oligomeric and/or polymeric compounds typically formed on a core molecule or designated initiator by reiterative reaction sequences adding the oligomers and/or polymers and providing an outer surface that is positively charged. Suitable dendrimers include, but are not limited to, "starburst" dendrimers and various dendrimer polycations. Methods for the preparation and use of dendrimers to introduce polynucleotides into cells in vivo are well known to those of skill in the art and described in detail, for example, in PCT/US83/02052 and U.S. Pat. Nos. 4,507,466; 4,558,120; 4,568,737; 4,587,329; 4,631,337; 4,694,064; 4,713,975; 4,737,550; 4,871,779; 4,857,599; and 5,661,025.

Accordingly, the chimeric polynucleotide of the invention can be provided in an expression cassette for expression in a cell. The cassette can include 5' and 3' regulatory sequences operably linked to the chimeric polynucleotide of the invention. "Operably linked" is intended to mean a functional linkage between two or more elements. For example, an operable linkage between a chimeric polynucleotide and a regulatory sequence (i.e., a promoter) is a functional link that allows for expression of the chimeric polynucleotide. Operably linked elements may be contiguous or non-contiguous. When used to refer to the joining of two protein coding regions, by operably linked is intended that the coding regions are in the same reading frame. The cassette may additionally contain at least one additional gene to be cotransformed into the cell of interest. Such an expression cassette is provided with a plurality of restriction sites and/or recombination sites for insertion of the chimeric polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), a chimeric polynucleotide of the invention, and a transcriptional and translational termination region (i.e., termination region) functional in the cell type of interest. The regulatory regions (i.e., promoters, transcriptional regulatory regions, and translational termination regions) and/or the chimeric polynucleotide of the invention may be native/analogous to the host cell or to each other. Alternatively, the regulatory regions and/or the chimeric polynucleotide of the invention may be heterologous to the host cell or to each other.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

As is well known in the art, a large number of factors can influence the efficiency of expression of antigen genes and/or the immunogenicity of DNA vaccines. Examples of such factors include the vector, the promoter used to drive antigen gene expression, and the stability of the inserted gene in the plasmid. Depending on their origin, promoters differ in tissue specificity and efficiency in initiating mRNA synthesis (Xiang et al. (1994) *Virology* 209:564-579; Chapman et al. (1991) *Nucle. Acids. Res.* 19:3979-3986). Many DNA vaccines in mammalian systems have relied upon viral promoters derived from cytomegalovirus (CMV).

c. Additional Components of Immunogenic Compositions

Compositions comprising the polynucleotides or polypeptides can be stored in any standard form, including, e.g., an aqueous solution or a lyophilized cake. Such compositions are typically sterile when administered to cells or subjects. Sterilization of an aqueous solution is readily accomplished by filtration through a sterile filtration membrane. If the composition is stored in lyophilized form, the composition can be filtered before or after lyophilization and reconstitution.

The various immunogenic compositions of the invention can include one or more adjuvant. The term "adjuvant" refers to a compound or mixture that enhances the immune response to an antigen. Exemplary adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and BCG (bacille Calmette-Guerin) and *Corynebacterium parvum*. Selection of an adjuvant depends on the subject to be vaccinated. Preferably, a pharmaceutically acceptable adjuvant is used. A preferred adjuvant for human subjects is alum (alumina gel).

Methods

The immunogenic compositions of the invention can be employed to generate antibodies that recognize the chimeric envelope polypeptide of the invention. The method comprises administering to a subject an immunogenic composition comprising a chimeric envelope polypeptide of the invention or administering to the subject a polynucleotide encoding a chimeric envelope polypeptide of the invention. As outlined in detail below, immunogenic compositions of the invention can be administered to the subject by any suitable route of administration. Accordingly, in one embodiment, an immunogenic composition is administered to a subject to generate antibodies that recognize the heterologous HIV-1 neutralizing epitope. Such antibodies find use in HIV research. Generally, the subject employed in this embodiment is one typically employed for antibody production. Mammals, such as, rodents, rabbits, goats, sheep, etc., are preferred.

The antibodies generated can be either polyclonal or monoclonal antibodies. Polyclonal antibodies are raised by injecting (e.g. subcutaneous or intramuscular injection) antigenic polypeptides into a suitable animal (e.g., a mouse or a rabbit). The antibodies are then obtained from blood samples taken from the animal. The techniques used to produce polyclonal antibodies are extensively described in the literature. Polyclonal antibodies produced by the subjects can be further purified, for example, by binding to and elution from a matrix that is bound with the polypeptide against which the antibodies were raised. Those of skill in the art will know of various standard techniques for purification and/or concentration of polyclonal, as well as monoclonal, antibodies. Monoclonal antibodies can also be generated using techniques known in the art.

In other methods, the immunogenic compositions of the invention can be used to elicit an immune response in a subject. The method comprises introducing into the subject an effective concentration of an immunogenic composition comprising a chimeric envelope polypeptide of the invention or active variant thereof. In further embodiments, the method comprises administering an immunogenic composition comprising a polynucleotide which encodes a chimeric envelope polypeptide of the invention or a variant thereof and expressing the chimeric polynucleotide in the subject.

In other methods, the immunogenic compositions of the invention can be used as vaccines. In one method, the immunogenic composition is administered to individuals who are not infected with HIV-1 to reduce the risk of, or prevent, infection (prophylaxis of HIV-1 infection). The immunogenic composition can also be administered to individuals who are already infected with HIV-1, but are still able to mount an immune response. A so-called "therapeutic vaccine" can ameliorate the existing infection (for example, by improving the subject's condition or slowing or preventing disease progression) and/or can provide prophylaxis against infection with additional HIV-1 strains. Accordingly, methods for inhibiting or preventing infection by HIV-1 in a subject are provided. This method comprises administering to the subject an effective concentration of an immunogenic composition comprising the chimeric envelope polypeptide of the invention or active variant thereof. In further embodiments, the method comprises administering an immunogenic composition comprising a polynucleotide which encodes a chimeric envelope polypeptide of the invention, and expressing the chimeric polynucleotide in the subject.

Polypeptide-based immunogenic compositions are conveniently administered by injection (e.g., subcutaneous, intradermal, intramuscular, intraperitoneal, intravenous, etc.). Alternative routes include oral administration (tablets and the like) and inhalation (e.g., using commercially available nebulizers for liquid formulations or lyophilized or aerosolized formulations). Polypeptide compositions may also be administered via microspheres, liposomes, immune-stimulating complexes (ISCOMs), or other microparticulate delivery systems or sustained release formulations introduced into suitable tissues (such as blood).

As discussed above, polynucleotide-based immunogenic compositions of the invention can be employed to express an encoded polypeptide in vivo, in a subject, thereby eliciting an immune response against the encoded polypeptide. Various methods are available for administering polynucleotides into animals. the selection of a suitable method for introducing a particular polynucleotide into an animal is within the level of skill in the art. See, for example, Zhu et al. (1993) *Science* 261:209-211; Ulmer et al. (1993) *Science* 259:1745-1749; WO 93/17706; Eisenbraun et al. (1993) *DNA Cell Biol.* 12: 791-797. Polynucleotides of the invention can also be introduced into a subject by other methods known in the art, e.g., transfection, electroporation, microinjection, transduction, cell fusion, DEAE dextran, calcium phosphate precipitation, lipofection (lysosome fusion), or a DNA vector transporter (see, e.g., Wu et al. (1992) *J. Biol. Chem.* 267:963-967; Wu and Wu (1988) *J. Biol. Chem.* 263:14621-14624; Canadian Patent Application No. 2,012,311).

An "effective concentration" is defined herein as an amount of a biologically active agent that produces an intended biological activity. The effective concentration of either the chimeric envelope polypeptide or the chimeric envelope polynucleotide administered in the immunogenic composition depends on the properties of the particular composition, e.g., the immunogenicity of a particular formulation, administration route, immunization regimen, condition of the subject and the like, and the determination of a suitable dose for a particular set of circumstances is within the level of skill in the art. Different dosages can be used in a series of sequential inoculations. Thus, the practitioner may administer a relatively large dose in a primary inoculation and then boost with relatively smaller doses of the chimeric envelope polypeptide.

The immune response against the heterologous epitope of the chimeric polypeptide can be generated by one or more inoculations of a subject with an immunogenic composition of the invention. A first inoculation is termed a "primary inoculation" and subsequent immunizations are termed "booster inoculations." Booster inoculations generally enhance the immune response, and immunization regimens including at least one booster inoculation are preferred. Any type of immunogenic composition described above may be used for a primary or booster immunization. Thus, for example, an immunogenic composition comprising polynucleotides (e.g., or a virus-derived vaccine) of the invention can be used for a primary immunization, followed by boosting with an immunogenic composition containing polypeptides of the invention, or vice versa. In addition, a primary immunization and one or more booster immunization can provide the same chimeric polypeptide and/or different chimeric polypeptides.

In one embodiment, a suitable immunization regimen includes at least three separate inoculations with one or more immunogenic compositions of the invention, with a second inoculation being administered more than about two, about three to eight, or about four, weeks following the first inoculation. Generally, the third inoculation is administered several months after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory."

The adequacy of the vaccination parameters chosen, e.g., formulation, dose, regimen and the like, can be determined by taking aliquots of serum from the subject and assaying antibody titers during the course of the immunization program. Alternatively, the T cell populations can by monitored by conventional methods. In addition, the clinical condition of the subject can be monitored for the desired effect, e.g., prevention of HIV-1 infection or progression to ASDS, improvement in disease state (e.g., reduction in viral load), or reduction in transmission frequency to an uninfected partner. If such monitoring indicates that vaccination is sub-optimal, the subject can be boosted with an additional dose of immunogenic composition, and the vaccination parameters can be modified in a fashion expected to potentiate the immune response. Thus, for example, the dose of the chimeric envelope polypeptide or polynucleotide and/or adjuvant can be increased or the route of administration can be changed.

The following examples are offered by way of illustration and not by way of limitation.

EXPERIMENTAL

Example 1

HIV-1 and HIV-2 share less than 50% sequence similarity in envelope and they generally exhibit little cross-neutralization. We postulated that HIV-1 neutralizing antibody (Nab) epitopes could be identified in, or molecularly engineered into, functional HIV-2 env glycoproteins. Sequence alignments of HIV-1 and HIV-2 viruses were examined to identify conserved regions in the membrane proximal external region (MPER) of gp41 and site-directed mutagenesis was used to change selected amino acids in this region of HIV-2 to resemble HIV-1. HIV-2 virions bearing envelopes with 4E 10 core epitope amino acids, or control viruses containing wild-type HIV-1 or HIV-2 env, were analyzed for neutralization susceptibility to a panel of HIV-1 and HIV-2 monoclonal antibodies (Mab) or HIV-1 infected patient plasma using a JC53b1-13 HIV entry assay previously described (*Nature* 422:307, 2003).

The neutralization of HIV-2 by 4E10 and 2F5 monoclonal antibody was demonstrated. HIV-2 viruses 7312A, UC1, and ST were pre-incubated for 1 hour at 37° C. with the indicated concentrations of 4E10 and 2F5 monoclonal antibody. They were then plated on JC53b1-13 cells and infectivity determined after 48 hrs, as described in Decker et al (submitted and incorporated into this patent application). Site-directed mutations in the HIV-2 7312A envelope at positions 675 (L to I) and 676 (A to T) making the sequence of the 4E10 epitope identical to that of HIV-1 YU2 (see inset of FIG. 5) rendered the virus susceptible to 4E10; conversely, altering these same two amino acids in the 4E10 sensitive HIV-2 ST virus to alanine residues rendered this virus resistant to 4E10 (data not shown).

More specifically, virus bearing a prototypic HIV-1 env glycoprotein (YU2) was intermediately sensitive to neutralization by 4E10 (IC50=25 ug/ml), 2F5 (IC50=25 ug/ml), and b12 (IC50=3 ug/ml). Virus containing the envelope of HIV-2 strain 7312A was resistant to neutralization by all three Mabs (IC50>50 ug/ml). Site-directed substitution of amino acid 675 of SEQ ID NO: 10 (L to I) and amino acid 676 of SEQ ID NO: 10 (A to T) in the 7312A MPER (corresponding to amino acid positions 673 and 674, respectively, of SEQ ID NO:2) rendered the virus remarkably sensitive to neutralization by 4E10 (IC50=0.8 ug/ml) (See, FIG. 5) but not by 2F5 or b12. Conversely, altering these same two amino acids in the 4E10 sensitive HIV-2 ST virus to alanine residues rendered this virus resistant to 4E10 (data not shown). Two naturally-occurring strains of HIV-2 (ST and UC1) were found to be extremely sensitive to neutralization by 4E10 (IC50=0.1 and 1.2 ug/ml, respectively) but were resistant to 2F5 and b12. Twenty-four HIV-1 clade B patient plasmas were examined for 4E10-like Nabs; six showed evidence of neutralization with reciprocal IC50 titers between 0.028 and 0.001 (data not shown).

In a similar fashion, site-directed mutations in the HIV-2 7312A envelope at positions 660 (K to A), 662 (N to D), 663 (S to K), and 665(D to A) of SEQ ID NO:2, which together make the HIV-2 sequence identical to that of the 2F5 epitope region of HIV-1 YU2, rendered the modified HIV-2 virus susceptible to 2F5 with an IC50 of <0.1 ug/ml; conversely, the wild-type HIV-2 7312A envelope-containing viruses were completely resistant to 2F5 (IC50>50.0 ug/ml) (data not shown). These data show that certain naturally-occurring or genetically-modified strains of HIV-2 can be used to detect HIV neutralization by 4E10 and 4E10-like antibodies and by 2F5 and 2F5-like antibodies.

Conclusions. Naturally occurring or genetically engineered variants of HIV-2 env glycoprotein can be used to detect and quantify HIV-1 elicited 4E10-like and 2F5 Nabs with great sensitivity (IC50=0.1 ug/ml) and specificity. We have evidence that an analogous approach is feasible for detecting HIV-1 elicited Nabs against other MPER epitopes as well as epitopes on gp120.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An immunogenic composition comprising a chimeric polypeptide, wherein said chimeric polypeptide comprises:
   a) an amino acid sequence encoding an HIV-2 envelope polypeptide, a functional variant of the HIV-2 envelope polypeptide, a Simian Immunodeficiency virus (SIV) envelope polypeptide, or a functional variant of the SIV envelope polypeptide; and
   b) a heterologous epitope selected from the group consisting of:
      i) a heterologous epitope comprising the amino acid sequence set forth in SEQ ID NO:38, or a functional variant thereof, wherein the amino acid sequence of said functional variant differs from SEQ ID NO:38 by up to three amino acids;
      ii) a heterologous epitope comprising the amino acid sequence set forth in SEQ ID NO:15, or an immunologically equivalent epitope thereof, wherein the amino acid sequence of said immunologically equivalent epitope differs from SEQ ID NO:15 by one amino acid; and
      iii) a heterologous epitope comprising the amino acid sequence set forth in SEQ ID NO:16, or an immunologically equivalent epitope thereof, wherein the amino acid sequence of said immunologically equivalent epitope differs from SEQ ID NO:16 by up to two amino acids;

wherein said heterologous epitope is recognized by an HIV-1 neutralizing antibody, and wherein said heterologous epitope is located at a position within said amino acid sequence of a).

2. An immunogenic composition comprising a chimeric polynucleotide, wherein said chimeric polynucleotide comprises:
   a) a nucleotide sequence encoding an HIV-2 envelope polypeptide, a functional variant of the HIV-2 envelope polypeptide, a Simian Immunodeficiency virus (SIV) envelope polypeptide, or a functional variant of the SIV envelope polypeptide; and
   b) a nucleotide sequence encoding an amino acid sequence comprising a heterologous epitope, wherein said heterologous epitope is selected from the group consisting of:
      i) a heterologous epitope comprising the amino acid sequence set forth in SEQ ID NO:38, or a functional variant thereof, wherein the amino acid sequence of said functional variant differs from SEQ ID NO:38 by up to three amino acids;
      ii) a heterologous epitope comprising the amino acid sequence set forth in SEQ ID NO:15, or an immunologically equivalent epitope thereof, wherein the amino acid sequence of said immunologically equivalent epitope differs from SEQ ID NO:15 by one amino acid; and
      iii) a heterologous epitope comprising the amino acid sequence set forth in SEQ ID NO:16, or an immunologically equivalent epitope thereof, wherein the amino acid sequence of said immunologically equivalent epitope differs from SEQ ID NO:16 by up to two amino acids;

wherein said heterologous epitope is recognized by an HIV-1 neutralizing antibody, and wherein said nucleotide sequence of b) is located at a position within said nucleotide sequence of a).

3. The immunogenic composition of claim 1, wherein said chimeric polypeptide is displayed on a virus, a viral-like particle or is displayed on a virally infected cell.

4. The immunogenic composition of claim 3, wherein said viral-like particle comprises an inactivated, an attenuated, or a replication-defective viral-like particle.

5. The immunogenic composition of claim 1, wherein said composition further comprises a pharmaceutically acceptable carrier, diluent, or adjuvant.

6. A method of eliciting an immune response in a subject comprising:
   Administering to the subject an effective concentration of an immunogenic composition of claim 1;
   and thereby eliciting the immune response in said subject.

7. The method of claim 6, wherein said epitope is from gp41 or gp120.

8. The method of claim 6, wherein said epitope comprises the membrane proximal external region or a functional variant thereof.

9. The method of claim 7, wherein said epitope comprises a 4E10 epitope, a Z13 epitope, or a 2F5 epitope.

10. The method of claim 6, wherein said epitope is from the variable loop region of gp120.

11. The method of claim 6, wherein said chimeric polypeptide is displayed on a virus, a viral-like particle or is displayed on a virally infected cell.

12. The method of claim 11, wherein said viral-like particle comprises an inactivated, an attenuated, or a replication-defective viral-like particle.

13. The method of claim 6, wherein said immunogenic composition is administered with a pharmaceutically acceptable carrier or diluent.

14. The method of claim 6, wherein said immunogenic composition is administered with one or more adjuvant.

15. The method of claim 6, wherein said immunogenic composition is administered subcutaneously, intraperitoneally, intramuscularly, orally, or via nasal administration.

16. The method of claim 6, wherein said heterologous epitope is from an HIV-1 envelope polypeptide.

17. The immunogenic composition of claim 1, wherein said heterologous epitope comprises the amino acid sequence set forth in SEQ ID NO:38.

18. The immunogenic composition of claim 1, wherein said heterologous epitope comprises the amino acid sequence set forth in SEQ ID NO:15.

19. The immunogenic composition of claim 1, wherein said heterologous epitope comprises the amino acid sequence set forth in SEQ ID NO:16.

20. The immunogenic composition of claim 2, wherein said heterologous epitope comprises the amino acid sequence set forth in SEQ ID NO:38.

21. The immunogenic composition of claim 2, wherein said heterologous epitope comprises the amino acid sequence set forth in SEQ ID NO:15.

22. The immunogenic composition of claim 2, wherein said heterologous epitope comprises the amino acid sequence set forth in SEQ ID NO:16.

23. A method of eliciting an immune response in a subject comprising:

administering to the subject an effective concentration of an immunogenic composition of claim 2;

and thereby eliciting the immune response in said subject.

24. The method of claim 23, wherein said immunogenic composition is administered with a pharmaceutically acceptable carrier or diluent.

25. The method of claim 23, wherein said immunogenic composition is administered with one or more adjuvant.

26. The method of claim 23, wherein said immunogenic composition is administered subcutaneously, intraperitoneally, intramuscularly, orally, or via nasal administration.

* * * * *

UNITED STATES PATENT AND TRADEMARK OFFICE
CERTIFICATE OF CORRECTION

| | | |
|---|---|---|
| PATENT NO. | : 8,647,818 B2 | Page 1 of 1 |
| APPLICATION NO. | : 11/816624 | |
| DATED | : February 11, 2014 | |
| INVENTOR(S) | : Shaw et al. | |

It is certified that error appears in the above-identified patent and that said Letters Patent is hereby corrected as shown below:

<u>In the Claims</u>

Column 118, line 61 through Column 119, line 2: Claims 7, 8, 9, and 10 should be deleted.

Column 119, lines 16-17: Claim 16 should be deleted.

Signed and Sealed this
Twenty-seventh Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,647,818 B2
APPLICATION NO. : 11/816624
DATED : February 11, 2014
INVENTOR(S) : Shaw et al.

Page 1 of 3

It is certified that error appears in the above-identified patent and that said Letters Patent is hereby corrected as shown below:

Delete the Title Page and Page 2 and substitute therefore the attached Title Page and Page 2 showing the corrected number of claims in patent.

In the Claims

Column 118, line 61 through Column 119, line 2: Claims 7, 8, 9, and 10 should be deleted.

Column 119, lines 16-17: Claim 16 should be deleted.

This certificate supersedes the Certificate of Correction issued May 27, 2014.

Signed and Sealed this
First Day of July, 2014

Michelle K. Lee
*Deputy Director of the United States Patent and Trademark Office*

United States Patent
Shaw et al.

(10) Patent No.: US 8,647,818 B2
(45) Date of Patent: Feb. 11, 2014

(54) MOLECULAR SCAFFOLDS FOR HIV-1 IMMUNOGENS

(75) Inventors: George M. Shaw, Birmingham, AL (US); Beatrice H. Hahn, Birmingham, AL (US); Frederic Bibollet-Ruche, Birmingham, AL (US); Peter D. Kwong, Washington, DC (US)

(73) Assignees: UAB Research Foundation, University of Alabama—Birmingham, Birmingham, AL (US); The United States of America, as represented by the Secretary, Department of Health and Human Services (Hereinafter the Government) Office of Technology Transfer, National Institutes of Health, Washington, DC (US)

( * ) Notice: Subject to any disclaimer, the term of this patent is extended or adjusted under 35 U.S.C. 154(b) by 1008 days.

(21) Appl. No.: 11/816,624
(22) PCT Filed: Feb. 16, 2006
(86) PCT No.: PCT/US2006/005363
§ 371 (c)(1),
(2), (4) Date: Nov. 12, 2008
(87) PCT Pub. No.: WO2006/091455
PCT Pub. Date: Aug. 31, 2006

(65) Prior Publication Data
US 2009/0162390 A1    Jun. 25, 2009

Related U.S. Application Data
(60) Provisional application No. 60/669,612, filed on Apr. 8, 2005, provisional application No. 60/654,340, filed on Feb. 18, 2005.

(51) Int. Cl.
| C12Q 1/70 | (2006.01) |
| A61K 39/00 | (2006.01) |
| A61K 39/12 | (2006.01) |
| A61K 39/21 | (2006.01) |
| A61K 39/38 | (2006.01) |
| C07K 16/00 | (2006.01) |

(52) U.S. Cl.
USPC ......... 435/5; 435/339; 435/339.1; 530/388.3; 530/388.35; 424/184.1; 424/185.1; 424/186.1; 424/187.1; 424/188.1

(58) Field of Classification Search
None
See application file for complete search history.

(56) References Cited

U.S. PATENT DOCUMENTS

| 5,866,137 A | 2/1999 | Rovinski et al. |
| 5,912,176 A | 6/1999 | Wang et al. |
| 6,328,973 B1 | 12/2001 | Devico et al. |
| 2008/0096187 A1 * | 4/2008 | Shaw et al. ............ 435/5 |

FOREIGN PATENT DOCUMENTS

| WO | WO 03/033666 A2 | 4/2003 |
| WO | WO 2004/052933 A2 | 6/2004 |
| WO | WO 2005/111621 A2 | 11/2005 |
| WO | WO2005111621 | * 11/2005 ......... G01N 33/569 |

OTHER PUBLICATIONS

Robert-Guroff, et al. Cross-Neutralization of Human Immunodeficiency Virus Type 1 and 2 and Simian Immunodeficiency Virus Isolates. J. Virol. 1992; 66(6):3602-3608.*

Nyambi, et al. Study of the Dynamics of Neutralization Escape Mutants in a Chimpanzee Naturally Infected with the Simian Immunodeficiency Virus SIVcpz-ant. J. Virol. 1997; 71(3):2320-2330.*

Han, et al. The use of a chimera HIV-1/HIV-2 envelope protein for immunodiagnosis of HIV infection: its expression and purification in E. coli by use of a translation initiation site within HIV-1 env gene. Biochemistry and molecular biology international. 1998; 46(3): p. 607-17.*

Wagner, et al. Construction, Expression, and Immunogenicity of Chimeric HIV-1 Virus-like Particles. Virology. 1996; 220: 128-140.*

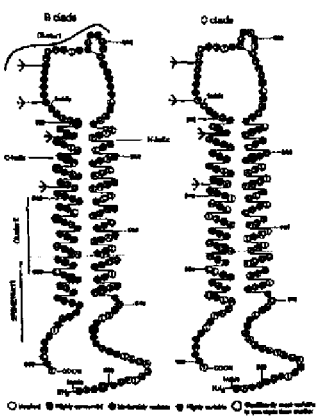

Hansen, et al. An O-linked carbohydrate neutralization epitope of HIV-1 gp120 is expressed by HIV-1 env gene recombinant vaccinia virus. Arch Virol. 1992; 126: 11-20.*

Schweighardt, et al. R5 Human Immunodeficiency Virus Type 1 (HIV-1) Replicates More Efficiently in Primary CD4+ T-Cell Cultures Than X4 HIV-1. J. Virol. 2004; 78(17): 9164-9173.*

Schanzer, et al. Development of Tetravalent, Bispecific CCR5 Antibodies with Antiviral Activity against CCR5 Monoclonal Antibody-Resistant HIV-1 Strains. Antimicrob Agents Chemother. 2011; 55(5): 2369-2378.*

Chen, et al. AFM force measurements of the gp120-sCD4 and gp120 or CD4 antigen-antibody interactions. Biochemical and Biophysical Research Communications. 2011; 407(2): 301-306.*

Scott, et al., Evaluation of a candidate human immunodeficiency virus type 1 (HIV-1) vaccine in macaques: effect of vaccination with HIV-1 gp120 on subsequent challenge with heterologous simian immunodeficiency virus—HIV-1 chimeric virus. Journal of General Virology. 1998; 79: 423-432.*

Mamounas, et al. An Infectious Chimeric Human Immunodeficiency Virus Type 2 (HIV-2) Expressing the HIV-1 Principal Neutralizing Determinant. J. Virol. 1995; 69(10): 6424-6429.*

Zwick, et al. Broadly Neutralizing Antibodies Targeted to the Membrane-Proximal External Region of Human Immunodeficiency Virus Type 1 Glycoprotein gp41. J. Virol. 2001; 75(22): 10892-10905.*

Wagner, et al. Construction, Expression, and Immunogenicity of Chimeric HIV-1 Virus-like Particles. Virology. 1996; 220:128-140.*

Zwick, et al. Broadly Neutralizing Antibodies Targeted to the Membrane-Proximal External Region of Human Immunodeficiency Virus Type 1 Glycoprotein gp41. J. Virol. 2001;75(22): 10892-10905.*

Burton, et al. HIV vaccine design and the neutralizing antibody problem. Nature Immunol. 2004; 5(3): 233-236.*

Zwick, M.B. The membrane-proximal external region of HIV-1 gp41: a vaccine target worth exploring. AIDS, 2005; 19: 1725-1737.*

Zwick, et al. Anti-Human Immunodeficiency Virus Type 1 (HIV-1) Antibodies 2F5 and 4E10 Require Surprisingly Few Crucial Residues in the Membrane-Proximal External Region of Glycoprotein gp41 to Neutralize HIV-1. J. Virol. 2005; 79(2): 1252-1261.*

Breuer, J., et al., "Human Immunodeficiency Virus Type 2 (HIV-2) env Gene Analysis: Prediction of Glycoprotein Epitopes Important for Heterotypic Neutralization and Evidence for Three Genotype Clusters within the HIV-2a Subtype" (1995) Journal of General Virology, pp. 333-345, vol. 76.

Ofek, G., et al., "Structure and Mechanistic Analysis of the Anti-Human Immunodeficiency Virus Type 1 Antibody 2F5 in Complex with Its gp41 Epitope" (Oct. 2004) Journal of General Virology, pp. 10724-10737, vol. 78.

Barnett, S.W. et al., "Distinguishing Features of an Infectious Molecular Clone of the Highly Divergent and Noncytopathic Human Immunodeficiency Virus Type 2 UCI Strain," Journal of Virology, Feb. 1993, pp. 1006-1014, vol. 67, No. 2.

Burton, D. R., et al., "HIV Vaccine Design and the Neutralizing Antibody Problem," Nature Immunology, Mar. 2004, pp. 233-236, vol. 5, No. 3.

Kong, L.I., et al., "West African HIV-2-Related Human Retrovirus with Attenuated Cytopathicity," Science, Jun. 10, 1988, pp. 1525-1529, vol. 240.

Mamounas, M., et al., "An Infectious Chimeric Human Immunodeficiency Virus Type 2 (HIV-2) Expressing the HIV-1 Principal Neutralizing Determinant," Journal of Virology, Oct. 1995, pp. 6424-6429, vol. 69, No. 10.

Nabel, G.J., "Close to the Edge: Neutralizing the HIV-1 Envelope," Science, Jun. 24, 2005, pp. 1878-1879, vol. 308.

Shi, Y., et al., "Evolution of Human Immunodeficiency Virus Type 2 Coreceptor Usage, Autologous Neutralization, Envelope Sequence and Glycosylation," Journal of General Virology, 2005, pp. 3385-3396, vol. 86.

Thomas, E.R., et al., "CD4-dependent and CD4-independent HIV-2: Consequences for Neutralization," AIDS, 2003, pp. 291-300, vol. 27.

Weiss, R.A., et al., :"HIV-2 Antisera Cross-neutralize HIV-1," AIDS, 1988, pp. 95-100, vol. 2.

Zwick, M.B., et al., "Broadly Neutralizing Antibodies Targeted to the Membrane-Proximal External Region of Human Immunodeficiency Virus Type 1 Glycoprotein gp41," Journal of Virology, Nov. 2001, pp. 10892-10905, vol. 75, No. 22.

Zwick, M.B., et al., "Anti-Human Immunodeficiency Virus Type 1 (HIV-1) Antibodies 2F5 and 4E10 Require Surprisingly Few Crucial Residues in the Membrane-Proximal External Region of Glycoprotein gp41 to Neutralize HIV-1," Journal of Virology, Jan. 2006, pp. 1252-1261, vol. 79, No. 2.

* cited by examiner

*Primary Examiner* — Jeffrey Stucker
*Assistant Examiner* — Stuart W Snyder
(74) *Attorney, Agent, or Firm* — Alston & Bird LLP

(57) ABSTRACT

Methods and compositions are provided which employ chimeric polypeptides having at least one heterologous epitope for a human immunodeficiency virus type 1 (HIV-1) neutralizing antibody. These chimeric polypeptides behave as molecular scaffolds which are capable of presenting the various heterologous HIV-1 epitopes. The invention demonstrates that a heterologous epitope recognized by the HIV-1 neutralizing antibody can be more fully exposed to neutralizing antibodies when presented within the backbone of the chimeric polypeptide than when the epitope is presented within the context of an HIV-1 backbone. Polynucleotides encoding these chimeric polypeptides are also provided. Immunogenic compositions are provided which comprise a chimeric polypeptide having at least one heterologous epitope that interacts with an HIV-1 neutralizing antibody. Immunogenic compositions comprising chimeric polynucleotides encoding the chimeric polypeptides of the invention are also provided. Vaccines comprising such immunogenic compositions are also provided. Further provided are methods which employ the immunogenic compositions of the invention. Such methods include, for example, methods for eliciting an immune response in a subject, methods for generating antibodies specific for the chimeric polypeptide or the chimeric polypeptide, and methods for inhibiting or preventing infection by HIV-1 in a subject.

21 Claims, 14 Drawing Sheets